(12) United States Patent
Jewell et al.

(10) Patent No.: US 10,517,946 B2
(45) Date of Patent: Dec. 31, 2019

(54) POLYELECTROLYTE MULTILAYERS ASSEMBLED FROM IMMUNE SIGNAL COMPOUNDS

(71) Applicant: University of Maryland, College Park, College Park, MD (US)

(72) Inventors: Christopher M. Jewell, Silver Spring, MD (US); Lisa H. Tostanoski, Washington, DC (US); Yu-Chieh Chiu, College Park, MD (US)

(73) Assignee: University of Maryland, College Park, College Park, MD (US)

( * ) Notice: Subject to any disclaimer, the term of this patent is extended or adjusted under 35 U.S.C. 154(b) by 108 days.

(21) Appl. No.: 15/551,081

(22) PCT Filed: Feb. 16, 2016

(86) PCT No.: PCT/US2016/018002
§ 371 (c)(1),
(2) Date: Aug. 15, 2017

(87) PCT Pub. No.: WO2016/133862
PCT Pub. Date: Aug. 25, 2016

(65) Prior Publication Data
US 2018/0028646 A1   Feb. 1, 2018

Related U.S. Application Data

(60) Provisional application No. 62/116,655, filed on Feb. 16, 2015.

(51) Int. Cl.
*A61K 39/39* (2006.01)
*A61K 39/00* (2006.01)
*A61K 9/16* (2006.01)

(52) U.S. Cl.
CPC ............ *A61K 39/39* (2013.01); *A61K 9/1611* (2013.01); *A61K 9/1676* (2013.01); *A61K 39/00* (2013.01); *A61K 39/0008* (2013.01); *A61K 2039/55555* (2013.01); *A61K 2039/55561* (2013.01); *A61K 2039/57* (2013.01); *A61K 2039/572* (2013.01); *A61K 2039/575* (2013.01); *A61K 2039/577* (2013.01)

(58) Field of Classification Search
None
See application file for complete search history.

(56) References Cited

U.S. PATENT DOCUMENTS 7,807,633 B2 * 10/2010 Haynie .................. C07K 17/00
424/443
2010/0034875 A1 * 2/2010 Haynie .................. B82Y 30/00
424/463

OTHER PUBLICATIONS

Chiu, et al. (2016) "Assembly and Immunological Processing of Polyelectrolyte Multilayers Composed of Antigens and Adjuvants", ACS Applied Materials & Interfaces, 8: 18722-31. (Year: 2016).*
Demento et al., Inflammasome-activating nanoparticles as modular systems for optimizing vaccine efficacy, Vaccine, vol. 27, No. 23, pp. 3013-3021. May 18, 2009.
Chiu et al., Modular Vaccine Design Using Carrier-Free Capsules Assembled from Polyionic Immune Signals, ACS Biomaterials Science & Engineering, vol. 1, No. 12, pp. 1200-1205. Nov. 4, 2015.
Zhang et al., Polyelectrolyte Multilayers Assembled Entirely from Immune Signals on Gold Nanoparticle Templates Promote Antigen-Specific T Cell Response, ACS Nano, vol. 9, No. 6, pp. 6465-6477. Jun. 23, 2015.
Jewell, C.M., et al., Multilayered Polyelectrolyte Assemblies as Platforms for the Delivery of DNA and Other Nucleic Acid-Based Therapeutics, Adv Drug Deliv Rev., Jun. 10, 2008, vol. 60, No. 9, pp. 979-999.
DeGeest, B.G., et al., Surface-Engineered Polyelectrolyte Multilayer Capsules: Synthetic Vaccines Mimicking Microbial Structure and Function, Angew. Chem. Int. Ed., Apr. 16, 2012, vol. 51, No. 16, pp. 3862-3866.
Saurer, E.M., et al. Polyelectrolyte Multilayers Promote Stent-Mediated Delivery of DNA to Vascular Tissue, Biomacromolecules, May 13, 2013, vol. 14, No. 5, pp. 696-704.
Zebli, B., et al., Magnetic targeting and cellular uptake of polymer microcapsules simultaneously functionalized with magnetic and luminescent nanocrystals, Langmuir, May 10, 2005, vol. 21, No. 10, pp. 4262-4265.
Yan, Y. et al., Assembly of Layer-by-Layer Particles and Their Interactions with Biological Systems, Chem. Mater., Aug. 22, 2013, vol. 26, No. 1, pp. 452-460.

* cited by examiner

*Primary Examiner* — Robert M Kelly
(74) *Attorney, Agent, or Firm* — Hodgson Russ LLP

(57) ABSTRACT

Immune-polyelectrolyte multilayers (iPEMs) that can be made entirely from immune signal compounds are provided. The iPEMs are formed from first layer of a first immune signal compound, and a second layer of the first immune signal compound or a second immune signal compound disposed on the first layer of the first immune signal compound. The immune signal compounds are peptides, polypeptides, nucleic acids, charged derivatives thereof. Combinations of the immune signal compounds may be in adjacent layers. The first immune signal compound and the second immune signal compound have oppositely charged domains. iPEMs can be formed on or include a substrate, such as a sacrificial substrate, which allows for the formation of a three-dimensional void which can hold various other compounds for use in modulating immune responses. The iPEMs are for use in either stimulating an immune response to one or more antigens, or inducing tolerance to one or more antigens. Methods of stimulating immune responses, or inducing tolerance using the iPEMs, are also provided.

21 Claims, 27 Drawing Sheets

Specification includes a Sequence Listing.

POLYELECTROLYTE MULTILAYERS ASSEMBLED FROM IMMUNE SIGNAL COMPOUNDS

CROSS-REFERENCE TO RELATED APPLICATIONS

This application claims priority to U.S. Provisional Application No. 62/116,655, which was filed on Feb. 16, 2015, the disclosure of which is hereby incorporated by reference.

BACKGROUND OF THE DISCLOSURE

Despite the tremendous clinical success of vaccines and other approaches to modulating immune responses, the complexity of some of the most pervasive diseases, autoimmune disorders and conditions such as allergic reactions continue to present formidable challenges. For example, the human immunodeficiency virus (HIV) is able to evade immune clearance by rapid mutation and concealment in the mucosa, and cancerous tissues actively suppress tumor-destructive immune cells. Likewise, the prevalence and toll of autoimmune diseases, such as multiple sclerosis, rheumatoid arthritis, lupus, type I diabetes, celiac disease, as well as a wide variety of allergic reactions, represent critical types of immune system challenges for which improved compositions and methods are needed. An obstacle to achieving this goal is the complex composition (e.g., carriers, excipients, adjuvants, antigens) that makes characterizing and testing the multitude of new vaccine and other immune-modulatory candidates empirical and economically infeasible. Moreover, while numerous biomaterials have been explored to improve adjuvant and other immune-modulatory performance through controlled release, co-delivery of multiple cargoes, and targeting to sites such as lymph nodes, recent studies have led to a revelation that many ubiquitous polymeric vaccine carriers activate inflammatory pathways even in the absence of other antigens or adjuvants. Examples of both degradable and non-degradable materials have been reported in this context, including poly(lactide-co-glycolide), poly(styrene), chitosan, and hyaluronic acid. (See, for example, Sharp, F. et al. *Proceedings of the National Academy of Sciences of the United States of America* 2009, 106 (3), 870-5; Demento, S. L. et al. *Vaccine* 2009, 27 (23), 3013-21; Da Silva, C. A. et al. *J Immunol* 2009, 182 (6), 3573-82; and Termeer, C. et al. *J Exp Med* 2002, 195 (1), 99-111). Thus, while polymeric materials offer great potential for new vaccines, the intrinsic immune characteristics can hinder rational vaccine design and translation because the role of the carrier itself may alter how other components or signals (e.g., antigens, adjuvants) are processed. Thus, there is a need for improved compositions and methods that avoid the unintended effects of carriers, and yet can be tuned for providing a variety of effects on adaptive immunity, such as either stimulating an immune response that is specific for a particular antigen, or inducing tolerance to it. The present disclosure is pertinent to these needs.

SUMMARY OF THE DISCLOSURE

The present disclosure relates to novel polyelectrolyte multilayer (PEM) materials that can be built entirely from immune signals. These immune-PEMs (iPEMs) provide a new platform for rationally-designing PEM coatings from immune signals in a way that reduces or eliminates potentially confounding intrinsic properties of synthetic polymers or other structural components often included in previously available PEM films. The iPEMs can be tuned to modulate immune responses for either stimulating an adaptive immune response, or for inducing immune tolerance to a variety of antigens. The compositions comprise, consist essentially of, or consist of: a) a first layer of a first immune signal compound; and b) a second layer of the first immune signal compound or a second immune signal compound disposed on the first layer of the first immune signal compound. The immune signal compounds are selected from peptides, polypeptides, nucleic acids, and charged derivatives thereof. Combinations of the immune signals in adjacent layers, or mixtures of immune signals in any individual layer are included. The first immune signal compound and the second immune signal compound have oppositely charged domains. The composition can comprise additional layers, such as from 1 to 40 additional layer(s) of immune signal compound(s) wherein the layers are disposed on the adjacent layers, and adjacent layers have opposite charges.

In certain implementations the immune signal compound is a peptide or polypeptide or charged derivative thereof for use in stimulating an immune response, and comprises an antigen expressed by a cancer cell or a pathogen. In certain implementations the immune signal compound is a peptide or polypeptide or charged derivative thereof for use in inducing tolerance to an antigen, and the polypeptide or peptide comprises a self-antigen or an allergen.

In certain aspects an immune signal compound in a composition of the disclosure comprises a polynucleotide, such as a Toll-like-receptor (TLR) ligand, which may be an agonist or an antagonistic TLR ligand. In certain approaches the immune signal compound comprises a synthetic analog of double-stranded RNA. In certain embodiments an immune signal is a TLR9 antagonist. In a non-limiting embodiment the immune signal compound can be a suppressive CpG oligodeoxynucleotide.

Compositions of the disclosure can further comprise a substrate, wherein a first layer of the first immune signal compound is disposed on at least a portion of a surface of the substrate. The substrate can be a sacrificial substrate, such as calcium carbonate, magnesium carbonate, cadmium carbonate, melamine formaldehyde, silicon dioxide, or the substrate can be a living cell, or a nanoparticle or microparticle, and may be a metal core. The substrate can be a microscope slide, a scaffold, a medical implant, or a biomedical device. The substrate can also be a microneedle and/or microneedle array. In certain approaches the composition comprises a three-dimensional void, which can if desired Methods of making compositions of the disclosure are included In another aspect the disclosure provides a method of modulating an immune response. In general the method comprises administering a composition of the disclosure to an individual in need thereof, such that either an adaptive immune response to an antigen component of the composition is stimulated, or tolerance to an antigen component of the composition is induced. Thus, the antigen can be a peptide or polypeptide expressed by a cancer cell or a pathogen, or an antigen to which development of tolerance would be of benefit to the individual, such as in the case of autoimmune conditions and allergic reactions. In one aspect, the method of the disclosure promotes development of antigen specific regulatory T cells.

DESCRIPTION OF THE DISCLOSURE

Figure 1:
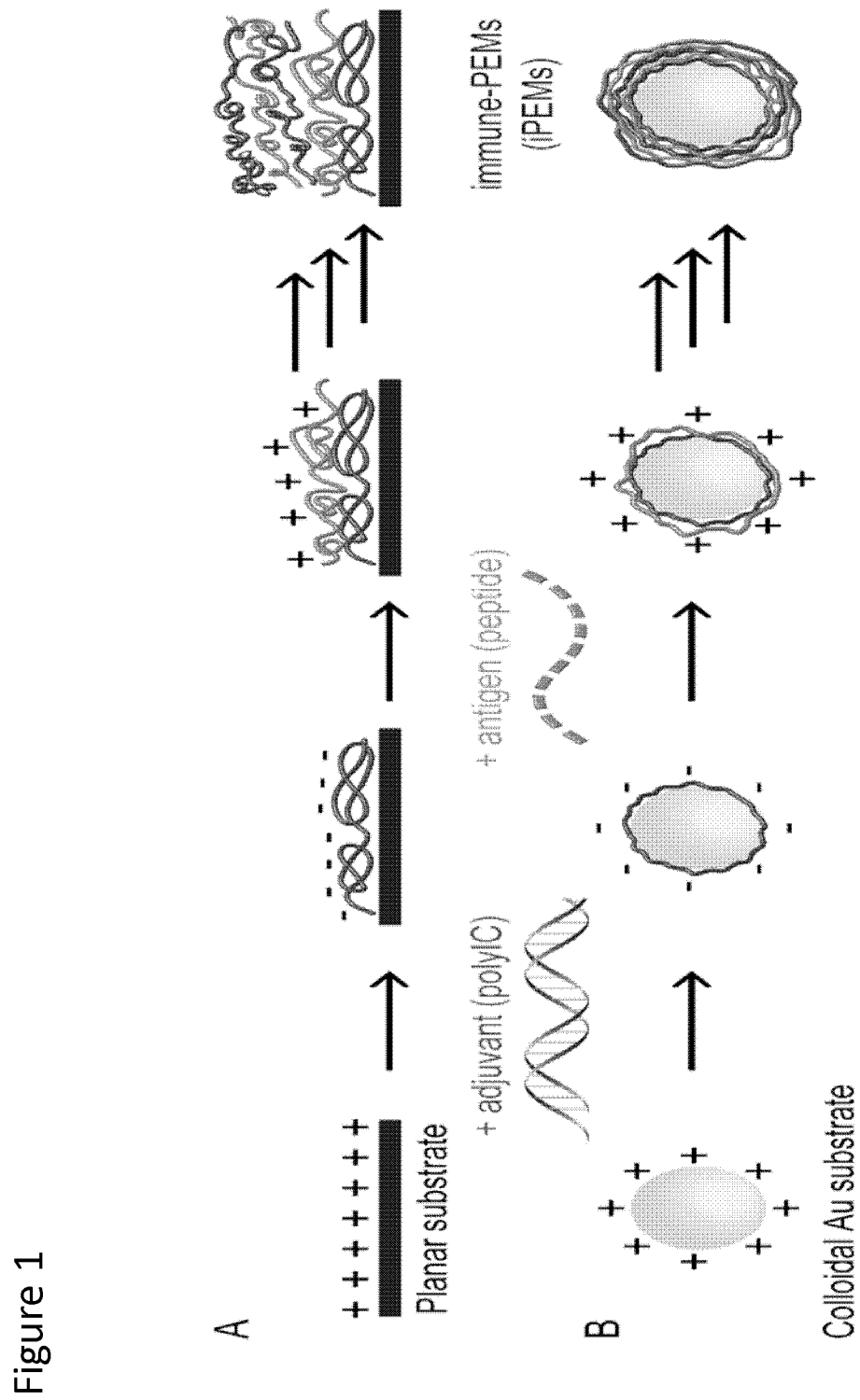
FIG. 1. Schematic depiction of a layer-by-layer approach to assemble immune-PEMs (iPEMs) from adjuvants and antigens on (A) planar or (B) gold nanoparticle substrates.

Throughout this specification, where a value of ranges is provided, it is understood that each intervening value, to the tenth of the unit of the lower limit unless the context clearly dictates otherwise, between the upper and lower limit of that range and any other stated or intervening value in that stated range, is encompassed within the disclosure. The upper and lower limits of these smaller ranges which may independently be included in the smaller ranges is also encompassed within the disclosure, subject to any specifically excluded limit in the stated range.

Each polynucleotide sequences presented in this disclosure includes its complementary sequence, as well as complementary and reverse complementary sequences. All DNA sequences include their RNA equivalents, and all RNA sequences include their DNA and cDNA equivalents. Every peptide and polypeptide sequence described herein includes every polynucleotide sequence encoding it.

In certain aspects, the present disclosure provides compositions comprising one or more immunomodulatory components. The immunomodulatory components can comprise, consist essentially of, or consist of biological molecules, such as immune signal compounds, that are capable of specifically affecting one or more properties of cells involved in adaptive immunity. The compositions themselves in certain examples can comprise, consist essentially of, or consist of immune signal compounds. Those skilled in the art will recognize that a composition or process of this disclosure that "consists essentially of" a specified material or step(s) means that the composition or process may include other step(s) or material(s) that do not materially affect the basic and novel characteristics of the particular example. In certain examples, compositions of this disclosure include no non-biological polymers, and thus may be formed exclusively of biological macromolecules, such as polynucleotides, peptides, polypeptides, proteins, and charged derivatives and combinations thereof. In certain examples, the compositions, or an immunomodulatory component of a composition, comprises, consists essentially of, or consists of biological macromolecules selected from the group consisting of polynucleotides, peptides, polypeptides, proteins, and charged derivative and combinations thereof. In examples the compositions comprise a combination of at least one polynucleotide and at least one peptide or polypeptide.

A composition can comprise one or more iPEM layers. The layer(s) can be disposed on at least a portion of an exterior surface of or all of an exterior surface of or all exterior surfaces of a substrate. The layer(s) can be planar or non-planar (e.g., disposed on or take the form of a non-planar substrate). The layer(s) can be continuous or discontinuous. In certain examples, the disclosure includes iPEMs coated onto substrates such as, for example, nanoparticles, microparticles, viable prokaryotic or eukaryotic cells such as erythrocytes or antigen presenting cells, hematopoietic stem cells, and T cells, or viral particles, or macroscopic articles such as microscope slides, scaffolds (e.g., vaccine scaffolds), medical implants, microneedles, implantable devices, and other biomedical devices.

In general, compositions of this disclosure comprise, consist essentially of or consist of: a) a first layer of a first immune signal compound (that may be disposed on a substrate); b) a second layer of the first immune signal compound or a second immune signal compound disposed on the first layer of the first immune signal; where the immune signal compounds are selected from peptides, proteins, nucleic acids, and charged derivatives and combinations thereof, and where the first immune signal compound and the second immune signal compound have one or more oppositely charged domains. By "oppositely charged domain" it is meant that the compound(s) in the first layer comprise a charged moiety or a series of charged moieties (a domain) that imparts or collectively impart, respectively, either a negative or positive charge to the domain, and the compounds in the second layer comprise a charged moiety or a series of charged moieties (also a domain) that imparts or collectively impart, respectively, a charge that is opposite the charge of the compounds in the first layer. The disclosure accordingly provides in certain approaches polyelectrolyte multilayer (PEM) coatings built entirely from immune signals, referred to herein as immune-PEMs (iPEMs). Immune signal compounds are also referred to herein as immune signals.

A substrate can be a sacrificial substrate. For example, a sacrificial substrate can be used to form a capsule (e.g., after removal of the sacrificial substrate). A sacrificial substrate can be removed (e.g., removed such that no detectable sacrificial substrate material remains) leaving iPEM(s) having substantially the shape of the sacrificial substrate. For example, a sacrificial substrate is removed by dissolution, chemical decomposition, or lysing (e.g., with a hypotonic solution). Examples of suitable sacrificial substrates include substrates formed from carbonate salts (e.g., calcium carbonate, magnesium carbonate, cadmium carbonate), melamine formaldehyde, silicon dioxide, and cells, including prokaryotic and eukaryotic cells, and macroscopic substrates (e.g., microscope slides, implantable devices). These substrates may range in size from 1 nm or less to objects with dimensions on the order of centimeters or more. The length, width, and/or diameter can range from tens of nanometers to several millimeters.

A substrate can be a non-sacrificial substrate. Examples of suitable non-sacrificial substrates include, but are not limited to, nanoparticles, microparticles, viable prokaryotic or eukaryotic cells, such as erythrocytes or antigen presenting cells, and viral particles. Additional examples of suitable non-sacrificial substrates include, but are not limited to, macroscopic articles such as microscope slides, scaffolds (e.g., vaccine scaffolds), medical implants, and biomedical devices. For example, the non-sacrificial substrate can be an implantable device. In certain examples, the non-sacrificial substrate is a metal core substrate or an immunologically inert polymer particle substrate.

In an approach, the iPEMs are coated onto an array substrate, such as a needle array substrate. In an example, the iPEMs are coated onto microneedle substrates. Microneedle systems for drug delivery are known in the art. Thus the disclosure is useful for intradermal and/or transdermal delivery by adapting available microneedle systems such that they are coated with the iPEMs.

Individual iPEM layers can have a range of sizes. For example, each individual layer in a composition can have a thickness of 10 nm to 1000 nm, including all integer nm values and ranges there between.

A composition can have various numbers of iPEM layers. For example, a composition can have 1 to 40 iPEM layers (e.g., discrete iPEM layers), including all integer numbers of layers and ranges there between. For example, a capsule (without a substrate or with a substrate (e.g., a disposable or non-disposable substrate) can comprise 1 to 10 or 6 to 10 individual iPEM layers.

An iPEM layer disposed on a substrate and the substrate have opposite charge and/or adjacent layers of the composition have opposite charge. For example, an iPEM layer disposed on a substrate and the substrate each comprise one or more oppositely charged domains and/or adjacent layers of the composition each comprise one or more oppositely charged domains.

The composition (e.g., iPEM layers) can encompasses a three-dimensional void. Such a composition can be made by removal of a sacrificial substrate. An immune signal compound and/or a drug (e.g., an immunosuppressant such as, for example, mTOR inhibitors, mycophenolic acid, Stat3 inhibitors) can be sequestered in the three-dimensional void.

A wide variety of immune signals can be used (e.g., to form iPEMs). iPEMS of this disclosure can be provided alone, or in physical association with a substrate, with the proviso that any substrate that modulates adaptive immunity, and/or promotes inflammation, can be excluded as the substrate. The immune signal compounds can be selected from peptides, proteins, nucleic acids, and charged derivatives thereof.

When the immune signal in an iPEM of this disclosure is an antigen, the antigen may any antigen for which modulating an adaptive immune response would be desirable. In general, peptides and polypeptides used in the iPEMs of this disclosure as antigens will comprise epitopes that are 8-30 amino acids in length. However, it is not expected that there is any maximum size of the antigen-containing component. Further, the stoichiometry/ratio of each component is tunable by altering the assembly conditions through relative concentration of each component, ionic strength, pH, or other physicochemical parameters that will be apparent to those skilled in the art, given the benefit of the present disclosure. When the iPEMs are designed to enhance an immune response, examples of antigens that can be an immune signal in the iPEM include but are not limited to antigens expressed by, for example, cancer cells, or pathogenic organisms. For antigens expressed by pathogenic agents, non-limiting examples of such agents include viruses, bacteria, fungi, protozoans, or any other parasite or otherwise infectious agent. In certain approaches the antigen expressed by pathogenic prokaryotic bacteria, such as a pathogenic Gram-negative, or Gram positive bacteria. In certain examples, the antigen is expressed by a pathogenic strain of E. coli, V. cholerae, P. aeruginosa, B. burgdorferi, Streptococcus spp., S. typhimurium, S. aureus, E. faecalis, A. baumannii, A. iwoffii, S. marcescens, P. mirabilis, K. pneumoniae, A. calcoaceticus, S. mutans, P. gingivalis, H. influenza, H. pylori, N. meningitides, N. gonorrhea, M. kansasii, B. anthracis, P. acnes, C. tetani, C. trachomatis, L. pneumophila, Y. pestis, B. abortus, F. tularensis, C. difficile, or V. harveyi. In certain examples, the antigen is a component of a virus, including but not necessarily limited to single or double-stranded RNA and DNA viruses. Non-limiting examples of pathogenic viruses include all types of pathogenic adenovirus, herpes virus, papilloma virus, pox virus, parvovirus, Caliciviridae, hepatitis virus, retrovirus, paramyxovirus, and rhabdovirus.

The immune signal of an iPEM can be a cancer antigen. The cancer antigen may be any peptide or polypeptide antigen expressed by any cancer cell. In certain examples, expression of the antigen is specific to cancer cells, and/or the antigen is overexpressed by cancer cells relative to non-cancer cells. In examples the cancer cell antigen may be expressed by a type of cancer that includes but is not necessarily limited to fibrosarcoma, myxosarcoma, liposarcoma, chondrosarcoma, osteogenic sarcoma, chordoma, angiosarcoma, endotheliosarcoma, lymphangiosarcoma, pseudomyxoma peritonei, lymphangioendotheliosarcoma, synovioma, mesothelioma, Ewing's tumor, leiomyosarcoma, rhabdomyosarcoma, colon carcinoma, pancreatic cancer, breast cancer, ovarian cancer, prostate cancer, squamous cell carcinoma, basal cell carcinoma, adenocarcinoma, head and neck cancer, liver cancer, sweat gland carcinoma, sebaceous gland carcinoma, papillary carcinoma, papillary adenocarcinomas, cystadenocarcinoma, medullary carcinoma, bronchogenic carcinoma, renal cell carcinoma, hepatoma, bile duct carcinoma, choriocarcinoma, seminoma, embryonal carcinoma, Wilns' tumor, cervical cancer, testicular tumor, lung carcinoma, small cell lung carcinoma, bladder carcinoma, epithelial carcinoma, glioma, astrocytoma, medulloblastoma, craniopharyngioma, ependymoma, pinealoma, hemangioblastoma, acoustic neuroma, oliodendroglioma, meningioma, melanoma, neuroblastoma, retinoblastoma, leukemia, lymphoma, multiple myeloma, thymoma, Waldenstrom's macroglobulinemia, and heavy chain disease.

In specific examples, the cancer antigen is selected from NY-ESO-1 antigen, survivin, melanoma antigen (i.e., MAGE 1, MAGE 3, MART-1, tyrosinase, gp100), or High Molecular Weight-Melanoma Associated Antigen (HMW-MAA), Alphafetoprotein (AFP), Carcinoembryonic antigen (CEA), CA-125, and Epithelial tumor antigen (ETA). Specific and non-limiting examples of cancer antigens include Mgp100 (EGSRNQDWL (SEQ ID NO:14)); Mgp100 long (AVGALEGPRNQDWLGVPRQL (SEQ ID NO:1)); Hgp100 (KVPRNQDW (SEQ ID NO:2)); Trp2 (SVYDFFVWL (SEQ ID NO:3)); Trp1 (TAPDNLGYA (SEQ ID NO:4)); Trp1 high affinity (TAPDNLGYM (SEQ ID NO:5)); and any immunogenic segment of survivin, such as WEP (WEPDDNPI (SEQ ID NO:6)) and EEL (EELTVSEFL (SEQ ID NO:7)).

When the iPEMs of this disclosure are designed to suppress an immune response, i.e., induce tolerance to an immune signal, such as self-antigens, examples of self-antigens that can be an immune signal in the iPEMs include but are not limited to autoantigens, meaning antigens endogenously expressed by an individual, but to which an undesirable auto-immune response is developed. Non-limiting examples of disorders that are known or are believed to be caused at least in part by autoantigens include systemic autoimmune diseases, such as all forms of multiple sclerosis, Lupus erythematosus, Sjögren's syndrome, sarcoidosis, scleroderma, rheumatoid arthritis, cryoglobulinemic vasculitis, and dermatomyositis. The disclosure also includes immune signals that are antigens associated with autoimmunity in localized autoimmune disorders, examples of which include but are not limited to Diabetes mellitus type 1, Hashimoto's thyroiditis, Addison's disease, Coeliac disease, Crohn's Disease, Pernicious anaemia, Pemphigus vulgaris, Vitiligo, Autoimmune haemolytic anaemia, Idiopathic thrombocytopenic purpura, and Myasthenia gravis. In certain approaches the immune signal component comprises a peptide or polypeptide expressed by insulin-producing beta cells in the pancreas, i.e., beta cell islet antigens, for use in treating diabetes. In certain examples, the immune signal comprises all or a fragment of insulin, or the 65-kDa isoform of glutamic acid decarboxylase (GAD), or the phosphatase-related IA-2 molecule, or zinc transporter (ZnT8), chromogranin, or chromatin.

The disclosure includes inducing tolerance to agents that can induce an allergic response. Thus, iPEMs of this disclosure can comprise an immune signal that is an antigen which comprises or consists of all or a component of an allergen. Allergic conditions for which the compositions and methods of the present disclosure may provide a benefit include but are not necessarily limited to food allergies, such as nut and fish allergies. In examples, the disclosure pertains to inhibiting or lessening the severity of, for instance, Type I hypersensitivity reactions and/or late phase allergic responses. Non-limiting examples of such allergic reactions for which the present disclosure can provide a prophylactic and/or therapeutic benefit include allergic rhinitis, food allergies, asthma and related airway inflammatory conditions, and allergic reactions caused by for example, envenomation or medications. Specific allergens include but are not limited to allergenic peptides and polypeptides included in foods such as peanuts, tree nuts, milk, egg, wheat, soy, fish and shellfish. Other animal products comprising allergens to which tolerance may be induced according to this disclosure include but are not limited to peptides and polypeptides in pet dander, such as from dogs and domesticated cats, and components of venom, such as those present in spider, reptile or bee venom.

Various examples of this disclosure are demonstrated using myelin antigens. Thus, the iPEMs can be fully or partially myelin-based agents. For inducing tolerance to myelin, such as in MS, it is expected that any peptide or polypeptide myelin component can be used, provided it contains a myelin antigen that is specifically recognized in whole or in part by a component of the immune system of the individual in need of treatment. Those skilled in the art will recognize that myelin is synthesized by different cell types, and can vary in composition and structure, but is defined as the material that makes up the so-called sheath of myelinated axons in vertebrates. Myelin in its form in myelinated axons comprises about 40% water; its dry mass is approximately 70-85% lipids and 15-30% proteins. In general, and without intending to be limited by any particular theory, it is considered that myelin proteins or fragments thereof that are inappropriately recognized by the immune system of an individual in need of treatment can function as a suitable antigen in the compositions and methods of the present disclosure. In examples, the myelin antigen comprises all or a fragment of myelin basic protein (MBP), myelin oligodendrocyte glycoprotein (MOG), or proteolipid protein. In certain examples, immunogenic fragments of myelin are considered to be those that are recognized by the immune system of an individual who has MS. In certain examples, the iPEMs may comprise myelin oligodendrocyte glycoprotein, MOG-35-55, MEVGWYRSPFSRVVH-LYRNGK (SEQ ID NO:8); proteolipoprotein, PLP139-151, HSLGKWLGHPDKF (SEQ ID NO:9) or PLP178-191, NTWTTCQSIAFPSK (SEQ ID NO:10); and myelin basic protein, MBP84-104-, VHFFKNIVTPRTPPPSQGKGR (SEQ ID NO:11). Similarly, myelin peptide fragments: MOG1-20, MOG35-55, MBP13-32, MBP83-99, MBP111-129, MBP146-170, and PLP139-154 constitute non-limiting examples of antigen immune signals that can be used in aspects of this disclosure.

The antigens of the disclosure as one of the immune signals can be combined with another immune signal (i.e., and non-antigen signal) in the iPEMs. The other immune signal may dictate whether the modulation of the adaptive immune system comprises stimulating the immune response against the antigen, or comprises inducing tolerance to the antigen.

In certain approaches the other immune signal may be a peptide, polypeptide or polynucleotide. In certain approaches the other immune signal can bind to a pattern recognition receptor on an immune cell, such as a Toll-like-receptor (TLR), such as TLR1, TLR2, TLR3, TLR4, TLR5, TLR6, TLR7, TLR8, TLR9, TLR10, and TLR11. The TLR ligand may be a TLR agonist or antagonistic ligand. In examples, such as for inducing tolerance, the immune signal is a TLR antagonist, whereas for stimulating an immune response the TLR ligand can be a TLR agonist. Accordingly, in certain approaches an immune signal of in iPEM of this disclosure comprises a modified or unmodified polynucleotide. When a component of an iPEM of this disclosure is a polynucleotide, it may be an RNA polynucleotide, a DNA polynucleotide, or a DNA/RNA hybrid. The polynucleotides may be single stranded, double stranded, linear, circular, or branched. The polynucleotide may be a ribozyme, such as a hammerhead ribozyme, an antisense RNA, an siRNA, a DNAzyme, a hairpin ribozyme, or any modified or unmodified polynucleotide. The polynucleotide agent may include modified nucleotides and/or modified nucleotide linkages so as to increase the stability of the polynucleotide. Suitable modifications and methods for making them are well known in the art. Some examples of modified polynucleotide agents for use in the present disclosure include but are not limited to polynucleotides which comprise modified ribonucleotides or deoxyribonucleotides. For example, modified ribonucleotides may comprise substitutions of the 2' position of the ribose moiety with an —O-lower alkyl group containing 1-6 saturated or unsaturated carbon atoms, or with an —O-aryl group having 2-6 carbon atoms, wherein such alkyl or aryl group may be unsubstituted or may be substituted, e.g., with halo, hydroxy, trifluoromethyl, cyano, nitro, acyl, acyloxy, alkoxy, carboxyl, carbalkoxyl, or amino groups; or with a hydroxy, an amino or a halo group. The nucleotides may be linked by phosphodiester linkages or by a synthetic linkage, i.e., a linkage other than a phosphodiester linkage. Examples of inter-nucleoside linkages in the polynucleotide agents that can be used in the disclosure include, but are not limited to, phosphodiester, alkylphosphonate, phosphorothioate, phosphorodithioate, phosphate ester, alkylphosphonothioate, phosphoramidate, carbamate, carbonate, morpholino, phosphate trister, acetamidate, carboxymethyl ester, or combinations thereof.

In an example, the other immune signal may be an siRNA for use in RNA interference (RNAi) mediated silencing or downregulation of a target mRNA. RNAi agents are commonly expressed in cells as short hairpin RNAs (shRNA). shRNA is an RNA molecule that contains a sense strand, antisense strand, and a short loop sequence between the sense and antisense fragments. shRNA is exported into the cytoplasm where it is processed by dicer into short interfering RNA (siRNA). siRNA are 21-23 nucleotide double-stranded RNA molecules that are recognized by the RNA-induced silencing complex (RISC). Once incorporated into RISC, siRNA facilitate cleavage and degradation of targeted mRNA. Thus, for use in RNAi mediated silencing or downregulation of a target RNA, the polynucleotide component may be either an siRNA or an shRNA. Non-limiting examples comprise siRNA or shRNA targeting STAT3 to enhance immunogenicity to a target antigen, or targeting a TLR receptor gene (e.g., MyD88) for tolerogenic applications.

The polynucleotide immune signal may or may not encode a protein. The polynucleotide may comprise an expression vector, such as a plasmid, and therefore may be capable of programming a cell into which the iPEM is introduced to make any particular protein. In this regard, we have made and tested iPEMs using antigens, such as MOG, and a variety of commercially available plasmids, including pUNO1-mIL10, available from INVIVOGEN, which expresses murine Interleukin-10, and pUNO1-mTGFB2, also available from available from INVIVOGEN, which is an expression vector that expresses murine TGFB2. We have incorporated more than two dozen distinct plasmids into the multilayer structures for both reporting function (e.g., EGFP) and for function (e.g., plasmids encoding tumor antigen or cytokines). The polynucleotide may accordingly encode any immunomodulatory polypeptide, examples of which include but are not limited to cytokines, interleukins, transcription factors, etc. In one embodiment the polynucleotide encodes TGF-Beta. The polynucleotide, when in the form of an expression vector, may comprise any of various and well known components so that the vector can be propagated in suitable cell culture, and so that it will express a protein of interest when introduced into a suitable cell. In general the expression vector will comprise elements suitable to promote expression of at least one encoded polypeptide in mammalian cells. The expression vector can thus comprise at least one promoter that is operatively linked to a protein coding region, such as an inducible or constitutive promoter, strong promoters, etc., suitable origins of replication, polycloning sites, translation initiation sequence, transcription termination sites, polyadenylation sites, enhancer elements, selectable markers, detectable markers (i.e., reporter molecules, including but not limited to fluorescent proteins), and may provide for expression of one or more polypeptides, fusion proteins, and may comprises mono- or polycistronic reading frames, internal ribosome entry sites, linker sequences, cleavable tags, etc. The vector may encode degradable peptide spacers (e.g. AAY) to encourage processing of epitopes into an MHC or HLA compatible form (e.g. SVYDFFVWL AAY SVYDFFVWL AAY SVYDFFVWL (SEQ ID NO:12)) and may further encode amino acid sequences to encourage further antigen processing, such as for ubiquination. The expression vector may be of any suitable form and size. As an alternative to an expression vector, mRNA encoding any amino acid sequence can be included, such as tumor antigens to facilitate expression and processing of tumor antigens.

In certain approaches, an immune signal that is a component of the iPEMs of this disclosure comprises a ligand for a toll-like receptor, such as CpG oligodeoxynucleotides ligands. CpG oligonucleotides are well known in the art as short single-stranded synthetic DNA molecules that contain a cytosine triphosphate deoxynucleotide ("C") followed by a guanine triphosphate deoxynucleotide ("G"). While the "p" designates the phosphodiester bond between consecutive nucleotides the present disclosure, as discussed herein, includes modified linkages, and thus CpG includes such modifications. As is known in the art, unmethylated CpG polynucleotides are considered pathogen-associated molecular patterns (PAMPs) because of their presence in many microbial genomes, but are rare in vertebrate genomes. TLR ligand are commercially available and can be adapted for use in the present disclosure, such as from INVIVOGEN (see, for example, www.invivogen.com/tlr9-antagonist). Thus, the disclosure comprises CpG oligodeoxynucleotides (ODNs), which can activate the innate immune system to produce proinflammatory cytokines. A non-limiting example of a suitable CpG TLR9 antagonist is TGACTGTGAAGGTTAGAGATGA (SEQ ID NO:13). In another non-limiting example the disclosure includes as an immune signal Polyinosinic-polycytidylic acid (polyIC). PolyIC is a synthetic analog of double-stranded RNA (dsRNA), a molecular pattern associated with viral infection. It is recognized by TLR3 and induces activation of NF-kB and production of cytokines.

As discussed above, in certain examples, the iPEMs of the present disclosure can comprise as cancer antigens any one or combinations of the following non-limiting amino acid sequences: Mgp100 (EGSRNQDWL (SEQ ID NO:14)); Mgp100 long (AVGALEGPRNQDWLGVPRQL (SEQ ID NO:1)); Hgp100 (KVPRNQDW (SEQ ID NO:2)); Trp2 (SVYDFFVWL (SEQ ID NO:3); Trp1 (TAPDNLGYA (SEQ ID NO:4)); Trp1 high affinity (TAPDNLGYM (SEQ ID NO:5)); and any immunogenic segment of survivin, such as WEP (WEPDDNPI (SEQ ID NO:6) and EEL (EELTVSEFL (SEQ ID NO:7). In certain examples the disclosure is illustrated using the model Ovalbumin peptide SIINFEKL (SEQ ID NO:15) (referred to in certain instances as "SIIN"). In demonstrating various aspects of this disclosure, we have tested in animal disease models iPEMs consisting of the following immune signals for stimulating an adaptive immune response (where R signifies arginine and D signifies aspartic acid) against cancer: SIINR9/polyIC; SIINR9/CpG; hgp100/polyIC; Hgp100/CpG, and to induce tolerance: MOG-R3/GpG; MOG-R3/CTRL ODN; MOG-R1/GpG; and MOG-R9/GpG.

We have determined that substituting polyIC with CpG enhances the desired effect on adaptive immunity. For example, using hgp100 as an antigen, we observed expansion of gp100-specific CD8+ T cells, and functional anti-tumor immunity that delays and in certain cases prevents tumors formation in mouse models.

An immune signal can be inherently charged, or modified to form charged compound (e.g., a charged immune signal derivative). The description of the addition of arginine and aspartic acid represents that the presently provided iPEM components are in certain aspects modified relative to their naturally occurring counterparts. Further, the addition of these amino acids illustrates the principle that any essentially any immune signal for use in iPEMs as described herein can be modified such that it comprises a domain having a positive, or negative charge. Thus, in an approach, adding charged amino acids to an immune signal yields a charged domain. Adding oppositely charged amino acids to another immune signal yields an oppositely charged domain, and thus the signals are rendered amendable to be layered such that they are held together electrostatically. Those skilled in the art will recognize that the charge can be affected by, for example, pH. In certain examples the iPEMs are assembled at a first pH, such that they can disassemble at physiologic pH. Those skilled in the art will also recognize that certain immune signals may have an endogenous charge, and therefore do not require modification to be incorporated into iPEM layers. In general, negatively charged domains can be incorporated into any particular immune signal by adding one or more glutamates or aspartates, while positively charged domains can be introduced by adding one or more arginines or lysines. Histidines may also be used. Those skilled in the art will recognize that polynucleotides are generally negatively charged due to their phosphate groups, and thus may comprise an immune signal with a negatively charged domain that is comprised by the entire phosphate backbone. Modifications with amino acid residues can be of any length. Generally, peptides which will be processed by immune cells range from 1-9 residue modifications. iPEMs may also be assembled entirely from peptides with identical or different sequences, but modified with oppositely charged amino acid residues Compositions comprising iPEMs of this disclosure can be provided in pharmaceutical formulations. Accordingly, in an example, a pharmaceutical composition comprises on or more compositions comprising one or more iPEMs and one or more inactive ingredient.

The form of pharmaceutical preparation is not particularly limited, but generally can comprise the iPEMs and at least one inactive ingredient. In certain examples suitable pharmaceutical compositions can be prepared by mixing any one or combination of the iPEMs with an inactive ingredient. Examples of suitable inactive ingredients include, but are not limited to, pharmaceutically-acceptable carrier, diluent or excipient, and suitable such components are well known in the art. Some examples of such carriers, diluents and excipients can be found in: Remington: The Science and Practice of Pharmacy (2005) 21st Edition, Philadelphia, Pa. Lippincott Williams & Wilkins.

In certain aspects, the present disclosure provides methods of making compositions of the present disclosure. For example, the compositions are made by a method of the present disclosure.

In certain approaches, coating a substrate comprises repeated dipping of the substrate in a solution comprising a first immune signal having a first charge, dipping the substrate into a second solution comprising the first or a second immune signal having a second charge, and so forth. In other approaches, the disclosure comprises extruding the one or both immune signals, electrospinning, molding, forming a film, fiber, ribbon or tube, and forming a film, such as forming a film on patterned or shaped surface, provided distinct immune signals are held together in the iPEM via their oppositely charged domains. The iPEM formation steps (e.g., dipping or extrusion steps) can be repeated to form a desired number of iPEMs.

Compositions of this disclosure can be made via processes that are completely aqueous. The disclosure therefore includes the proviso that the compositions can be assembled without using any non-aqueous solvents. In certain approaches methods of making compositions of the disclosure are performed without changing temperature, and thus can exclude heating and/or cooling during formation of the compositions. In general, the compositions of the disclosure are performed without any mixing step, but both mixing and temperature control can be used to fine tune iPEM properties such as size and stability if desired.

In certain approaches, the present disclosure relates to methods of modulating an immune system of an individual using one or more compositions of the present disclosure. In certain examples, the modulating comprises stimulating an adaptive immune response against one or more antigens. An "adaptive immune response" as used herein means an antigen-specific immune response. The disclosure comprises in various approaches modulating on or more adaptive immune responses such that a therapeutic and/or a prophylactic response against an antigen is elicited, or tolerance to an antigen is induced.

Administration of compositions of this disclosure can be made taking into account such factors as the molecular makeup of the antigen, the size and age of the individual to be treated, and the type and stage of a disease with which the individual may be suspected of having or may have been diagnosed with. The compositions and/or methods of the disclosure may be used to elicit an enhanced immune response that is prophylactic or therapeutic, and/or may be tolerogenic. The individual to whom the composition is administered can be an individual in need of the treatment, and/or an individual who has been diagnosed with, is suspected of having, or is at risk for developing a disease or other disorder that is associated with expression of the antigen, and/or is associated with an undesirable immune response to the antigen, such as in the case of autoimmune disorders.

Thus, the amount of iPEMs to be included in a composition of the disclosure and/or to be used in the method of the disclosure can be determined by those skilled in the art, given the benefit of the present disclosure. Thus, in an example, an effective amount of a composition of the disclosure is administered. An effective amount can be an amount of the composition that inhibits growth of cells in the individual that express the antigen, such as cancer cells, or the cells of a pathogenic organism, or an amount that extends the survival of the individual, or that alleviates disease symptoms associated with expression of the antigen in the individual, or stimulates a tolerogenic effect towards the antigen, and combinations thereof.

In addition to intra- and trans-dermal approaches, iPEMs and/or compositions comprising them can be administered to an individual in need thereof using any available method and route, including oral, mucosal, intracranial, parenteral, subcutaneous, intraperitoneal, intrapulmonary, intranasal and intracranial injections. Parenteral infusions include intramuscular, intravenous, intraarterial, intraperitoneal, and subcutaneous administration. In an approach, a composition of this disclosure is introduced into an individual via direct intra-lymph node administration. Methods for direct intra-lymph node administration are known in the art. In certain examples, administration is achieved using ultrasound guidance to inject the formulation into the lymph node. Those skilled in the art, given the benefit of the present disclosure, will recognize how to formulate an effective amount of iPEMs to administer based on such factors as the type of disorder or condition for which the individual is need of prophylaxis and/or treatment, and accordingly the type of immune response desired. Dosing determinations can include but are not limited to considering the size, age, and gender of the individual, stage of the disease and/or risk of its manifestation or progression or recurrence, and personal medical history of the individual.

The methods of the disclosure can be performed in conjunction with conventional therapies that are intended to treat a disease or disorder associated with the antigen. For example, if the method is used to enhance an immune response to a tumor antigen in an individual, treatment modalities including but not limited to chemotherapies, surgical interventions, and radiation therapy can be performed prior to, concurrently, or subsequent to the method of the disclosure. If the disclosure is intended to enhance an immune response to an antigen expressed by a pathogen, it can be performed in conjunction with conventional anti-microbial/ant-viral approaches, such as by administering antibiotics and other anti-pathogen treatments.

If the method of the disclosure is used to induce tolerance to an antigen, it can be performed in conjunction with conventional therapies that are intended to reduce the immune response to the antigen, include but not necessarily limited to administering the compositions with agents such as anti-inflammatory agents, including but not necessarily limited to non-steroidal anti-inflammatory agents (NSAIDs), or steroidal compositions, or other agents that may enhance the function of the compositions of the disclosure, such tolerogenic agents. In certain examples, the disclosure comprises concurrent or sequential administration of a tolerogenic agent. In certain approaches, the tolerogenic agent can be provided in physical association with a composition of this disclosure, such as being present in a hollow area of an iPEM as described herein, such as by a hollow portion created by removal of a sacrificial core. In certain examples the tolerogenic agent comprises any inhibitor of the mammalian target of rapamycin (mTOR), also known as FK506-binding protein 12-rapamycin-associated protein 1 (FRAP1). In examples, the mTOR inhibitor is rapamycin, or a rapalog. In examples, the mTOR inhibitor comprises Sirolimus, Temsirolimus, Everolimus, Deforolimus, or a second generation mTOR inhibitor generally known to function as an ATP-competitive mTOR kinase inhibitors, and/or TORC1/mTORC2dual inhibitors. In examples, the tolerogenic agent, which may or may not be present in one of the iPEM layers of this disclosure, comprises a cytokine or a chemokine or a growth factor or an interferon or a transcription factor. In examples, other small molecule(s) can be included, examples of which include but are not limited to retinoic acid or mycophenolic acid. In examples a combination of tolerogenic agents can be used. In certain examples, the composition comprises one or a combination of IL-10, INF-gamma, INF-lambda, or transforming growth factor beta 1 (TGF-β1), or polynucleotides encoding them. In embodiments such agents can be included in a void of an iPEM.

Certain examples of this disclosure for inducing a tolerognic effect are demonstrated using a common, well-characterized model of progressive MS, Experimental Autoimmune Encephalomyelitis (EAE). This is induced in mice according known approaches, and commercially available compositions for generating the model are available, such as from Hooke Laboratories. Briefly, naïve C57BL/6J mice are immunized with an emulsion of MOG peptide and Complete Freund's Adjuvant, a potent immunostimulatory signal. Together, these signals trigger the expansion of myelin-specific CD4⁺ cells with inflammatory phenotypes (i.e., $T_H1$ and $T_H17$). Two and twenty-four hours later (two total doses), mice were administered pertussis toxin, which compromises the blood brain barrier, allowing myelin-specific CD4⁺ cells to infiltrate into the central nervous system (CNS) and attack the myelin sheath. The resultant neurodegeneration presents as progressive paralysis in the mice.

In certain tolerogenic examples the present disclosure will result in polarization of T cell development towards $T_{REGS}$ and away from $T_H17$ and $T_H1$ phenotypes in a systemic manner. In particular implementations the disclosure provides for expression of higher levels of Foxp3 by certain immune cells. In certain approaches, tolerognic approaches result in reduced secretion of inflammatory cytokines in response to encountering the particular antigen in question, and thus may result in for example, restraining systemic inflammation. In particular and non-limiting examples, tolerogenic examples of this disclosure result in an increase in antigen specific Tregs, and such Tregs may be found, for example, in lymph nodes, spleen, and the central nervous system. Those skilled in the art will recognize how such Tregs can be identified, such as by expression of CD4, CD25, and Foxp3.

In certain examples modulation of an adaptive immune response can be determined using any suitable method, cell markers, metabolic markers, and the like as will be apparent to those skilled in the art. Any result or parameter obtained using iPEMs of the present disclosure can be compared to a suitable reference. Any suitable reference can be used, and those skilled in the art will recognize suitable references given the benefit of this disclosure. In examples, the reference can be a single value or a range of values. For example, a reference can be a standardized curve or an area on a graph. The reference can comprise a positive or negative control. In examples the reference comprises a measurement made from a sample where no iPEM, or a control iPEM, or known non-iPEM composition was used. In various examples a measurement of a result can be compared to a reference to provide a qualitative or quantitative determination of the result, which may be positively or negatively correlated with iPEM administration. In certain examples, comparison to a reference can be performed by an individual skilled in immunology. In examples, practicing an example of an disclosure reduces or eliminates one or more signs or symptoms of a disorder of the immune system, including but not necessarily limited to the immune system.

The following examples are presented to illustrate the present disclosure. They are not intended to be limiting in any manner.

Example 1

This Example provides a non-limiting demonstration of iPEMs that are self-assembled on gold nanoparticle templates through stepwise electrostatic interactions between peptide antigen and polyanionic TLR agonists that serve as molecular adjuvants. As described above, iPEMs do not require solvents or mixing, offer direct control over the composition and loading of vaccine components, and can be coated on substrates at any scale. These films also do not require other structural components, eliminating the potentially confounding effects caused by the inherent immune-stimulatory characteristics of many synthetic polymers. iPEM loading on gold nanoparticle substrates is tunable, and cryoTEM reveals iPEM shells coated on gold cores. These nanoparticles are efficiently internalized by primary dendritic cells (DCs), resulting in activation, selective triggering of TLR signaling, and presentation of the antigens used to assemble iPEMs. In co-culture, iPEMs drive antigen-specific T cell proliferation and effector cytokines, but not cytokines associated with more generalized inflammation. Compared to mice treated with soluble antigen and adjuvant, iPEM immunization promotes high levels of antigen-specific CD8⁺ T cells in peripheral blood after one week. These enhancements result from increased DC activation and antigen presentation in draining lymph nodes. iPEM-immunized mice also exhibit a potent recall response after boosting, supporting the potential of iPEMs for designing well-defined vaccine coatings that provide high cargo density and eliminate synthetic film components.

Assembly and characterization of iPEM-AuNPs. To determine if PEMs could be assembled from polyIC (anionic) and SIIN (zwitterionic) or SIIN* (cationic), films were first deposited on planar silicon substrates by LbL deposition (FIG. 1A). iPEMs composed of polyIC and SIIN* grew linearly ($R^2=0.999$) at a rate of 10.1 nm/per bilayer, reaching a thickness of 43.5±2.2 nm after four bilayers (FIG. 2A). In contrast, film thickness did not increase when silicon substrates were alternatingly exposed to solutions of polyIC and SIIN using the same cargo concentrations and number of deposition cycles (FIG. 2A). Similar results were obtained during LbL deposition on quartz substrates to measure cargo loading, with a linear increase in antigen (FIG. 2B, $R^2$=0.984) and adjuvant (FIG. 2C, $R^2$=0.993) loading observed during assembly of (polyIC/SIIN*)$_4$, but not when substrates were exposed to solutions of polyIC and SIIN. Using fluorescently-labeled vaccine components (Cy5-polyIC, FITC-SIIN*), both polyIC and SIIN* could be visualized by fluorescence microscopy following removal of a portion of the film with a needle to provide contrast (FIG. 2D). These results indicate that the increased cationic charge conferred by $R_9$ facilitates linear growth of iPEMs assembled from adjuvant and peptide antigen. This general approach was next adapted to deposit iPEMs on injectable colloidal substrates for subsequent use in cell and animal studies.

Figure 2:
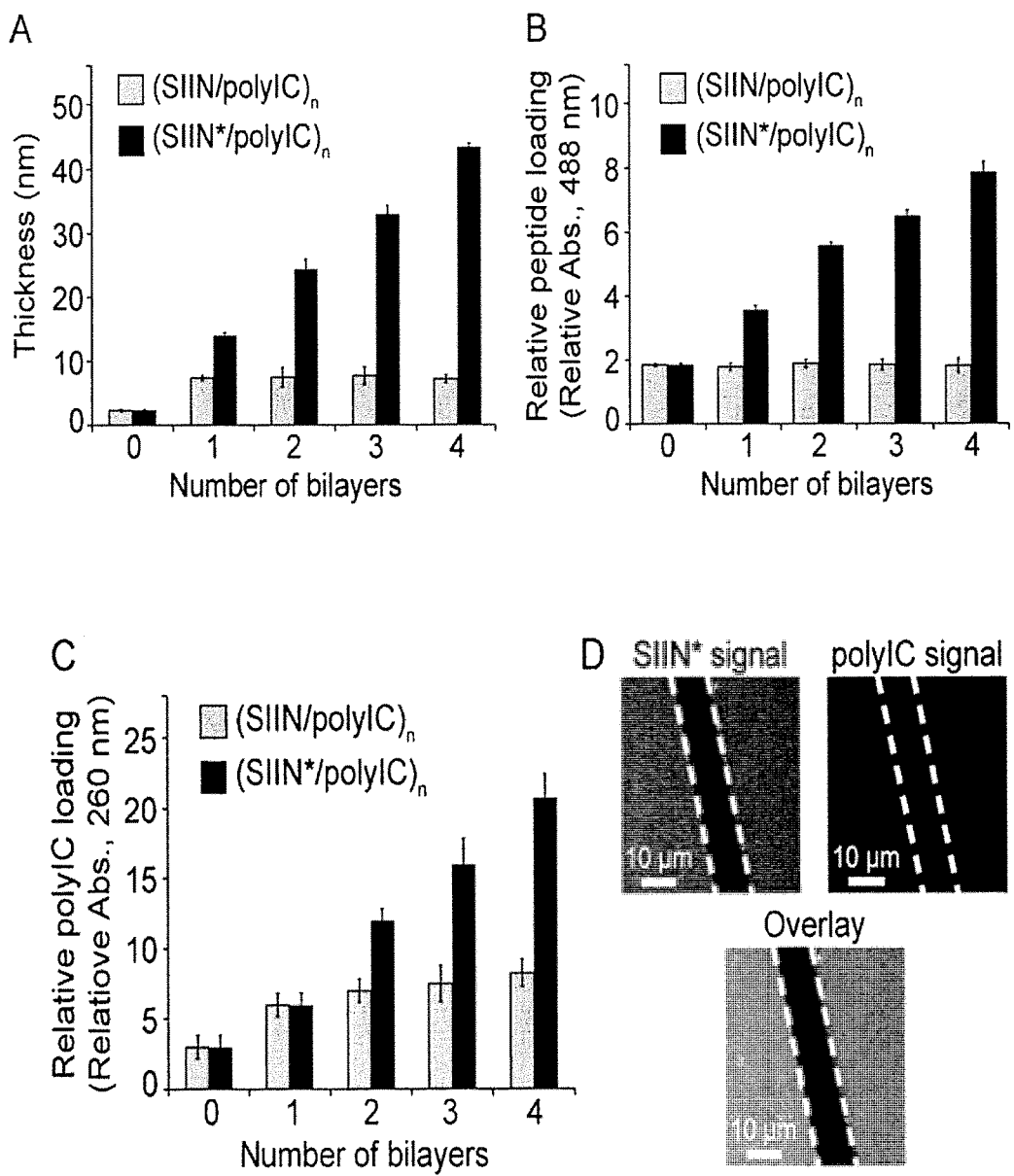
FIG. 2. iPEMs can be assembled on planar substrates with linear control over growth and loading of peptide antigens and molecular TLR agonists as adjuvants. iPEMs were assembled on quartz or silicon substrates using (polyIC/SIIN)$_n$ or (polyIC/SIIN*)$_n$ with n=0-4. (A) Thickness of iPEM films on silicon substrates measured by ellipsometry as a function of the number of layers deposited. Relative loading of (B) peptide antigen and (C) polyIC adjuvant on quartz substrates using FITC-labeled SIIN or SIIN* and Cy5-labeled polyIC. (D) Film components were visualized by fluorescence microscopy. Peptide (green signal), polyIC (red signal) and overlay (yellow signal) images are shown after removing a portion of the film with a needle to provide contrast (dashed lines).
Figure 3:
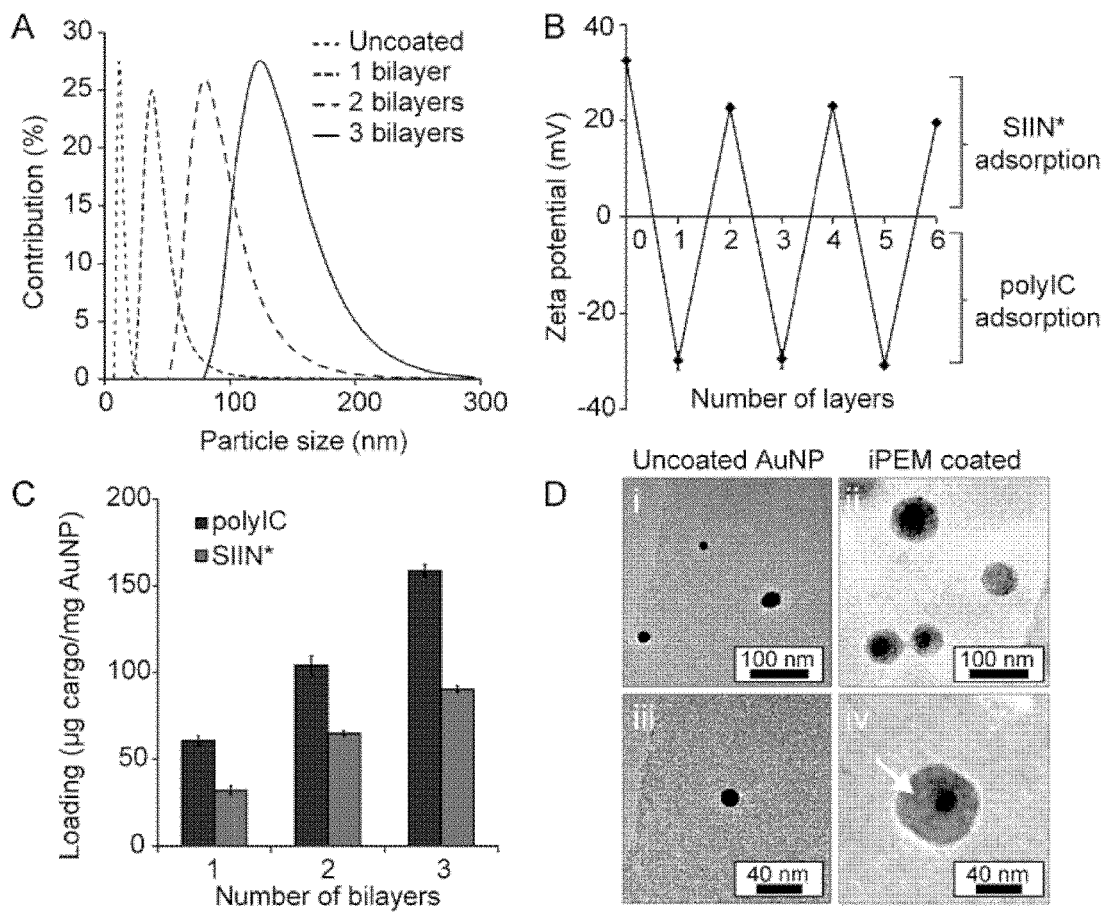
FIG. 3. iPEMs assembled on AuNP substrates provide control over vaccine cargo loading and exhibit a core-shell structure. (A) Diameter of iPEM particles measured by dynamic light scattering as a function of the number of layers deposited. (B) Inversion of zeta potential of iPEMs on AuNP as successive layers of cationic antigen and anionic adjuvant are adsorbed. (C) Linear control over the loading of peptide antigen (SIIN*) and polyIC during deposition of 3 bilayers (6 layers). (D) CryoTEM images of (i, iii) uncoated and iPEM-coated (ii, iv) AuNP cores at low (i,ii) and high (iii,iv) magnification. The arrow in (iv) indicates an iPEM shell surrounding the AuNP core.
Figure 8:
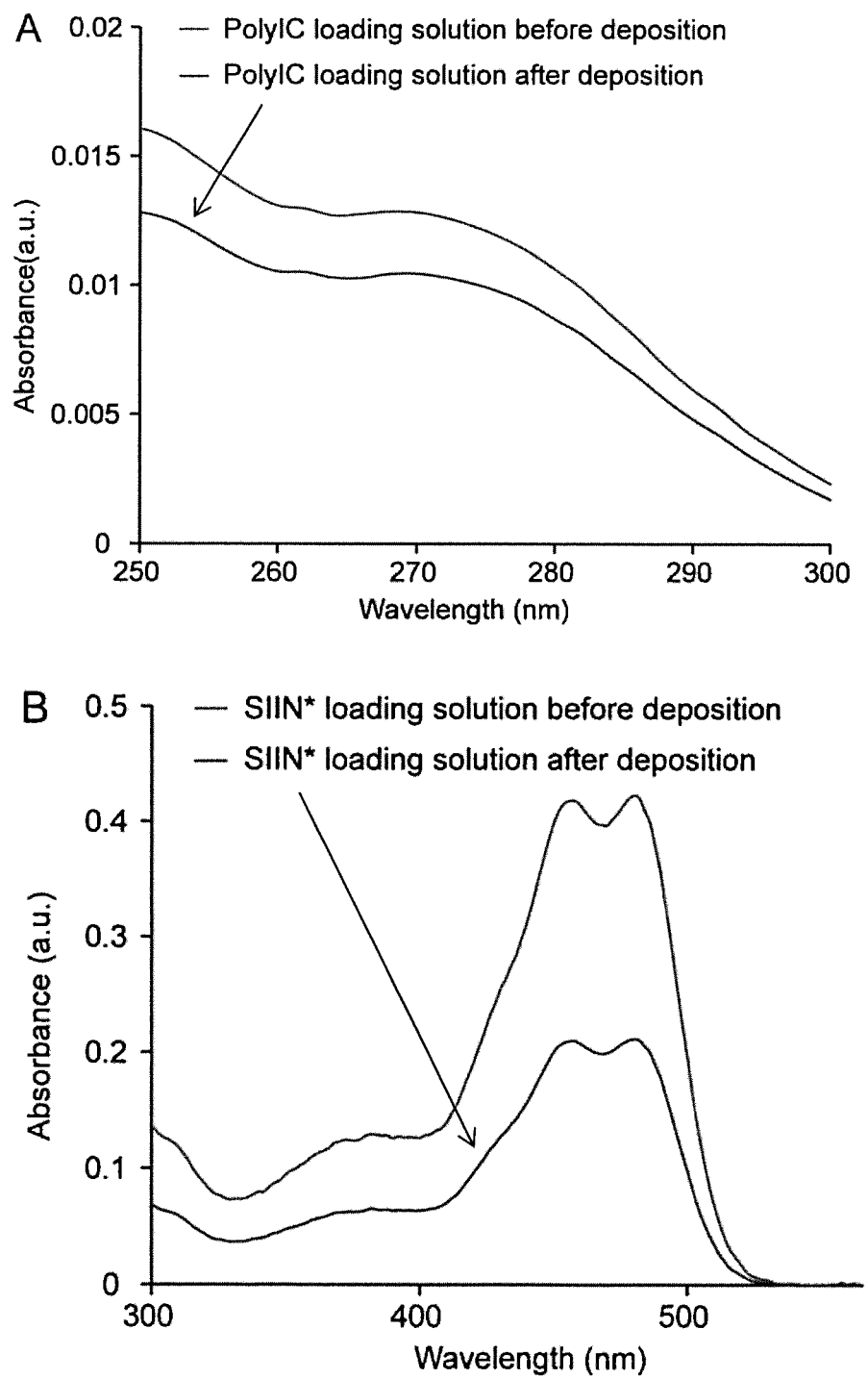
FIG. 8. UV-Vis absorbance spectra illustrating decreasing concentrations of (A) FITC-SIIN* and (B) polyIC before and after deposition of a single layer of either cargo. A fresh solution was used in depositing each layer.

To prepare iPEM-coated particles, polyIC/SIIN* films were deposited on AuNP templates as illustrated in FIG. 1B. After each exposure to polyIC or SIIN*, NPs were collected by centrifugation and washed before exposure to the next layer. The uncoated AuNP templates exhibited a diameter of 16±4 nm as confirmed by dynamic light scattering (FIG. 3A). Particle diameter increased during deposition of each successive PEM bilayer, with AuNPs-(polyIC/SIIN*)$_1$, AuNPs-(polyIC/SIIN*)$_2$, and AuNPs-(polyIC/SIIN*)$_3$ exhibiting diameters of 49±14 nm, 91±30 nm, 176±29 nm, respectively (FIG. 3A). Film growth on AuNPs was further confirmed by measuring the zeta potential, which oscillated between negative and positive values with each adsorption step of polyIC and SIIN*, respectively (FIG. 3B). The LbL nature of this growth also allowed linear control over the amounts of the immune signals coated onto the AuNPs templates. As the number of bilayers was increased from 0 to 3, polyIC loading on AuNPs reached 60.7, 104.1, and 158.8 µg/mg of AuNP, respectively, while the respective peptide loading reached 31.9, 64.9, and 90.2 µg/mg of AuNP (FIG. 3C). Over these same cycles, corresponding decreases in cargo concentration were observed in the solutions used to deposit each iPEM layer (FIG. 8).

Figure 5:
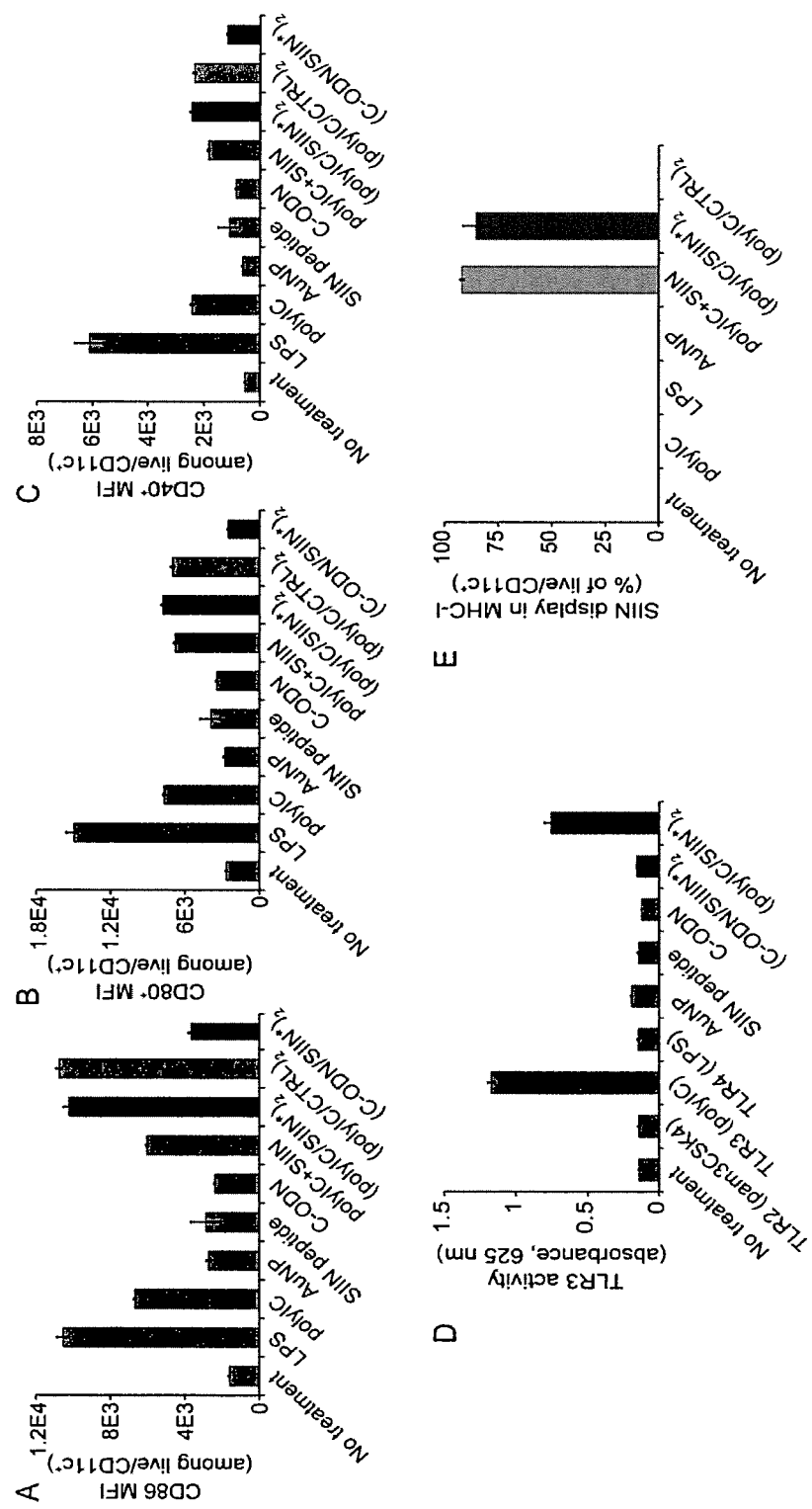
FIG. 5. iPEMs activate DCs, trigger TLR3 signaling, and promote presentation of SIIN peptide. Splenic CD11c$^+$ DCs from B6 mice were incubated for 18 hours with the indicated formulations, then flow cytometry was used to assess the expression of (A) CD86, (B) CD80, and (C) CD40. (D) TLR3 signaling in HEK-Blue TLR3 cells following a 16 hour incubation. PolyIC was included as a positive control, and TLR2 and TLR4 agonists were included as negative selectivity controls. C-ODN indicates a non-immunogenic control oligonucleotide. (E) Presentation of SIIN peptide as measured by flow cytometry following staining with an antibody that binds SIINFEKL (SEQ ID NO:15) only when presented via the MHC-I complex. For panels (A-C, E), (polyIC/CTRL)$_2$ indicates iPEMs assembled from polyIC and a control peptide that is unable to be bound by anti-SIIN/MHC-I.
Figure 9:
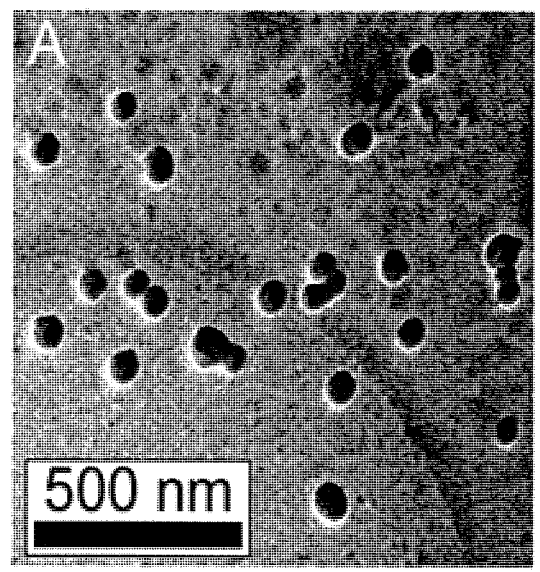
FIG. 9. Dispersion and stability of AuNP-(polyIC/SIIN*)$_2$. (A) Low magnification cryoTEM images or iPEMs coated on AuNPs. B) Mean diameter of iPEM-AuNPs during incubation in serum-free medium or serum-rich medium. Error bars indicated standard deviation of the size distribution.
Figure 9:
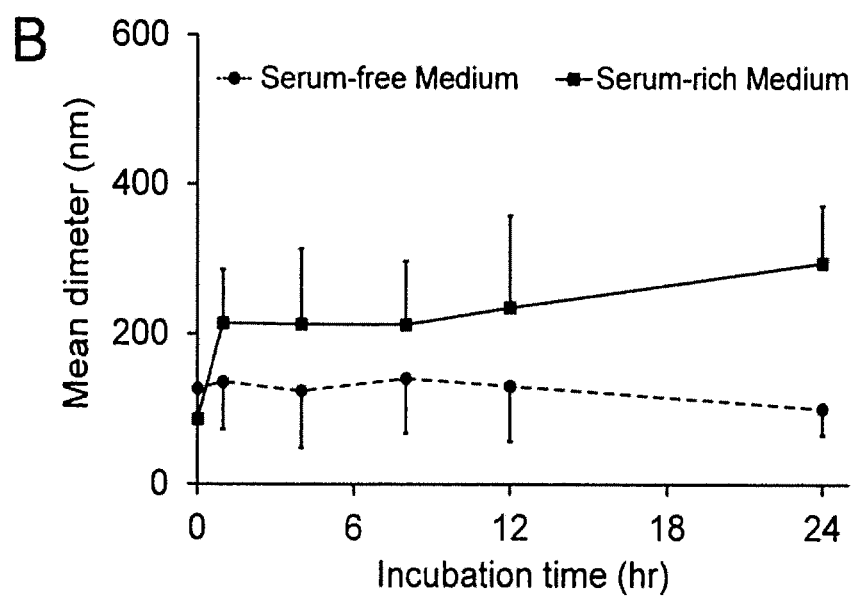
Figure 10:
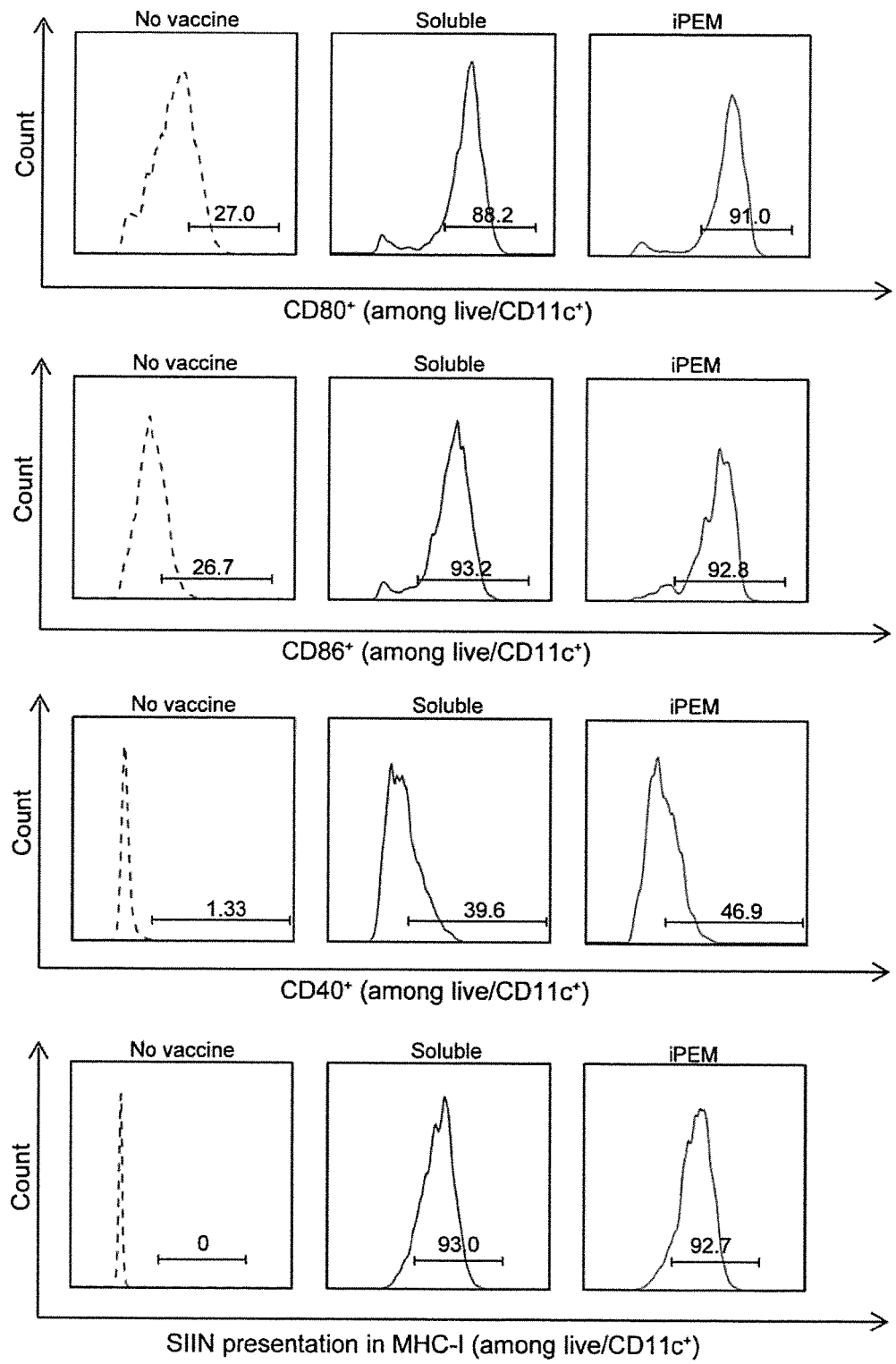
FIG. 10. Representative flow cytometry histograms demonstrating the ability of iPEMs to activate dendritic cells and drive presentation of SIIN peptide via the MHC-I pathway during ex vivo co-culture studies. These data correspond to FIG. 5A-C,E and depict the expression levels of the surface markers (A) CD80, (B) CD86, (C) CD40 and (D) SIIN presentation in MHC-I gated among live, CD11c$^+$ cells isolated from spleens of naïve B6 mice. Cells were cultured with the indicated treatments for 18 hours before analysis. iPEM structures used in these studies were AuNP-(polyIC/SIIN*)$_2$.
Figure 11:
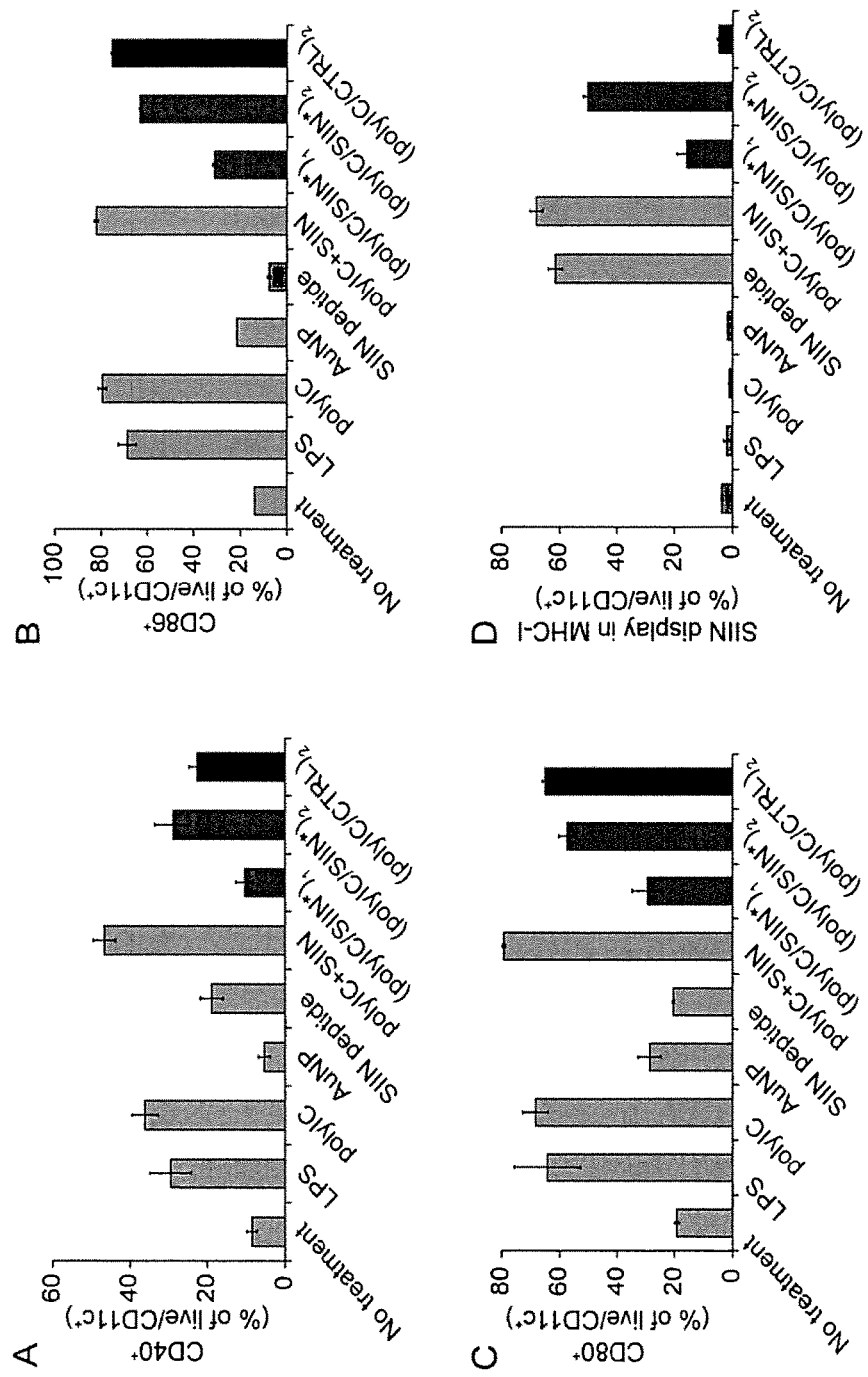
FIG. 11. DC activation and antigen presentation promoted by iPEMs can be controlled by varying the number of antigen and adjuvant layers deposited. Splenic CD11c$^+$ DCs from B6 mice were incubated for 18 hours with the iPEMs with increasing numbers of layers, or the other formulations indicated. Flow cytometry was used to assess the expression of (A) CD40, (B) CD86, and (C) CD80. (D) Presentation of SIIN peptide as measured by flow cytometry following staining with an antibody the binds SIINFEKL (SEQ ID NO:15) only when presented via the MHC-I complex. For all panels, (polyIC/CTRL)$_2$ indicates iPEMs assembled by deposition of two bilayers of polyIC and a control peptide that is not able to be bound by anti-SIIN/MHC-I.

To visualize iPEMs coated on the templates, we characterized uncoated AuNPs and AuNP-(polyIC/SIIN*)$_2$ using cryogenic transmission electronic microscopy (cryoTEM). These experiments revealed defined, spherical AuNP cores prior to coating with iPEMs (FIG. 3D-i, iii). After film deposition, iPEM particles exhibited a characteristic core-shell structure (FIG. 3D-ii,iv), with dark regions indicating AuNP cores surrounded by thicker, more diffuse iPEM shell regions (FIG. 3D-iv, arrow). While most iPEM-coated particles were individually dispersed, we observed a subset of the population clustered in groups of 2 or 3 particles (FIG. 9A). To explore particle stability and dispersion in a setting relevant to physiologic conditions, we incubated iPEM-AuNPs in serum-free medium or serum-rich medium at 37° C. Over the duration of the study (24 hours), we observed no significant changes in the sizes of particles incubated in serum-free medium, whereas particle size gradually increased to 200-300 nm over 24 hours when incubated in serum-rich medium (FIG. 9B). Together, these data indicate that iPEMs can be self-assembled on AuNPs with tunable cargo loading, and that these particles maintain sizes useful for vaccination even when incubated at elevated temperature in the presence of high concentrations of serum.

iPEM-AuNP vaccines are efficiently internalized by antigen presenting cells. We next assessed uptake of iPEM vaccine particles by treating splenic DCs (CD11c$^+$) with AuNP-(polyIC/SIIN*)$_2$ prepared from fluorescently-labeled peptide and adjuvant. Following incubation, confocal microscopy revealed high levels of peptide (green signal) and polyIC (red signal) located within cells (FIG. 4A). These signals were punctate throughout the extra-nuclear region and exhibited a high degree of co-localization between polyIC and peptide, indicating juxtaposition and co-delivery of both vaccine components. In similar studies, flow cytometry was used to quantitatively assess the interactions of iPEM-AuNPs with DCs. iPEM-coated NPs efficiently associated with DCs in a dose-dependent manner, with nearly all cells positive for both iPEM components (i.e., polyIC, SIIN*) at low dilution factors (FIG. 4B,C). Association of peptide and adjuvant in iPEM form with cells was much greater than levels observed in cells treated with equivalent doses in soluble form (FIG. 4B,C). Further, the viability of DCs treated with iPEM-coated AuNPs was 91.3% relative to cells treated with a TLR4 agonist (lipopolysaccharide, LPS). This level was statistically equivalent to the viability of DCs treated with soluble polyIC (92.8%) or a mixture of soluble polyIC and peptide (90.0%) (FIG. 4D). These results demonstrate that iPEMs assembled from polyIC and SIIN* on AuNPs are efficiently internalized by primary DCs without significant toxicity.

iPEM-AuNPs promote selective TLR signaling and efficiently activate DCs. To determine if iPEMs stimulate DC function, splenic DCs were incubated with AuNP-(polyIC/SIIN*)$_2$. Expression of classical DC activation markers and TLR3 signaling were then measured, along with presentation of SIINFEKL (SEQ ID NO:15) peptide via major histocompatibility complex I (MHC-I). DCs treated with iPEM-coated AuNPs exhibited high levels of CD40 expression that were comparable to those observed in DCs treated with soluble LPS (TLR4 agonist) or polyIC (TLR3 agonist) that served as positive controls (FIG. 5A). These levels were also similar to those observed in cells treated with equivalent, soluble doses of polyIC and SIIN. Treatment of DCs with uncoated AuNPs resulted in baseline activation levels equal to those observed in untreated DCs (FIG. 5A, 9). Analogous trends were observed in the expression levels of CD86 (FIG. 5B, 10) and CD80 (FIG. 5C, 10). For each marker, the level of activation could be increased or decreased by increasing or decreasing the number of layers—and therefore, dose—used to assemble iPEMs (FIG. 11A-11C). To test if the immunostimulatory properties of iPEMs result in part from formulation of antigen into a particulate form, AuNPs were coated with control iPEMs assembled from polyIC and a second peptide (CTRL) to form AuNP-(polyIC/CTRL)$_2$, or with SIIN* and a non-immunostimulatory control oligonucleotide (C-ODN) to form AuNP-(C-ODN/SIIN*)$_2$. For each activation marker, DCs treated with AuNP-(polyIC/CTRL)$_2$ drove DC activation levels similar to those observed in DCs treated with AuNP-(polyIC/SIIN*)$_2$ (FIG. 5A-C, orange vs. blue). In contrast, treatment with AuNP-(C-ODN/SIIN*)$_2$ did not activate DCs, as indicated by mean fluorescent intensities (MFIs) similar to the low values observed in cells treated with AuNPs or free C-ODN, or in untreated cells. Thus, the immunogenicity of iPEMs results from juxtaposition of antigens and adjuvants, not simply from formulating antigen into a particle (FIG. 5A-C; black vs. blue).

In addition to surface activation markers, treatment of DCs with iPEMs formed from polyIC and SIIN* also efficiently and specifically activated TLR3 signaling. These effects were selective to TLR3, as a lack of signal was observed in cells treated with negative controls of Pam3CSK4 (TLR2 agonist) or LPS (TLR4 agonist)—agonists recognized by TLR pathways that are activated by molecular patterns not based on the dsRNA (FIG. 5D). Importantly, activation was also specific, as TLR3 activity was not observed in cells treated with AuNPs coated with iPEMs prepared from C-ODN and SIIN* (AuNP-(ODN/SIIN*)$_2$). Together, these results demonstrate that iPEMs coated on AuNPs activate DCs without dependence on the peptide sequence incorporated into the iPEMs. Further, the incorporation of adjuvants (e.g., TLR3 agonists) into iPEMs does not impact the potency, selectivity, or specificity of these vaccine components. Similar questions of selectivity and specificity were next asked regarding the antigen component of iPEMS.

iPEM-AuNPs promote selective antigen presentation of antigens used to assemble iPEMs. To determine if antigen used to build iPEMs is processed and presented by DCs, splenic DCs were treated with AuNP-(polyIC/SIIN*)$_2$ or AuNP-(polyIC/CTRL)$_2$ as above. The cells were then stained with an antibody that binds SIINFEKL (SEQ ID NO:15) peptide when presented in the context of MHC-I—a pathway important in promoting cell-mediated immune responses against intracellular pathogens such as viruses. In these studies, 85.4%±5.9% of DCs treated with AuNP-(polyIC/SIIN*)$_2$ presented SIIN compared to 0.1±0.05% of cells treated with AuNP-(polyIC/CTRL)$_2$ (FIG. 5E). The levels of antigen presentation induced by AuNP-(polyIC/SIIN*)$_2$ were similar to those observed in cells treated with equivalent doses of soluble polyIC and SIIN (92.0±0.8%), but significantly greater than the baseline levels observed in DCs treated with uncoated AuNPs, LPS, or polyIC—none of which contained SIIN (FIG. 5E). As with activation, the degree of presentation could be controlled by changing the number of layers used to build iPEMs (FIG. 11D). Further, antigen presentation was also selective, as the frequency of SIIN presentation in DCs treated with AuNP-(polyIC/CTRL)$_2$ was equivalent to the levels observed in other samples that did not contain SIIN (FIG. 5E). Thus iPEMs deliver peptide antigens to DCs in a manner that can be efficiently processed and specifically presented through key pathways involved in cell-mediated immunity (e.g., MHC-I).

iPEM-coated AuNPs drive antigen-specific T cell proliferation and effector cytokine secretion. We next tested if DCs that process iPEMs can activate and expand T cells specific for antigens used to assemble iPEMs. DCs were treated with iPEM-coated AuNPs for 48 h, then co-cultured for 72 h with CFSE-labeled CD8$^+$ T cells (see methods) from OT-I mice—a strain in which CD8$^+$ T cell receptors are responsive to SIINFEKL (SEQ ID NO:15) peptide presented in MHC-I. T cells co-cultured with DCs treated with AuNP-(polyIC/SIIN*)$_2$ were highly proliferative (i.e., high cell division and dye dilution) compared with T cells incubated with untreated DCs, DCs treated with an irrelevant control peptide (CTRL), and DCs incubated with uncoated AuNPs (i.e., low cell division and dye dilution) (FIG. 6A). These results were indicated by decreasing CFSE levels observed in each successive T cell generation in samples treated with AuNP-(polyIC/SIIN*)$_2$, as well as positive controls that included DCs treated with soluble SIIN or a mixture of soluble SIIN and polyIC (FIG. 6A). Quantitative analysis of CFSE MFIs across all samples confirmed these trends, with AuNP-(polyIC/SIIN*)$_2$ causing low MFI values due to high levels of proliferation, and samples with cells that did not proliferate exhibiting high MFI values for CFSE (FIG. 6B). These findings were also reflected in frequency data (FIG. 6C) evaluated using the gates shown in FIG. 6A.

Figure 6:
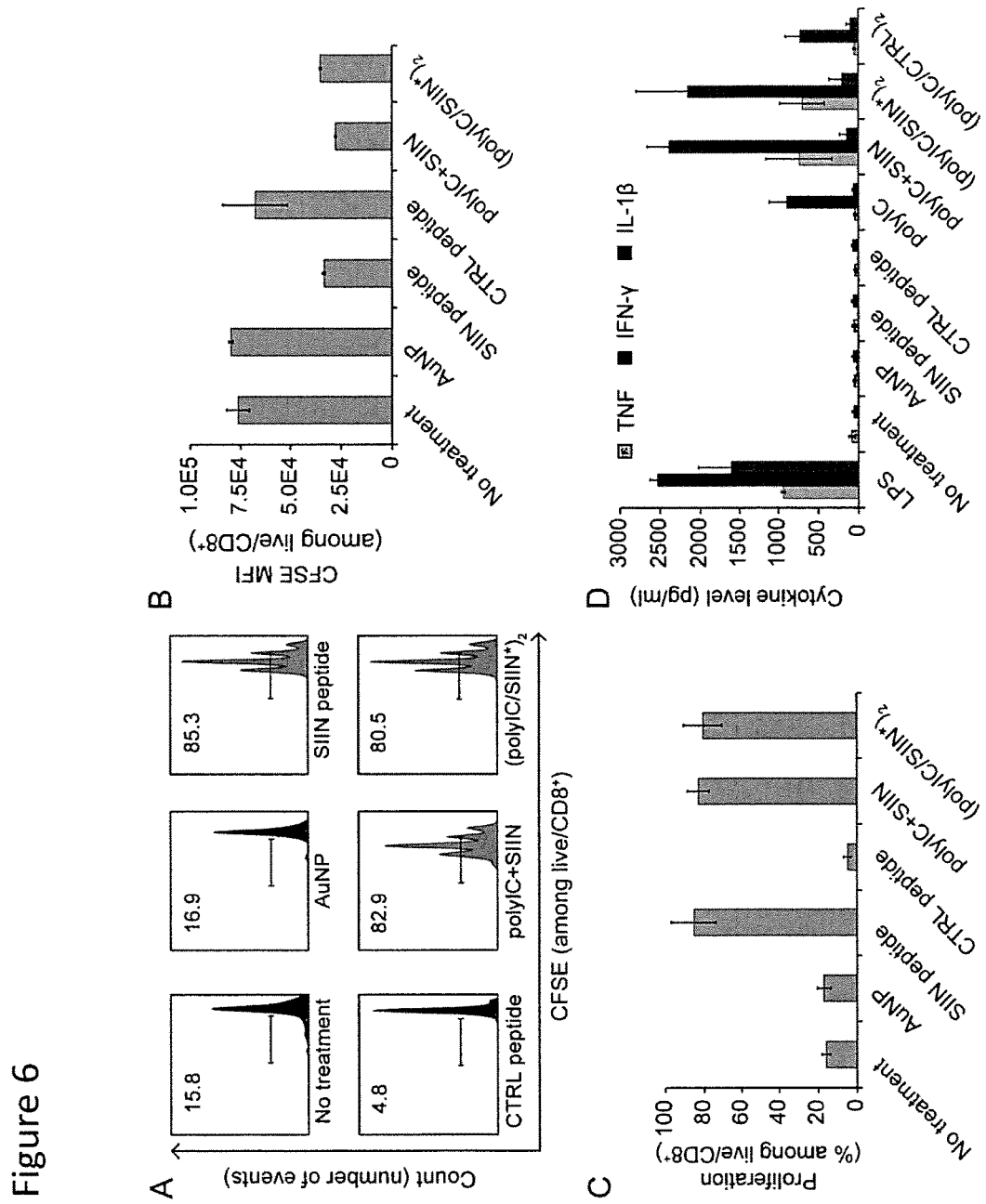
FIG. 6. DCs treated with iPEMs drive proliferation of CD8$^+$ antigen-specific T cells in co-culture. (A) Histogram depicting division and proliferation in OT-1 T cells labeled with CFSE prior to co-culture with DCs incubated with the indicated formulations for 48 hours (see methods). Co-cultures were carried out for 48 hours. (B) Mean fluorescence intensity (MFI) of CFSE levels of the T cells described in (A). (C) Frequency of T cells that proliferated based on the gates shown in (A). (D) ELISA analysis of IFN-γ, TNF, and IL-1β production in the supernatant of the co-cultures described in (A-C). Supernatants were collected 48 hours after co-culture. For all panels, CTRL refers to an irrelevant control peptide not recognized by OT-1 cells. In (D) for each test condition the order of the bars is TNF, IFN-γ, and IL1-β from left to right.

We next investigated whether iPEM-expanded T cells exhibit functional characteristics by quantifying inflammatory and effector cytokine levels in the supernatants of co-culture samples. FIG. 6D summarizes the secretion levels of interferon gamma (IFN-γ), tumor necrosis factor (TNF), and an early inflammatory cytokine associated with DCs and inflammasome actication, interleukin 1-beta (IL1-β). Cells treated with AuNP-(polyIC/SIIN*)$_2$ induced significant levels of both IFN-γ (FIG. 6D, green bar) and TNF (FIG. 6D, yellow bar) compared with cells treated with AuNP-(polyIC/CTRL)$_2$, untreated cells, and cells treated with either polyIC or SIIN peptide. These increased cytokine levels were similar to the high levels observed in cells treated with a mixture of soluble polyIC and SIIN. In contrast to the results for IFN-γ and TNF, the levels of IL-1β—a key component in the NALP3 inflammasome signaling cascade—were only slightly elevated in cells treated with AuNP-(polyIC/SIIN*)$_2$ (FIG. 6D, blue bar). These levels were much lower than those observed in cells treated with LPS, but similar to the near baseline levels measured in cells treated with soluble polyIC, soluble SIIN, or both. Together, the data in FIG. 5 and FIG. 6 confirm that adjuvants used to assemble iPEMs selectively activate TLR pathways, providing the necessary signals to support processing and presentation of iPEM antigens by DCs. These effects drive antigen-specific T cells proliferation and effector cytokine secretion, but do not induce a more generalized inflammatory cytokine associated with less specific inflammation (e.g., inflammasomes).

Immunization with iPEM-coated AuNPs efficiently expands antigen-specific T cells in mice. We next investigated the ability of iPEM-coated AuNPs to drive antigen specific CD8$^+$ T cell responses in mice. In these studies, mice were immunized (i.d.) with peptide and polyIC vaccines formulated as simple mixtures or as iPEMs coated on AuNPs. Each week after the priming immunization (Day 0), MHC-I SIINFEKL (SEQ ID NO:15) tetramer was used to enumerate the frequency of (SEQ ID NO:15) SIINFEKL-specific, circulating CD8$^+$ T cells (FIG. 7A). After 7 days, mice immunized with AuNP-(polyIC/SIIN*)$_2$ exhibited the highest frequency of (SEQ ID NO:15) SIINFEKL-specific CD8$^+$ T cells (0.92±0.14%), compared with 0.58±0.07% in mice immunized with a simple mixture, and 0.27±0.02% in unimmunized mice (FIG. 7A). These levels contracted over the following seven days. To test recall response, mice were boosted on Day 14 using the same respective formulation that each group received during the priming injection. One week post-boost, mice immunized with the iPEMs exhibited a potent and synergistic expansion of antigen-specific CD8$^+$ T cells (4.84±0.56%) that was ~4-fold greater than the frequencies observed in mice immunized with a simple mixture (1.28±0.04%) of polyIC and antigen (FIG. 7B,C). T cells then contracted over 7 days, following kinetics consistent with a classic recall response.

Figure 12:
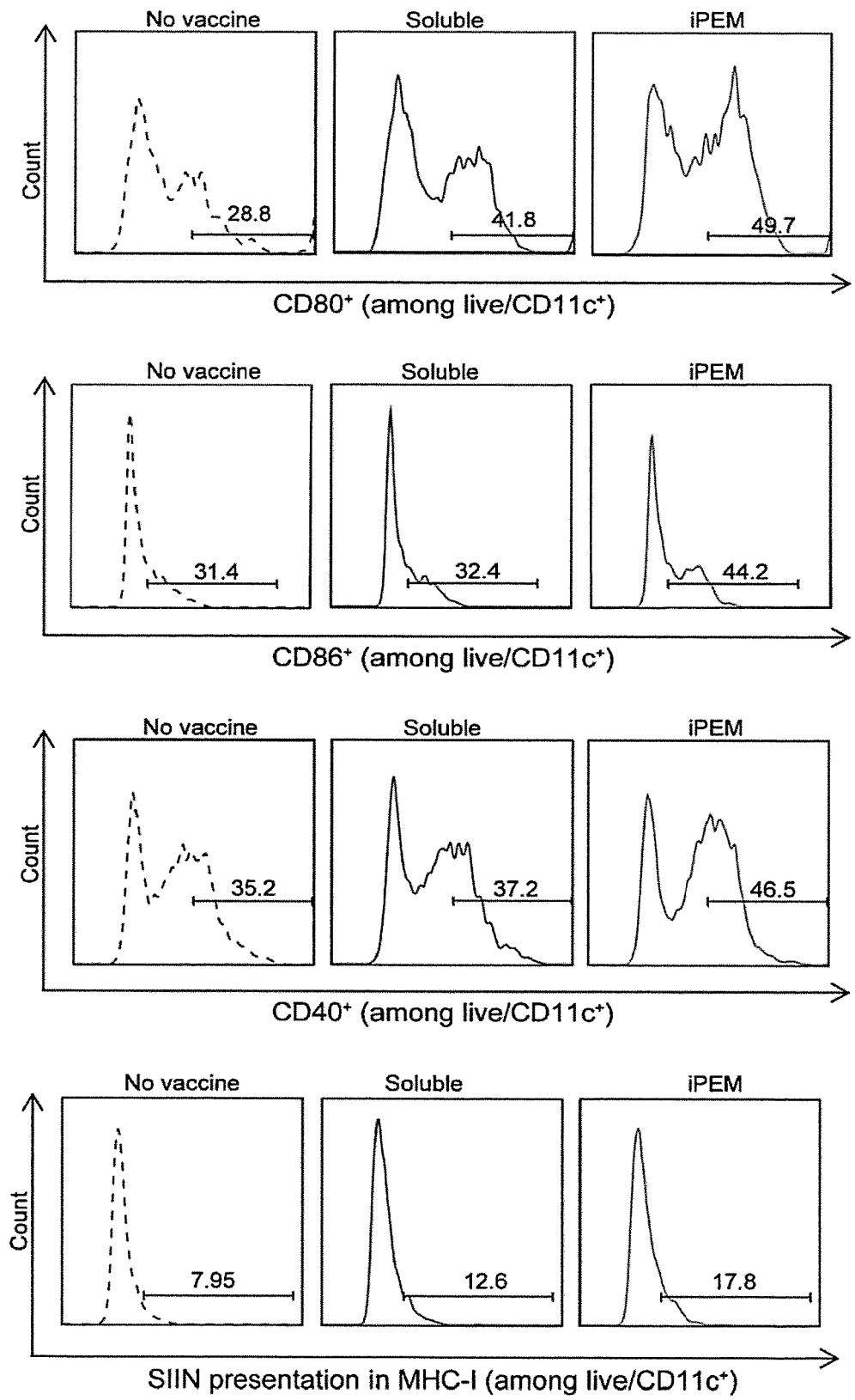
FIG. 12. Representative flow cytometry histograms demonstrating the ability of iPEMs to activate dendritic cells and drive presentation of SIIN peptide via the MHC-I pathway following immunization in B6 mice. These data correspond to FIG. 7D and depict the expression levels of the surface markers (A) CD80, (B) CD86, (C) CD40 and (D) SIIN presentation in MHC-I gated among live, CD11c+ cells isolated from inguinal lymph nodes (LNs) of mice three days after immunization. iPEMs structures used in these studies were AuNP-(polyIC/SIIN*)$_2$.

To assess the mechanism behind the immunogenicity of iPEM-AuNPs, naïve mice were again immunized with either the PEM vaccine or the simple mixture vaccine. After three days, draining LNs were excised and DC activation was measured. Mice receiving the iPEM vaccine exhibited modest increases in CD86 and CD80 expression compared with soluble vaccines, though these differences were only significant compared with levels observed in untreated mice (FIG. 7D, 12). Interestingly, lymph node resident-DCs in mice treated with iPEMs exhibited significant increases in SIINFEKL (SEQ ID NO:15) presentation via MHC-I (FIG. 7D, 12) compared with mice immunized with the simple mixture or unvaccinated mice. Next we tested how T cell expansion kinetics would be altered by more frequent immunization. In this study, mice were primed as above then boosted on day 7 (FIG. 7E-7G), with weekly monitoring of antigen specific T cell expansion in peripheral blood. Mice immunized with iPEM formulations drove striking levels of circulating, SIIN-specific CD8$^+$ T cells, with a mean frequency of 7.20±1.11% and a maximum value or 10.50% (FIG. 7F, 7G). This development was also rapid, occurring within one week after the booster injection. Taken together, these findings demonstrate that iPEMs coated on AuNP enhance response to immune signals, driving more efficient antigen presentation and DC activation to promote potent increases in antigen-specific T cell expansion and recall.

It will be apparent from the foregoing that we have iPEMs with nanoscale coatings comprised of peptide antigens and TLR agonists as adjuvants. iPEMs can be deposited on substrates at both macro and nano-length scales, do not require solvents or mixing, and juxtapose antigens and adjuvants in the films in a manner that maintains the immunogenicity and selectivity of each component. As described above, iPEM assembly does not require any other polymeric components. This is a new feature for the PEM field, as PEMs previously used in vaccination involve other polymers (e.g. poly(methacrylic acid), hyaluronic acid, poly (styrene sulfonate), poly(allylamine hydrochloride), PAH, poly-L-arginine), which can influence adaptive or innate immune response.

Our initial attempts at assembling iPEMs revealed that the zwitterionic nature of SIIN did not provide sufficient charge density to promote sustainable film growth (FIG. 2A, 2B). Thus, we modified SIIN with a $R_9$ cationic anchor to form SIIN*. This modification resulted in linear growth of films assembled from polyIC and SIIN*, demonstrating a simple, modular method to quantitatively control the incorporation of each immune signal by adjusting the number of deposition steps (FIG. 2B, 2C).

We extended iPEMs to injectable particles by leveraging the favorable properties of AuNPs as nontoxic, inert substrates for vaccine delivery. After coating, iPEMs maintained sizes useful for vaccination that ranged between ~50-200 nm, depending on the number of layers deposited. CryoTEM (FIG. 3D) confirmed that iPEMs coated on AuNPs exhibited a core-shell structure consistent with growth indicated by oscillating surface charge (FIG. 3B) and increasing diameter (FIG. 3A). Although on planar substrates, each iPEM bilayer had a thickness of 10.1 nm (FIG. 2A), the greater rate of growth on colloidal substrates (FIG. 3A) may result from interaction between opposite, excess charges on a fraction of coated AuNPs. Such bridging effects could increase the effective diameter and were observable in some particles during cyroTEM imaging (FIG. 3D-ii, FIG. 9A). Stability studies indicated that particles were stable in serum-free medium at elevated temperature, with no significant change in diameter over 24 hours (FIG. 9B). Under more stringent conditions where particles were incubated in serum-rich medium, size increased over 24 hours to 200-300 nanometers, indicating that particles experience some aggregation in the presence of serum. However, these studies also demonstrate that iPEM-AuNPs maintain sizes useful for vaccination even in a challenging mimic of the physiologic environment.

Our studies (FIG. 5A-C) demonstrate that uncoated AuNPs do not exhibit intrinsic properties that activate immune pathways. In contrast, many nondegradable and degradable polymers do elicit these responses. Some of the most relevant materials include common PEM components such as hyaluronic acid, poly(vinylpyrrolidone), and poly (methacrylic acid), along with ubiquitous materials such as polystyrene and PLGA. At least in part, the immunogenicity of many synthetic polymers results from activation of danger-associated molecular patterns (DAMPs) and pathogen-associated molecular patterns (PAMPs) signaling pathways such as inflammasomes. Many of these innate inflammatory pathways are driven by IL-1β production, yet iPEMs coated on AuNPs did not induce this cytokine (FIG. 6D), suggesting that these materials function more specifically (e.g., TLR3 signaling). Martinon, et al. *Annual review of immunology* 2009, 27, 229-65; and Neumann, et al. *Immunology and cell biology* 2014, 92, 535-42).

Additionally, AuNPs can be synthesized with tunable well-defined diameters, support facile surface modification, and increase retention time of conjugated cargoes (e.g., peptides) in lymph nodes after injection. (See, Lin, A. et al *PloS one* 2013, 8, e63550; and Cobaleda-Siles, M., et al. *Small* 2014, 10, 5054-67). Coupling PEMs with AuNPs thus takes advantage of the inert, well-controlled physiochemical properties of AuNPs while providing a simple means of controlling loading of one or multiple types of immune signals.

Figure 4:
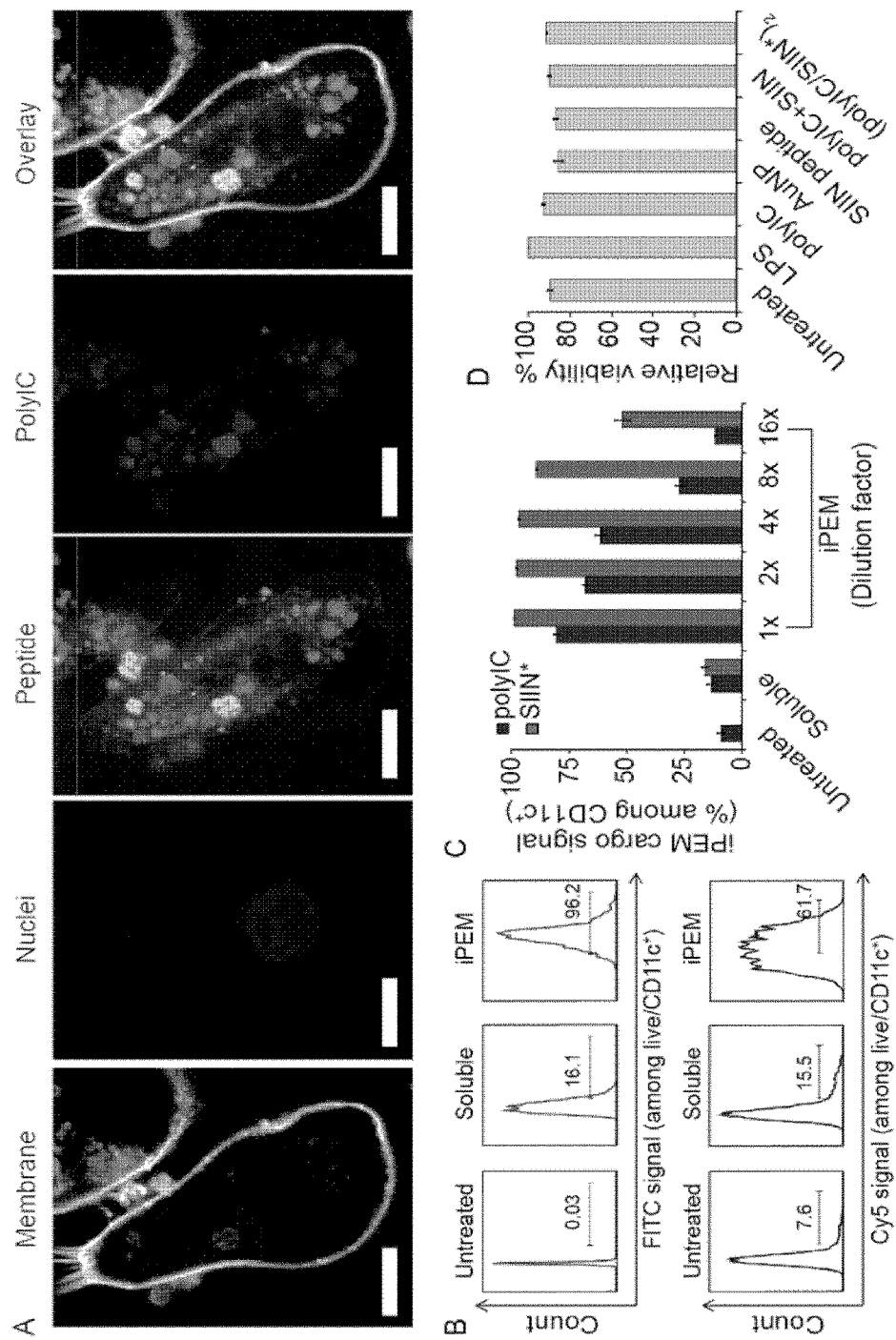
FIG. 4. iPEM-AuNPs are internalized by DCs without toxicity and activate TLR3 signaling. (A) Confocal microscopy images demonstrating the cytosolic distribution of polyIC and SIIN* in primary DCs following a 3 hour incubation with iPEMs using a structure of AuNP-(SIIN*/polyIC)$_2$. The panels indicate the cell membrane (white), nucleus (blue), SIIN* peptide (green), polyIC adjuvant (red), and the overlay (right most image); scale bars are 10 μm. (B) Representative flow cytometry histograms illustrating association of peptide (FITC, green) and polyIC (Cy5, red) with primary DCs. Cells were untreated (left), incubated with soluble peptide and polyIC (center), or incubated with iPEM (right). (C) Quantitative analysis of peptide and polyIC association with DCs based on the gates shown in (B). Soluble formulations correspond to a dose equivalent to that of the iPEM formulation shown at the 4× dilution. (D) Relative viability of DCs following incubation normalized to DCs treated with LPS. PolyIC+SIIN indicates cells treated with a simple mixture of peptide and polyIC.

In DC uptake studies, we discovered that iPEMs co-deliver both antigen and adjuvant to DCs without toxicity (FIG. 4). Interestingly, at low dilutions, we observed much more similar association levels between the peptide and polyIC signal, whereas at the highest dilutions, peptide association was markedly higher than polyIC signal (FIG. 4C). A few possibilities could account for these observations. First, polyIC is particularly susceptible to RNase nuclease activity at dilute concentrations, and RNA degradation could generate free dye molecules which leave the cell to lower the signal. At high concentrations (i.e., low dilutions), it is also possible that sink conditions exist such that the fraction of polyIC degraded over the culture time is relatively small compared with the relative fraction degraded over the same interval when the starting concentration is 16-fold lower (i.e., high dilution). Despite these factors, at higher concentrations, the levels were similar. This is believed to be an important finding since delivery of both an antigen and a stimulatory signal are thought to be required to activate danger/pathogen sensing pathways (e.g., DAMPs, PAMPs) and generate adaptive immunity. Further, $R_9$ is known to be a strong cell penetrating peptide able to carry cargo across cell membrane in an endocytosis-independent manner and likely plays an additional role as a component that enhances the uptake of iPEMs by immune cells.

We also assessed several other immunological characteristics of iPEMs by using primary cell co-culture models. First, DCs treated with polyIC/SIIN* exhibited similar levels of surface activation markers compared to cells treated with equivalent doses of soluble polyIC and peptide (FIG. 5A-C). This result indicates that the potency of immune signals (i.e., antigen, adjuvant) used to assemble iPEMs is not impacted by incorporation into PEMs. With respect to adjuvant, iPEMs formulated with polyIC activated TLR3 signaling, while iPEMs assembled from antigen and C-ODN did not (FIG. 5D). We also demonstrated that DCs treated with AuNPs-(polyIC/SIIN*)$_2$ process SIIN*, resulting in presentation of SIIN peptide via the MHC-I complex (FIG. 5E). We observed selectivity in these studies, as cells treated with iPEMs assembled with an irrelevant control peptide (CTRL) did not exhibit signal corresponding to SIIN presentation following antibody staining. (FIG. 5E). Functionally, treatment of DCs with AuNP-(polyIC/SIIN*)$_2$ before co-culture with OT-I T cells led to T cell expansion (FIG. 6A-C) and secretion of key effector cytokines (FIG. 6D). In particular, AuNP-(polyIC/SIIN*)$_2$ induced both IFN-γ and TNF secretion at levels that were much higher than those observed in wells treated with SIIN peptide, or with AuNP-(PolyIC/CTRL)$_2$ (FIG. 6D). These cytokines are important mediators of adaptive immunity, supporting antiviral response, inflammation, and macrophage activation. Also in this experiment, we observed proliferation of OT-I T cells when DCs were treated with SIIN peptide (FIG. 6A-C), but these responses were not functional as indicated by the lack of cytokine secretion observed in SIIN-treated samples in FIG. 6D. Together, these findings directly confirm that antigens used to assemble iPEMs are presented in a manner that expands T cells with cognate specificity for these antigens, leading to secretion of effector cytokines. Conversely, iPEMs containing adjuvants and irrelevant antigens, while able to activate DCs, do not drive functional responses (i.e., cytokine secretion) in T cells recognizing antigens that were not included during iPEM assembly.

Figure 7:
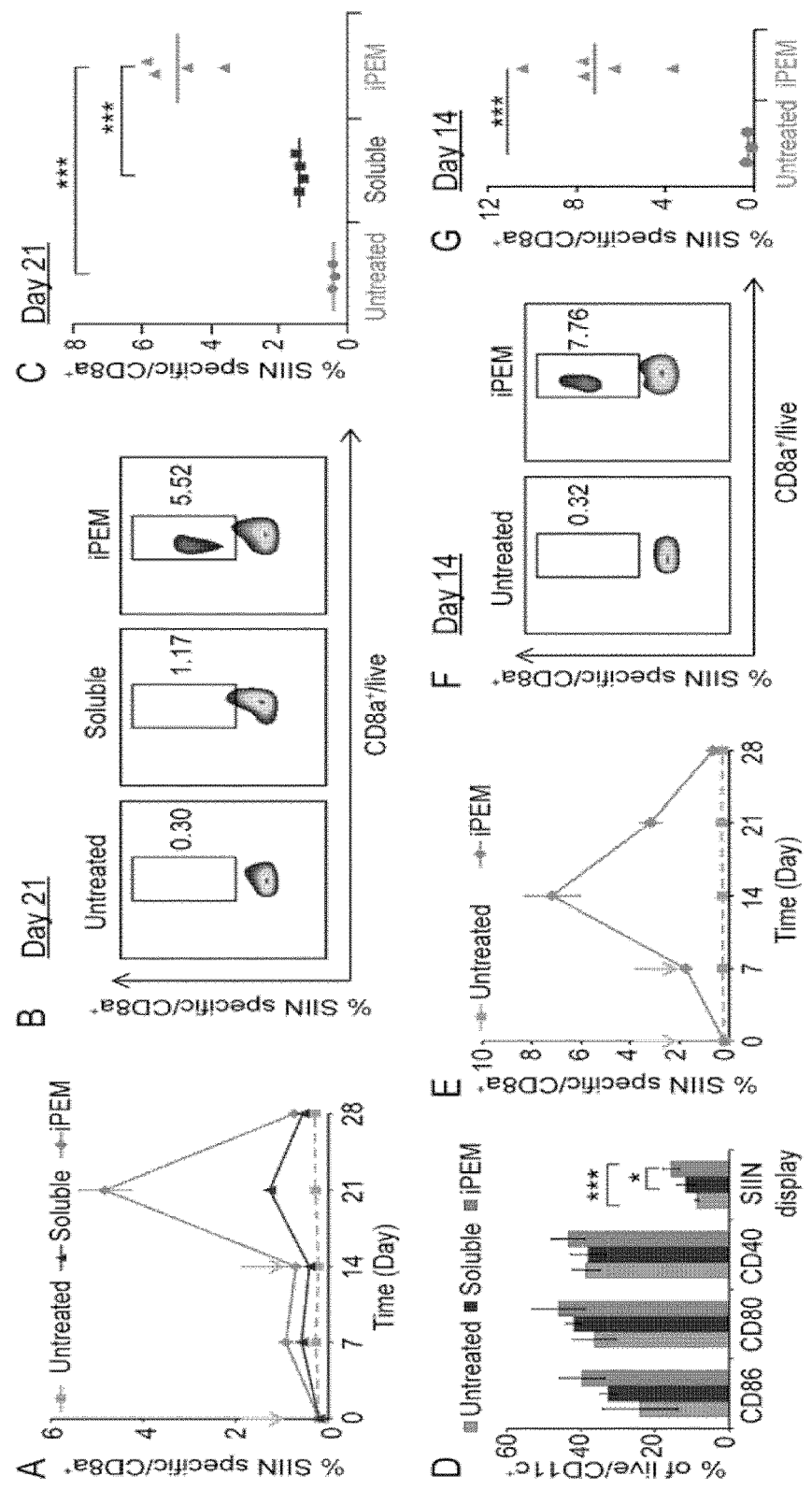
FIG. 7. Immunization with (polyIC/SIIN*)$_2$ (iPEM) activates DCs and promotes efficient primary and secondary CD8$^+$ T cell responses in mice. (A) Development of (SEQ ID NO:15) SIINFEKL-specific CD8$^+$ T cells in peripheral blood over 28 days. Mice were immunized with iPEMs or soluble antigen and adjuvant on day 0 then boosted on day 14. (B) Representative scatter plots showing distributions of SIINFEKL$^+$ (SEQ ID NO:15) and CD8$^+$ T cells on day 21. (C) Statistical analysis of antigen-specific T cell response in each group on day 21. (D) Activation and SIIN presentation by DCs in the draining LNs of mice 3 days after priming immunizations with the indicated vaccines. (E) Development of (SEQ ID NO:15) SIINFEKL-specific CD8$^+$ T cells in peripheral blood over 28 days. Mice were immunized with iPEMs or soluble antigen and adjuvant on day 0 then boosted on day 7. (F) Representative scatter plots showing distributions of SIINFEKL$^+$ (SEQ ID NO:15) and CD8$^+$ T cells on day 14. (G) Statistical analysis of antigen-specific T cell response in each group on day 14.

We also discovered that iPEMs coated on AuNPs generate antigen-specific CD8$^+$ T cells responses in mice (FIG. 7). Compared to soluble antigen and adjuvant, iPEM formulations enhance immune response, generating more potent immunity during both primary and recall responses. In mice, iPEMs greatly increase antigen presentation and generally enhance DC activation in draining lymph nodes. This enhancement may have resulted from specific features of iPEMs including the particulate nature and high signal density. Such characteristics generally facilitate better uptake and activation of antigen presenting cells at injection sites or in draining lymph nodes. This approach was supported by ex vivo culture studies in which iPEMs were internalized at significantly higher levels than soluble peptide or adjuvant (FIG. 4B-4D). However, our studies with other iPEM architectures in FIG. 5A-5C (e.g., AuNP-(polyIC/CTRL)$_2$, AuNP-(C-ODN/SIIN*)$_2$) indicated that— at least in cell culture—simply formulating peptide into iPEMs did not enhance immunogenicity. This indicates that the individual function of immune signal—specificity for the antigen, for example—is discrete from the other signals (e.g., stimulation from the antigen). Further, the finding that both AuNP-(polyIC/CTRL)$_2$ and AuNP-(polyIC/SIIN*)$_2$ drove similar levels of activation indicates that the contribution from adjuvants used to assembled iPEMs is generalizable to different antigens. Thus, and without intending to be constrained by any particular theory, juxtaposition of the antigen and adjuvant in iPEMs likely plays an important role in increasing the frequency of cells encountering and processing both the antigen and adjuvant, a requirement for generation of adaptive immune response. In contrast, none of these features are present in the soluble mixtures of antigen and adjuvant. The synergistic increase in recall response upon boosting also suggests polarization of immune function induced by iPEMs, for example, biasing toward T cell memory.

The following materials and methods were used to present the data described in this example.

Materials. Peptides from ovalbumin (SIINFEKL (SEQ ID NO:15), SIIN; SIINFEKL-R$_9$; SIIN* SIINFEKL-RRRRRRRRR (SEQ ID NO:16)), or an irrelevant control peptide from myelin oligodendrocyte glycoprotein (MOG$_{35-55}$-R$_9$; referred to as CTRL in text and figures) were synthesized by Genscript. All peptides were at least 98% pure and were synthesized with or without a fluorescein (FITC) tag. LPS (TLR4) was purchased from Life Technologies (Invitrogen). PolyIC (TLR3) and Pam3CSK4 (TLR2) were purchased from Invivogen. Non-immunostimulatory control oligonucleotide (referred to as C-ODN in text and figures) was synthesized by Integrated DNA Technologies and had a sequence of TCCTGAGCTTGAAGT (ODN 2088; SEQ ID NO:17). Polyethyleneimine (PEI, MW=50000) and poly(sodium 4-styrenesulfonate) (PSS, MW=70000) were from Sigma. PolyIC was labeled with Cy5 using a Label IT Cy™5 Labeling Kit (Minis Bio LLC). (4',6-diamidino-2-phenylindole) (DAPI), wheat germ agglutinin Texas Red conjugate, and paraformaldehyde (4%) were from Life Technologies. Gold (III) chloride trihydrate (99.9%), chitosan (MW=2000), and phosphate buffered saline (PBS, 1×) were from Sigma. CD11c$^+$ positive isolation beads were from Miltenyi Biotec. EasySep™ mouse CD8$^+$ isolation kits and spleen dissociation medium was from STEMCELL Technologies. All ELISA antibodies and reagents were from BD Biosciences. Antibodies for CD80 (FITC), CD86 (PE-Cy7), CD40 (PE), and SIINFEKL (SEQ ID NO:15) presented in MHC-I (major histocompatibility complex-I) were also from BD Biosciences. RPMI cell culture medium was from MP Biomedicals. C57BL/6J (B6) and (C57BL/6-Tg (TcraTcrb) 1100 Mjb/J) (OT-I) mice were from The Jackson Laboratory.

Cells and animals: All animal research and care was carried out in accordance with local, state, and federal regulations, and under guidelines approved by the University of Maryland IACUC. For primary cell studies, spleens were isolated from 4-8 week old, female mice then processed to a single cell suspension. For studies involving CD11c-purified DCs, splenic DCs from B6 mice were then purified from the cell suspensions by positive isolation according to the manufacturer's instructions. CD8$^+$ T cells were isolated from OT-I mice by negative selection according to the manufacturer's instructions. Splenocytes, isolated DCs, or isolated T cells were then cultured under 5% CO$_2$ in RPMI medium containing 10% fetal bovine serum, penicillin (100 units/ml), and streptomycin (100 μg/ml), HEPES (10 mM), L-glutamine (2 mM), 2-mercaptoethanol (55 μM), non-essential amino acids (1×).

Assembly and characterization of iPEMs on planar substrate: Silicon (Silicon Inc.) and quartz (VWR) substrates were cut into 15 mm×5 mm sections using a diamond dicing saw (Model 1006, Micro Automation). Substrates were cleaned with acetone, methanol, and deionized (DI) water, then dried under filtered, compressed air. Cleaned substrates were treated with oxygen plasma (March Jupiter III) for 3 min to provide a charged surface for layer-by-layer assembly of a precursor PEM layer of (PEI/PSS)$_1$ using modifications of known approaches. Substrates were then immersed in either SIIN or SIIN* solution (500 μg/mL in DI water) for 5 min, followed by immersion in DI water for 30 s. The substrates were then immersed in polyIC solution (500 μg/mL in DI water) for 5 min, followed by an additional 30 s wash in DI water. These steps were repeated until the desired number of bilayers was deposited. For experiments with fluorescently labeled film components, the procedure was identical but polyIC was replaced with Cy5-labeled polyIC and SIIN/SIIN* was replaced with FITC-labeled peptide. Film thicknesses were measured by ellipsometry (Gaertner Scientific) on iPEM-coated silicon substrates, with average values calculated from at least five areas for each substrate. UV-Vis spectrophotometry (Thermo Scientific) was used to measure the absorbance of iPEMs on quartz chips with respective wavelengths of 260 nm and 488 nm, respectively, for polyIC and FITC-labeled peptides, respectively.

AuNPs synthesis and characterization: Synthesis protocols for AuNP templates were adapted from known techniques. Briefly, 50 mL of chitosan solution (0.3%, w/v) in 1% acetic acid was heated to 100° C. and mixed with 40 µL aqueous chlorauric acid ($HAuCl_4$, 0.01 M). The solution was maintained at 100° C. for 25 min to obtain a red colored dispersion.

Assembly and characterization of PEMs on AuNPs: AuNPs were coated with PEMs using an alternating deposition process. Briefly, 1.9 mg of AuNP were collected by centrifugation (13500 rcf, 15 min) and resuspended 100 µL of DI water. AuNPs were then added to 900 µL of polyIC solution (500 µg/mL in DI water), mixed by pipetting, and placed in a sonic water bath for 45 s at room temperature. The suspension was maintained for 5 min, collected by centrifugation at 4° C. (12500 rcf, 15 min), and then washed with DI water to obtain AuNP-polyIC$_1$. Following centrifugation and re-suspension in a fresh aliquot of 100 µL of DI water, polyIC-coated AuNPs were incubated with 900 µL of peptide SIIN* (500 µg/mL) and washed as above to obtain AuNP-(polyIC/SIIN*)$_1$. These steps were repeated until the desired numbers of layers of each component were deposited. In some studies, peptides and polyIC were replaced with fluorescently-labeled versions using FITC for peptides and Cy5 for polyIC. Loading of polyIC and peptides on AuNP were characterized by UV-Vis absorbance of deposition solutions using the Beer-Lambert law at a wavelength of 260 nm for polyIC and standard curves prepared at 488 nm for FITC-labeled peptides. Uncoated AuNPs or iPEM-AuNPs were imaged by cryogenic transmission electron microscopy (TEM) (JOEL JEM 2100) at 100 kv and a temperature of −170° C. The sizes of PEM-modified AuNPs were measured by dynamic light scattering (DLS) using a Zetasizer Nano Z Analyzer. Values reported are mean diameters±standard deviation based on intensity measurements. Stability studies were carried out by incubating iPEM coated AuNPs (0.85 mg/mL) in RPMI 1640 or RPMI 1640+5% fetal bovine serum (FBS) at 37° C. At each indicated time point, dynamic light scattering was used to measure particle size distributions. Because serum-rich medium exhibits inherent scattering from serum proteins on the order of 10's of nm, control measurements using serum-rich medium without addition of iPEMs were used as a baseline. iPEMs (AuNPs-(polyIC/SIIN*)$_2$) were then added to the serum-rich medium. The appearance of a new, non-overlapping peak corresponding to iPEM-AuNPs was observed and software integration was used to analyze the size and standard deviation of the iPEM peak (based on intensity).

Cell internalization studies: Association and uptake of coated AuNPs by DCs was characterized by flow cytometry (FACS CantoII, BD Bioscience) and confocal microscopy (Leica SP5X). For flow cytometry, CD11c$^+$ splenic DCs were seeded in 96 well plates at a concentration of $1.0×10^5$ cells per well. Uncoated AuNPs or AuNPs-(polyIC-Cy5/SIIN*-FITC)$_2$ were then added to each well in a volume of 25 µL. Two-fold serial dilutions were performed using a starting iPEM/AuNPs concentration of 1.9 mg/mL. Cells were then cultured for 16 h. After incubation, cells were washed twice by centrifugation and re-suspended in FACS buffer (PBS+1% BSA). The washed cells were finally resuspended in a DAPI solution (0.1% in PBS+1% BSA) to allow assessment of viability by flow cytometry (i.e., DAPI$^-$ cells). Cells positive for FITC and Cy5 signals compared with negative controls were considered to have associated with iPEMs.

Confocal microscopy was used to confirm cell internalization by incubating 10 µL ($1.9×10^{-2}$ mg) of uncoated AuNPs or AuNPs coated with (polyIC-Cy5/SIIN*-FITC)$_2$ with $6.0×10^6$ DCs in 25 mm dishes with glass cover slip inlays. After 4 h the cells were gently washed 2 times with PBS to remove the free iPEM-coated AuNPs. Cells were then fixed with 4% paraformaldehyde for 15 min at 37° C. and washed twice with PBS. Cell membranes were stained with a wheat germ agglutinin Texas Red conjugate (5 ug/mL in PBS) at room temperature for 10 min protected from light. The cells were then washed with PBS, resuspended in Hoescht stain and imaged by confocal microscopy under a 63× oil immersion objective. Individual image channels were collected for DAPI (nuclei), FITC (peptide), Texas Red (cell membrane), and Cy5 (polyIC) and then merged and analyzed using CellSens, ImageJ, and Adobe Creative Cloud.

DC activation and antigen presentation: For DC activation and antigen presentation studies, CD11c$^+$ splenic B6 DCs were stimulated with AuNPs coated with 0 to 3 bilayers of polyIC (or C-ODN) and each peptide for 24 h. Untreated cells or cells treated with LPS (1 µg/mL), polyIC (10 µg/mL), C-ODN (10 µg/mL), AuNPs ($1.9×10^{-2}$ mg/well), SIIN peptide (5 µg/mL), or CTRL peptide (5 µg/mL) were used as controls. After incubation with iPEM-coated AuNPs, DCs were washed twice with PBS+1% BSA, then blocked in anti-CD16/CD32 (Fcγ III/II receptor) (25× dilution, BD Biosciences) for 15 min at room temperature. The cells were then stained with antibodies for CD80 (FITC), CD86 (AmCyan-A), and CD40 (PE). To quantify presentation of SIIN-FEKL (SEQ ID NO:15) via the MHC-I pathway, cells were stained with a PE-Cy7 labeled antibody (BioLegend) against anti-mouse H-2Kb bound to OVA257-264 (SIINFEKL (SEQ ID NO:15)). All antibodies were fluorescent conjugates and were used by staining for 20 min at a 1:300 dilution in PBS+1% BSA. Cells were then washed twice in PBS+1% BSA and resuspended in a DAPI solution for analysis by flow cytometry. The data analysis was performed with Flowjo (Treestar).

TLR3 signaling: TLR3 activity was assessed using HEK-Blue mTLR3 cells (Invivogen). Cells were seeded at a concentration of $5.0×10^4$ cells per well, followed by treatment with Pam3CSK4 (0.2 µg/mL), LPS (1.0 µg/mL), polyIC (10 µg/mL), C-ODN (5 µg/mL), SIIN peptide (5 µg/mL), AuNPs ($1.9×10^{-2}$ mg/well), AuNP-(C-ODN/SIIN*)$_2$ (80 µg/mL), or AuNP-(polyIC/SIIN*)$_2$ (80 µg/mL). After 16 hours the absorbance was read at 625 nm using a UV/Vis platereader (Molecular Devices).

T cell co-culture, activation, and proliferation: CD11c$^+$ B6 splenocytes were treated with AuNPs (uncoated or iPEM-coated), LPS (1 µg/mL), polyIC (10 µg/mL), AuNPs ($1.9×10^{-2}$ mg/well), SIIN peptide (5 µg/mL), control peptide (CTRL, 5 µg/mL), or soluble polyIC (10 µg/mL)+SIIN (5 µg/mL). Untreated cells were used as a negative control. After 48 h, T cells isolated from OT-I mice were stained with CellTrace™ CFSE cell proliferation reagent (5 µg/mL in cell culture medium) by incubation at room temperature for 5 min. T cells were then co-cultured with each DC sample by addition of $3.0×10^5$ T cells per well. After an additional 48 h of incubation, cells were centrifuged (800 rcf for 5 min), the supernatants were collected for ELISA, and the cells were washed in PBS+1% FBS. Cells were then blocked as above and stained with anti-CD8a (APC) for 15 min at room temperature. Lastly, cells were washed twice and re-suspended in DAPI. T cell proliferation was determined by the mean fluorescence intensity (MFI) of CFSE signal among DAPI$^-$, CD8$^+$ cells compared with positive and negative controls.

ELISA: Cytokine levels in the supernatants collected from DCs/T cell co-cultures were analyzed by ELISA using mouse TNF, IFN-γ, and IL-1β ELISA reagents (BD Bioscience) according to the manufacturer's instructions. 10 μL of each supernatant was used in each test, and cytokine concentrations were quantified by comparison to standard curves prepared from known standards.

In vivo immunization studies: For in vivo studies, B6 mice in groups of five were unimmunized or injected intradermally on each flank (i.d., 25 μL) with either vaccine formulation (i.e., soluble, AuNP-(polyIC/SIIN*)$_2$) containing equivalent doses of antigen (32.5 μg) or adjuvant (52.0 μg). Mice were primed at day 0, and in some studies received a booster injection on either day 7 or on day 14. For in vivo activation and antigen presentation studies, mice were injected with either vaccine formulation (i.e., soluble, AuNP-(polyIC/SIIN*)$_2$). After 3 days, mice were euthanized, the inguinal lymph nodes were collected, and then processed to a single cell suspension by passage through a cell strainer (40 μm). Cells were blocked and stained as above before analysis by flow cytometry.

In vivo analysis of antigen-specific CD8$^+$ T cell expansion: During immunization studies, peripheral blood was collected from mice at day 0, 7, 14, 21, and 28. The blood samples were treated with 1 mL ACK lysing buffer (Life Technologies) for 5 min, collected by centrifugation (800 g, 5 min), treated with ACK a second time, then washed in PBS before collection. Blocking was next carried out as described above. Cells were then stained with SIINFEKL (SEQ ID NO:15) MHC-I tetramer (PE conjugate) for 30 min using a 25× dilution, and for CD8a (APC conjugate) as described above. The stained cells were washed and resuspended in DAPI, then analyzed by flow cytometry.

Statistical analysis: One way ANOVA with a Tukey post-test was performed using Graphpad Prism (version 6.02) for statistical testing. P-values of <0.05, *; <0.01, ; and <0.001, * were used to indicate statistical significance. Data are reported as mean values±standard error of the mean (SEM). All experiments were conducted using replicates of 4 samples (e.g., cell culture wells) or animal group sizes of 3-5 mice per group. Data shown in all figures are representative examples of 2-4 experiments with similar results.

Example 2

Figure 13:
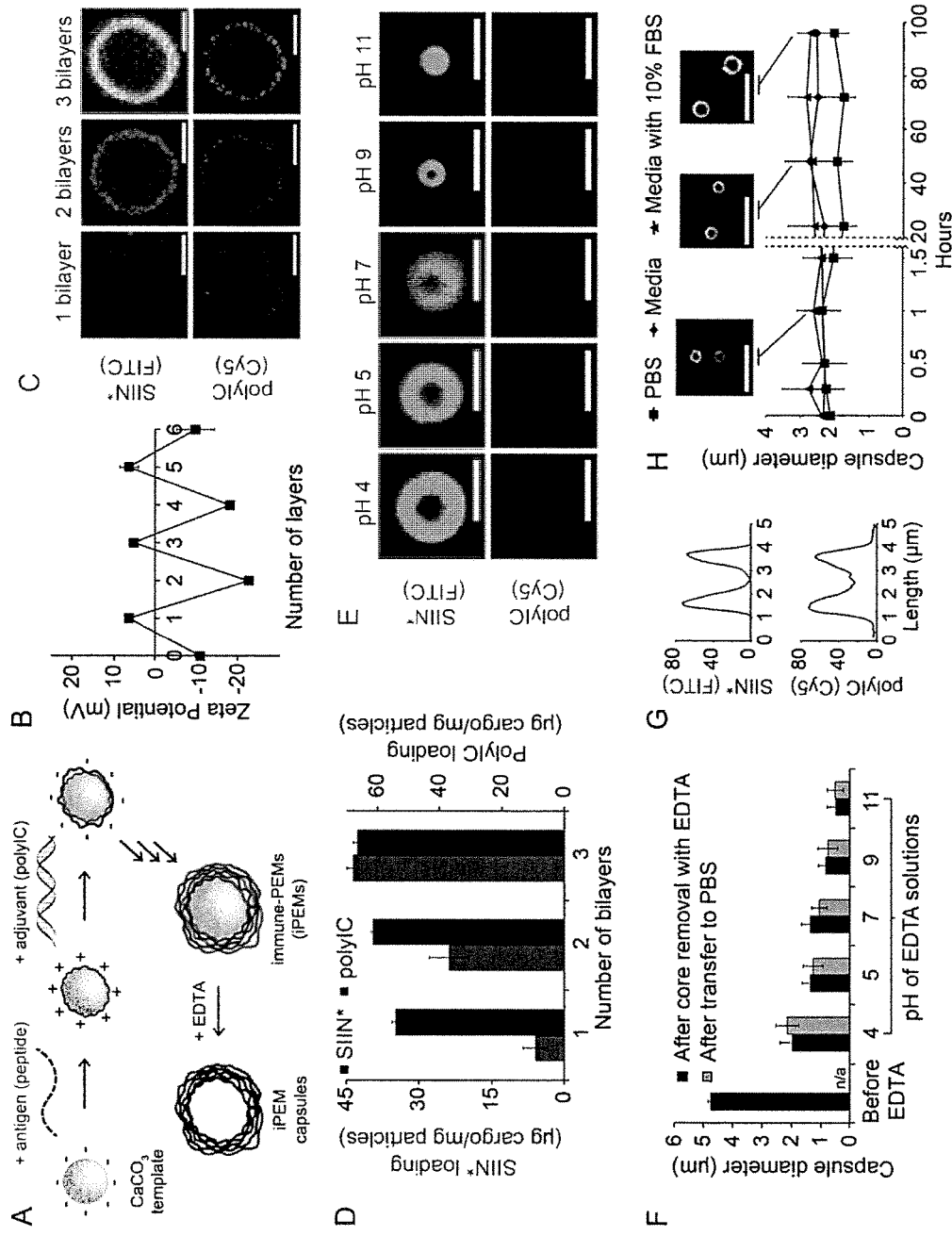
FIG. 13. iPEM capsules are stable and exhibit sizes that are a function of pH. A) Schematic representation of iPEM capsule synthesis using antigens and adjuvants. B) Zeta potential measurements indicating charge inversion as each antigen or adjuvant layer is adsorbed during iPEM synthesis. C) Confocal microscopy images and D) cargo loading during assembly of (SIIN*/polyIC)$_3$ on CaCO$_3$ templates. E) Confocal microscopy images and F) diameter of iPEM capsules formed following removal of the core with EDTA at the indicated pH values (black bars), and after subsequent transfer to PBS (grey bars). G) Fluorescent intensity distributions of SIIN* (FITC) and polyIC (Cy5) across a cross-section of a representative capsule formed by EDTA treatment at pH 4. H) Stability of iPEM capsules during incubation at 37° C. in PBS, media, or media with 10% FBS. The inlay shows images of iPEM capsules during incubation in media with 10% FBS for 1 hr, 48 hrs, and 96 hrs. Values for all panels represent the mean±standard deviation. Scale bars: C) and E) 2.5 µm; H) 10 µm.
Figure 16:
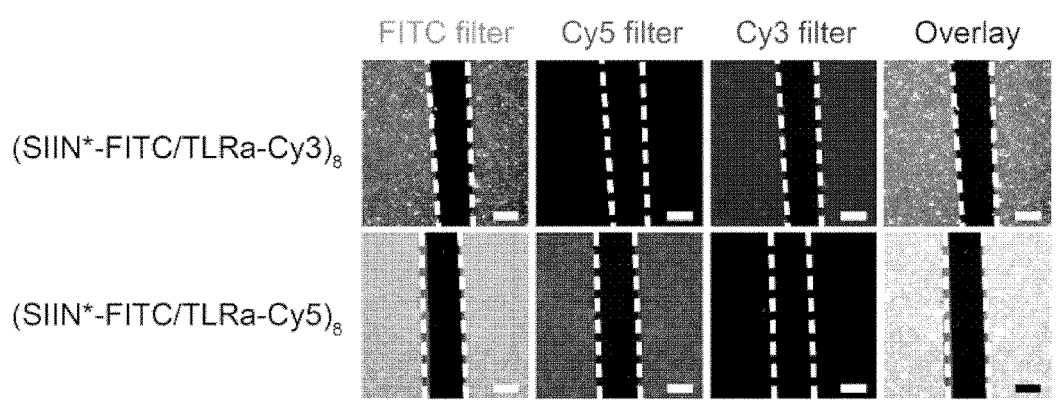
FIG. 16. Fluorescently-labeled antigen (FITC, green) and adjuvant (Cy3, red; Cy5, magenta) can be independently visualized without signal overlap between filter sets. iPEMs were assembled on quartz microscope slides using the indicated components, then a needle was used to remove of portion of the film to provide contrast for imaging (white lines).

This Example expands on Example 1 and describes a platform for simplifying iPEM design and evaluation by electrostatically-assembling stable vaccine capsules solely from immune signals, and without other supports. These iPEMs capsules mimic many features of biomaterials (e.g., tunable sizes, co-delivery), enhance vaccination by increasing the density and programmability of immune signals, and eliminate components that can exhibit poorly defined immunogenic characteristics (e.g., synthetic materials).

iPEM capsules are assembled through alternate deposition of peptide antigens and toll-like receptor agonists (TLRas) as adjuvants (FIG. 13A). As described above, this process is all aqueous and does not require heating, cooling, or mixing. iPEMs are built on a sacrificial core in an LbL manner and are comprised of polyinosinic-polycytidylic acid (polyIC)—an immunostimulatory double stranded RNA (i.e., TLR3 agonist)—and antigenic peptides from a common model antigen, ovalbumin (SIINFEKL (SEQ ID NO:15)). In this system, the TLRas serve as potent molecular adjuvants and polyanionic film components, while SIINFEKL (SEQ ID NO:15) modified with nona-arginine (SIIN*) at the carboxy-terminus (i.e., SEQ ID NO:16) serves as the antigen and a cationic film component. To design iPEM capsules formed entirely from these immune signals, we first assembled iPEMs on 5 μm CaCO$_3$ sacrificial cores. Film assembly was confirmed by the oscillation of zeta potentials between positive and negative values as each respective layer of SIIN* and polyIC was deposited (FIG. 13B). Confocal microscopy further confirmed film growth, with increasing fluorescence corresponding to SIIN* and polyIC as the bilayer number increased (FIG. 13C). These images also revealed polyIC and SIIN* were juxtaposed in the film structure, as indicated by colocalization of the fluorescent signal for each component (FIG. 13C). Control studies confirmed fluorescent signals from antigen and adjuvant could be independently visualized (FIG. 16). Cargo loading was also tunable by varying the number of layers deposited, with UV/vis spectroscopy and fluorimetry indicating loading of ~44 μg SIIN*/mg particles and ~67 μg polyIC/mg particles during assembly of (SIIN*/polyIC)$_3$ (FIG. 13D).

To form support-free iPEM capsules, CaCO$_3$ templates were removed with ethylenediaminetetraacetic acid (EDTA), leaving (SIIN*/polyIC)$_3$ capsules entirely of antigen and adjuvant (FIG. 13A). Capsule size could be tuned by varying the pH of the EDTA solution used for core removal, with an inverse relationship between capsule size and increasing EDTA pH. Cores removed with EDTA at a pH of 4 resulted in capsules with micro-scale diameters (~2.2 μm), whereas capsules exhibited nanoscale diameters (~700 nm) when cores were removed with EDTA at higher pH values (FIG. 13E, F). Past fundamental studies have shown that polyelectrolyte capsule size and stability are relatively constant over intermediate pH ranges where electrostatic forces are dominant. At more acidic or more basic conditions outside this range, hydrophobic forces and surface tension become dominant as excess charge of one polyion is no longer fully compensated. These effects minimize capsule size, and at extreme pH values, can lead to collapse. Our results with iPEMs are in agreement with this theory, as we observed stable capsules from pH 4-9, but collapsed capsules at pH 11 as uncompensated charge on polyIC increased due to decreasing cationic charge on SIIN* at this very basic pH (FIG. 13E, F). We also discovered that the sizes of iPEM nanocapsules and microcapsules were maintained upon transfer to PBS after removal of the core (FIG. 13F, grey bars), confirming a robust approach for tuning capsule diameter. We selected capsules formed with EDTA at pH 4 for further study and confirmed colocalization of antigen and adjuvant in the capsule shell after core removal by pixel intensity analysis of confocal microscopy line scans (FIG. 13G). Incubation of iPEM capsules in PBS, media, or media supplemented with 10% FBS confirmed capsules were stable for at least 96 hrs (FIG. 13H). Of particular note, iPEM capsules incubated in complete media exhibited only a slight increase in size, with an initial mean diameter of 2.4 μm compared to 2.7 μm after 96 hours (FIG. 13H). These data confirm that stable iPEM capsules can be assembled from peptide antigens and adjuvants at different length scales and with control over the composition of the capsules. This is an attractive feature for vaccination, for example, to allow design of nanoscale capsules that promote passive drainage to lymph nodes, or of larger capsules that are readily internalized by peripheral antigen presenting cells.

Figure 17:
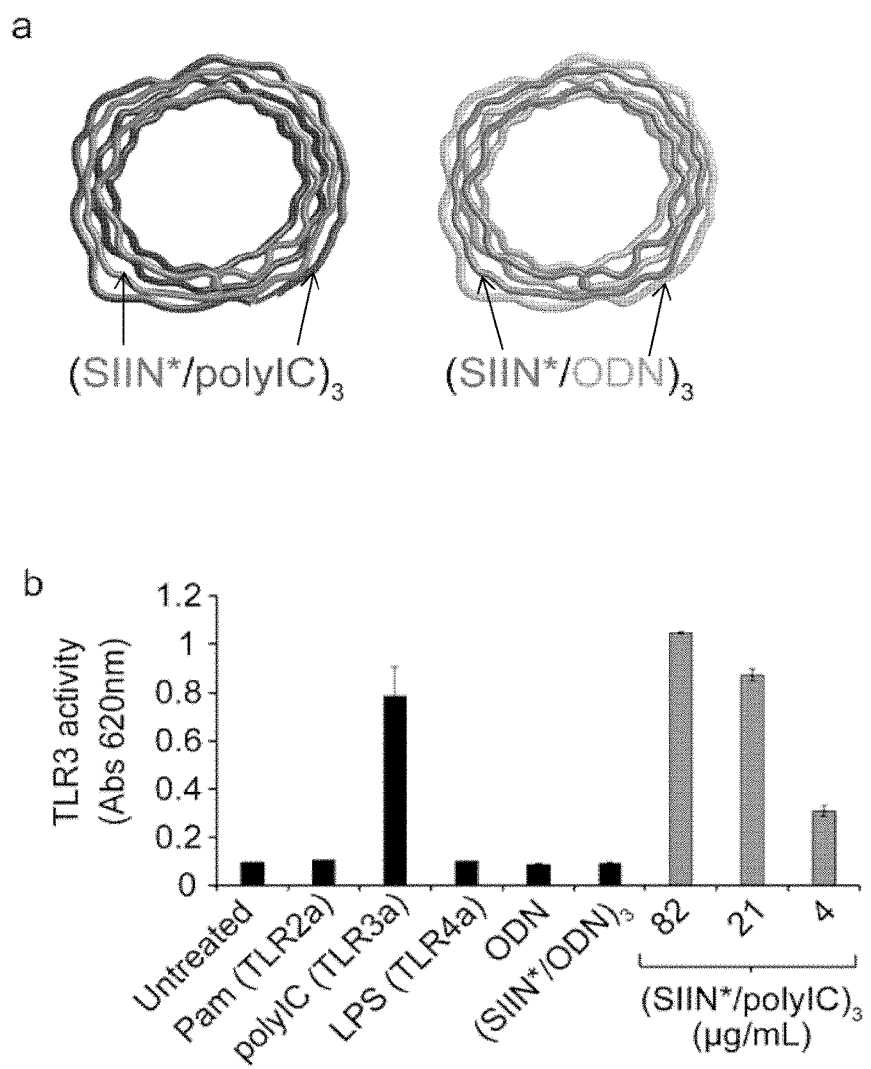
FIG. 17. iPEM capsules efficiently trigger TLR-specific signaling. a) Schematic illustration of iPEM capsules assembled from SIIN* and polyIC (immunogenic) or SIIN* and a non-immunogenic control oligonucleotide, ODN. b) Quantification of TLR3-specific signaling in reporter cells following treatment using iPEM capsules designed with an architecture of (SIIN*/polyIC)$_3$ or (SIIN*/ODN)$_3$, or controls of Pam3CSK4 (TLR2a), LPS (TLR4a), or ODN. Data are representative of 2-3 studies conducted in triplicate. Values for all panels indicate the mean±s.e.m.
Figure 18:
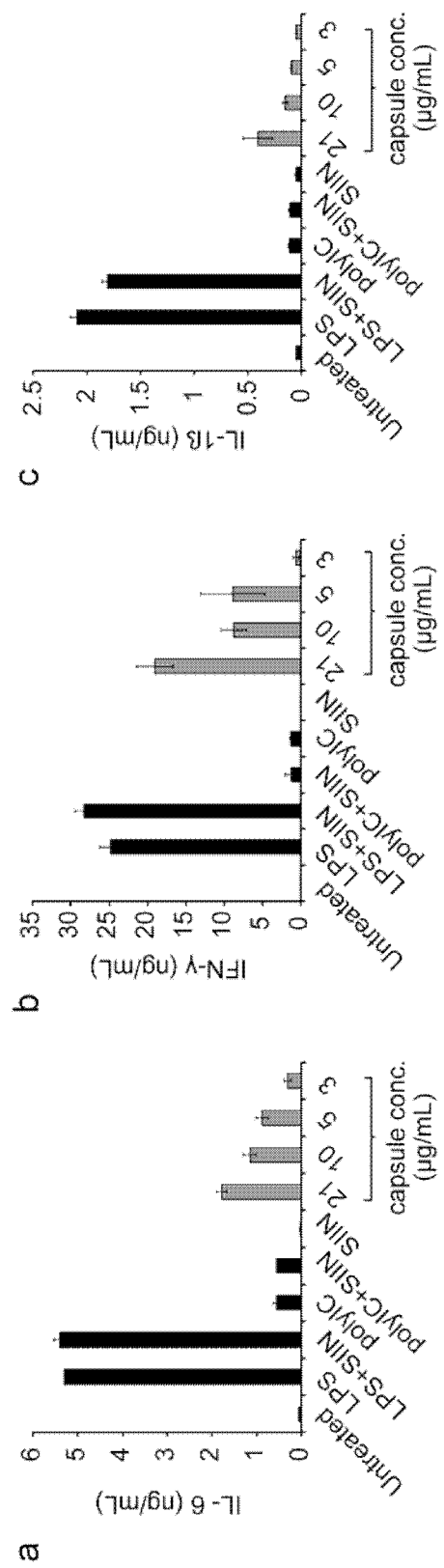
FIG. 18. iPEM capsules induce proinflammatory cytokines. ELISA was used to measure the secretion of the pro-inflammatory cytokines (a) IL-6, (b) IFN-γ, and (c) IL-1β during primary DC culture measured by ELISA. Values for all panels indicate the mean±s.e.m. Data are representative of 2-3 experiments each conducted in triplicate.

We next assessed the adjuvant effects of iPEM capsules by measuring TLR activation and iPEM-triggered secretion of inflammatory cytokines. iPEM capsules were prepared using SIIN* and either polyIC (TLR3 agonist) or a non-immunogenic oligonucleotide (ODN) (FIG. 17). Reporter cells treated with (SIIN*/polyIC)$_3$ iPEM capsules displayed efficient activation of TLR3, while (SIIN*/ODN)$_3$ capsules did not activate TLR3 signaling. In line with these findings, iPEM capsules incubated with primary dendritic cells (DC) induced pro-inflammatory cytokines—including IFN-γ and IL-6—at levels that were significantly higher than cells treated with equivalent doses of free polyIC, peptide, or peptide and polyIC (FIG. 18). Together, these results confirm that iPEM capsules activate pathogen detection and response pathways that play a key role in the generation of adaptive T cell immunity.

Figure 14:
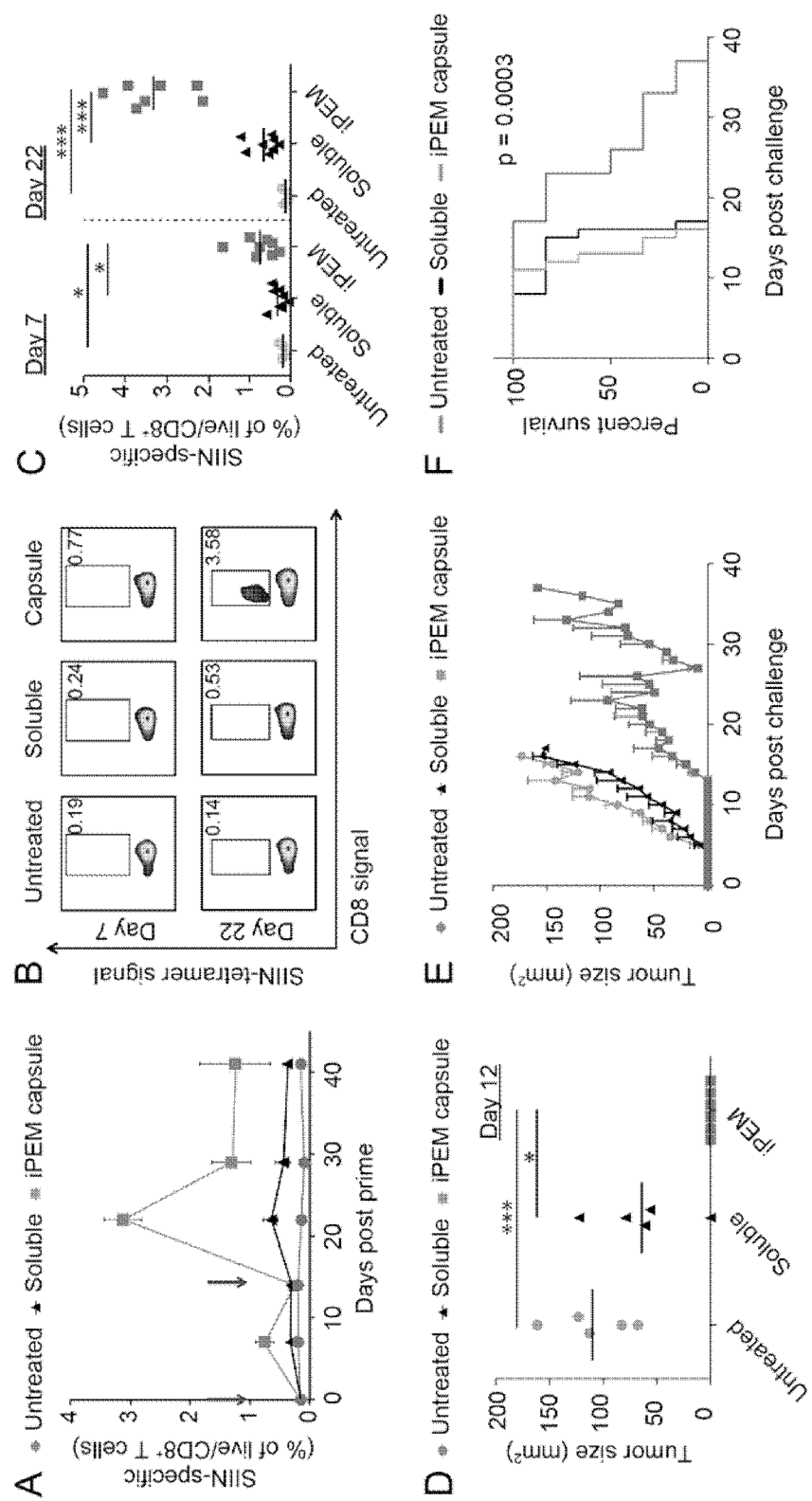
FIG. 14. Immunization with iPEM capsules promotes synergistic expansion of antigen specific CD8+ T cells by enhancing DC function. A-C) C57BL/6 mice were immunized intradermally with equivalent doses of antigen and adjuvant formulated in iPEM capsules or using a mixture of free components at day 0 and day 15 (red arrows). A) Quantification of (SEQ ID NO:15) SIINFEKL-specific CD8+ T cells in peripheral blood measured over 41 days using MHC-I SIINFEKL (SEQ ID NO:15) tetramer. B) Representative scatter plots and (C) mean frequencies of live/CD8+/SIINFEKL+ (SEQ ID NO:15) cells in peripheral blood at the peak of primary (day 7) and recall (day 22) responses following immunization. D) Tumor size on day 12 after a challenge with 1×10$^6$ B16-OVA cells administered on day 36. Mice were vaccinated with the indicated formulations on days 0, 15, and 28. E) Tumor burden over time in mice immunized as described in (D). F) Survival curves demonstrating immunization with iPEM capsules prolongs survival after tumor challenge. Values for all panels indicate the mean±s.e.m and are representative of 2-3 experiments using N=4 for groups of naïve mice, N=8 mice/group for immunization studies, N=6 mice/group for tumor studies. Statistics are indicated for all significant comparisons using criteria of * p≤0.05;  p≤0.01; * p≤0.001.

To assess iPEM capsules as a vaccination platform, mice were immunized intradermally with iPEMs or equivalent doses of antigen and adjuvant in free form. One week after injection, iPEMs elicited a modest but significant increase in circulating $CD8^+$ T cells specific for the SIINFEKL (SEQ ID NO:15) antigen used to assemble iPEMs (FIG. 14A). Following a booster injection on day 15, mice exhibited potent recall responses, with up to 4.6% of circulating $CD8^+$ T cells primed against SIINFEKL (SEQ ID NO:15) (FIG. 14A-C). The mean frequency observed with iPEM capsules (3.1%) represented a 4.5-fold enhancement over the level (0.7%) observed in mice treated and boosted with the admixed formulations of antigen and polyIC (FIG. 14A-C). The higher (SEQ ID NO:15) SIINFEKL-specific T cell levels associated with iPEM immunization were also durable until the conclusion of the study on day 41.

To determine if these enhanced T cell responses translated to functional immunity, we challenged immunized mice with an aggressive dose of $1 \times 10^6$ B16 tumor cells expressing OVA. Compared with mice receiving admixed vaccines, iPEMs delayed the formation of palpable tumors (FIG. 14D), and dramatically slowed tumor growth (FIG. 14E). These effects drove a statistically significant increase in median survival, with a value of 25 days for mice immunized with iPEM capsules, and 16 days and 13 days for soluble formulations and unimmunized mice, respectively (FIG. 14F). Thus, iPEMs enhance antigen-specific $CD8^+$ T cell primary and recall responses in a manner that translates to significant protection during an aggressive tumor challenge.

Figure 15:
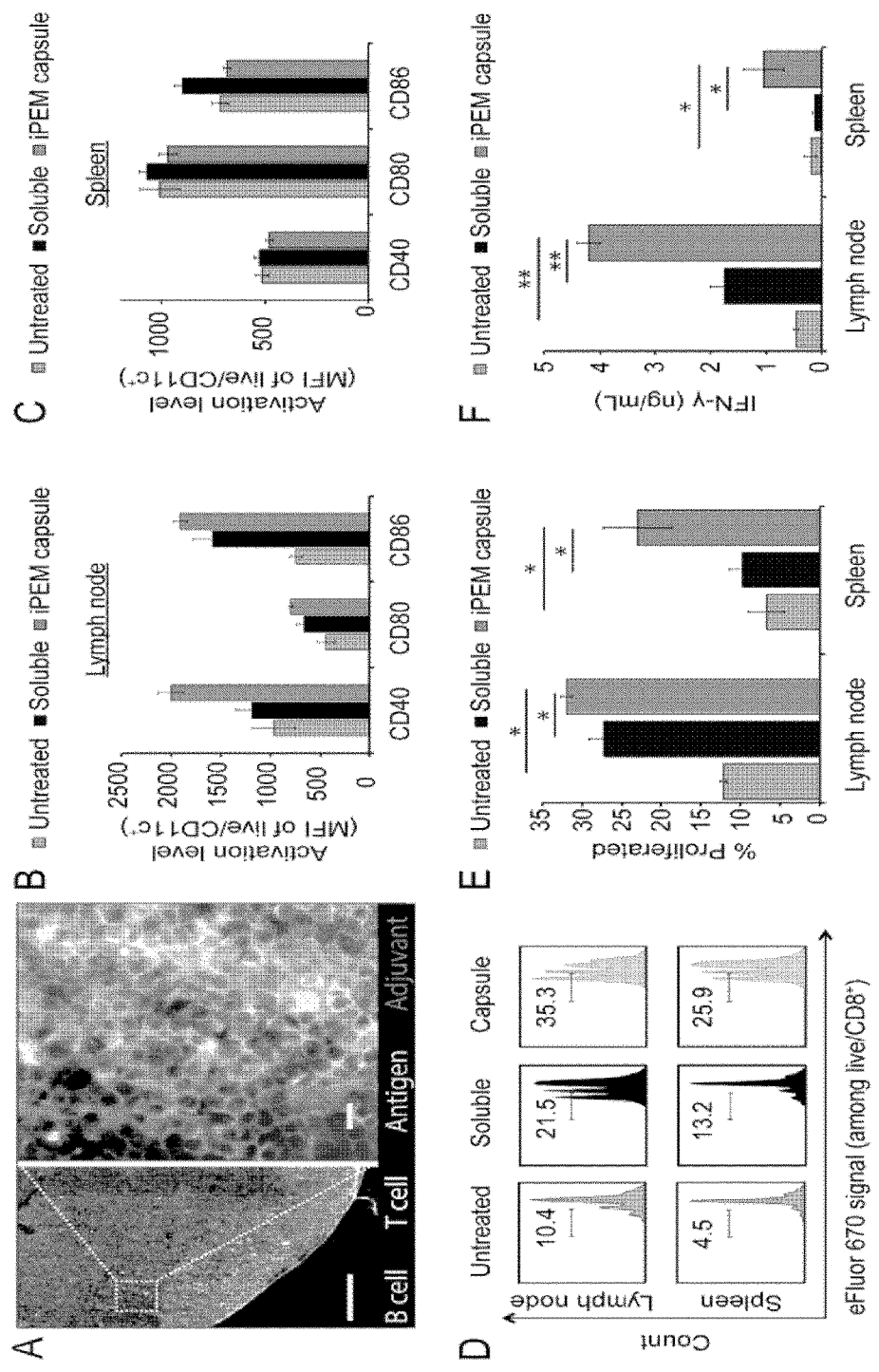
FIG. 15. A) Immunohistochemical staining of draining lymph node three days after intradermal immunization with the indicated vaccine (T cells (CD3): white; B cells (B22): blue; SIIN*: green; polyIC: red). Scale bars are 200 µm and 10 µm (inlay). B-F) DCs from (B) draining lymph nodes and (C) spleens were isolated and evaluated for activation using expression of CD40, CD80, and CD86. D) Histograms and (E) mean frequencies showing the proliferation of labeled, SIIN-specific CD8+ T cells co-cultured for 48 hrs with DCs from lymph nodes and spleens prepared as in (B) and (C). F) Secretion of IFN-γ in DC and T cell co-cultures as in (B) and (C). Values for all panels indicate the mean±s.e.m and are representative of 2-3 experiments using N=4 for groups of naïve mice, and N=8 mice/group for immunization studies. Statistics are indicated for all significant comparisons using criteria of * p≤0.05;  p≤0.01; * p≤0.001.
Figure 19:
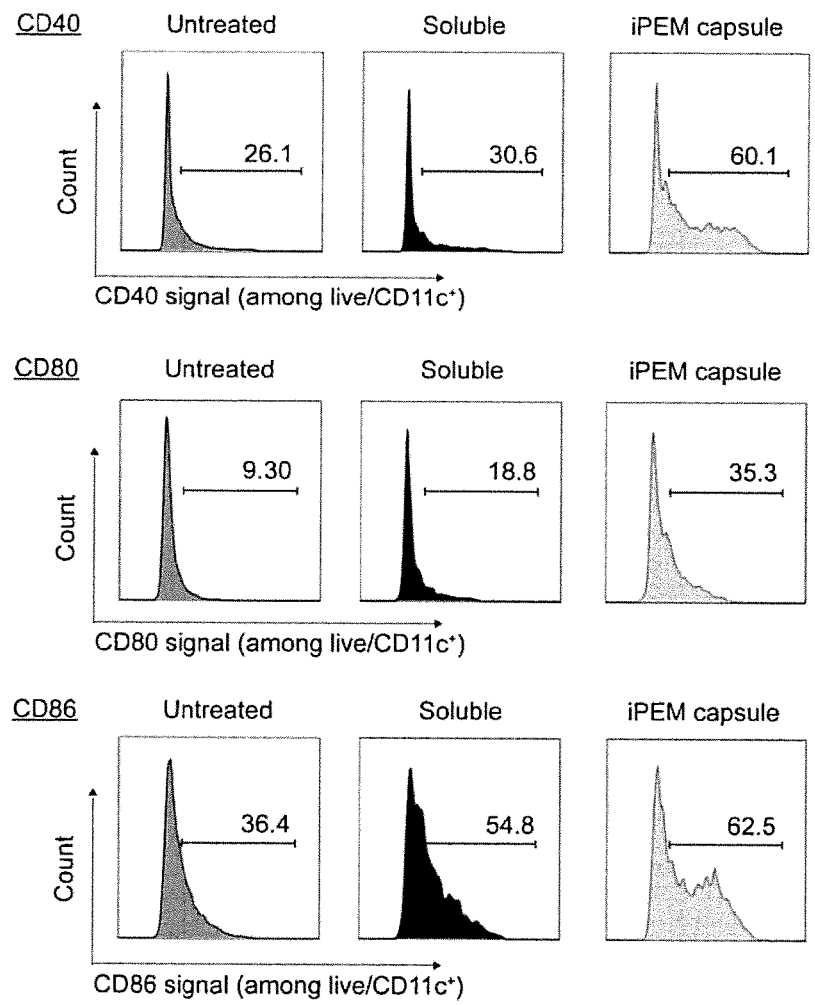
FIG. 19. In vivo activation of lymph node-resident DCs by iPEM capsules. a) Representative flow cytometry histograms of CD40, CD80, and CD86 expression among DCs isolated from draining lymph nodes of untreated mice, or mice immunized with antigen and adjuvant in soluble form or assembled into iPEM capsules. Lymph nodes were harvested and analyzed three days after immunization. b) Frequencies of CD40, CD80, and CD86 expression in DCs from draining lymph nodes corresponding to the groups described in (a). Values for all panels indicate the mean±s.e.m. (N=4 mice/group). Data are representative of 3 similar experiments. For a) and b) the order of the data summarized in the panels is from left to right Untreated, Soluble, iPEM capsule.
Figure 19:
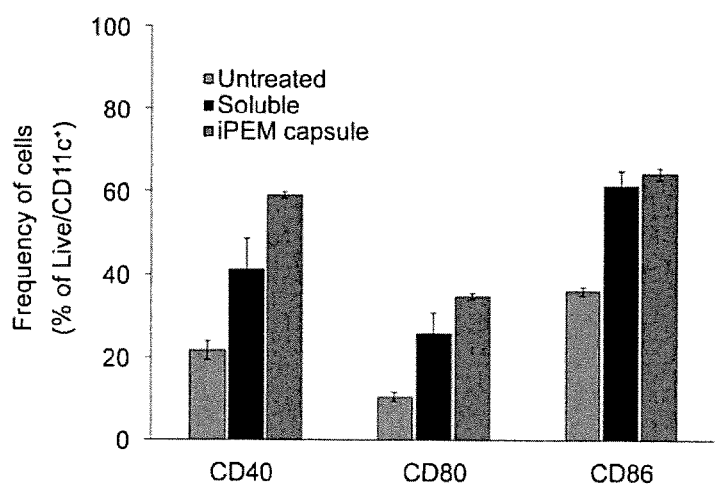
Figure 20:
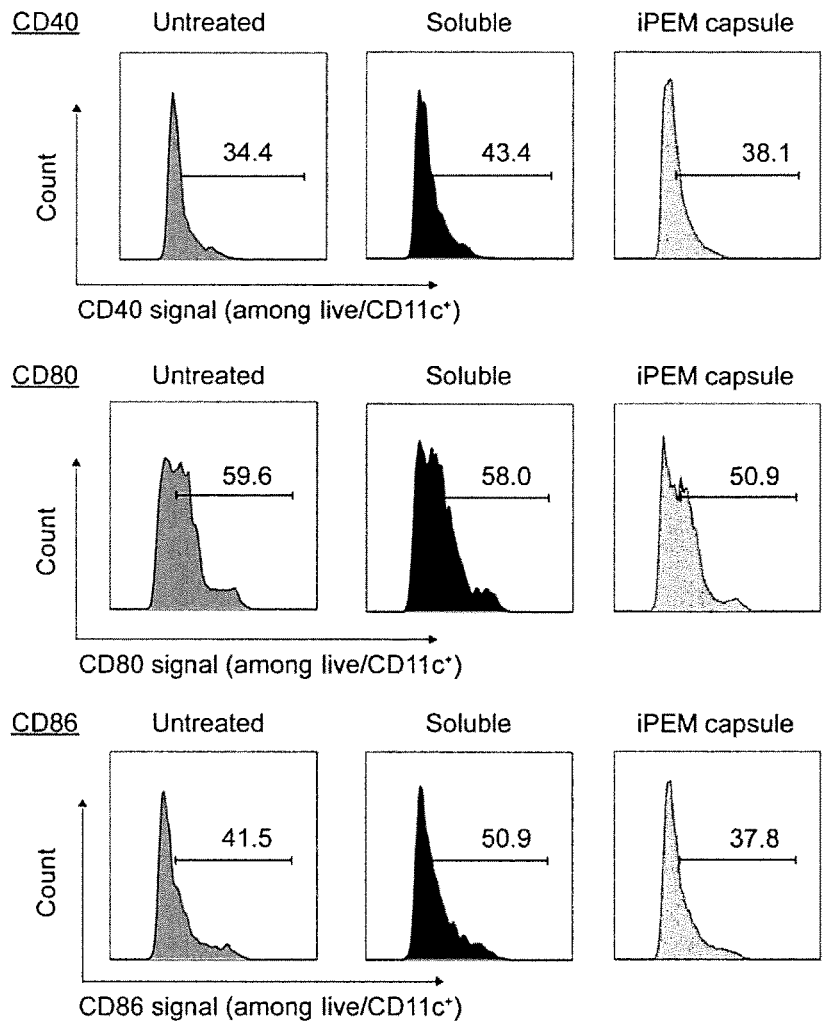
FIG. 20. In vivo activation of spleen-resident DCs by iPEM capsules. a) Representative flow cytometry histograms of CD40, CD80, and CD86 expression among DCs isolated from spleens of untreated mice, or mice immunized with antigen and adjuvant in soluble form or assembled into iPEM capsules. Spleens were harvested and analyzed three days after immunization. b) Frequencies of CD40, CD80, and CD86 expression in DCs from spleens corresponding to the groups described in (a). Values for all panels indicate the mean±s.e.m. (N=4 mice/group). Data are representative of 3 similar experiments. For a) and b) the order of the data summarized in the panels is from left to right Untreated, Soluble, iPEM capsule.
Figure 20:
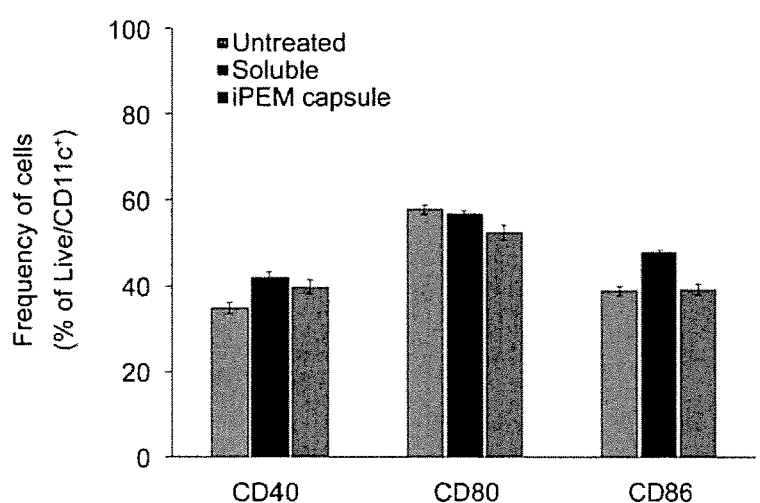
Figure 21:
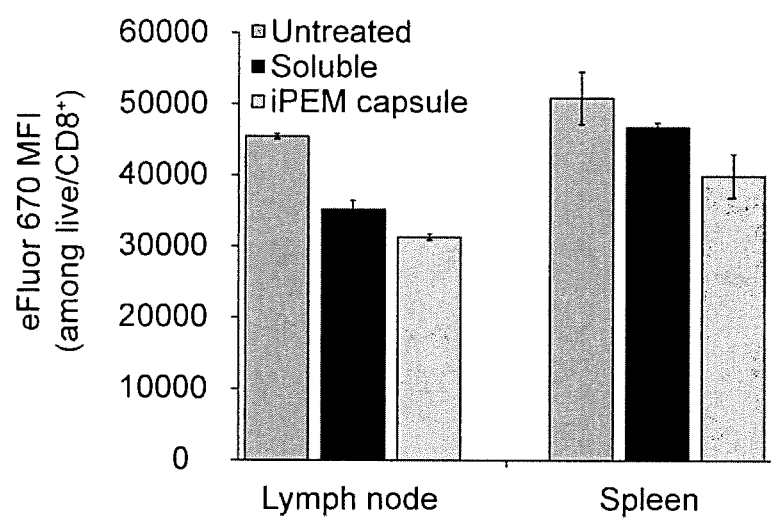
FIG. 21. iPEM capsule immunization enhances the ability of DCs to expand antigen-specific T cells. MFI of fluorescent dye used to indicate proliferation (eFluor 670) of OT-I CD8+ T cells following 48 hrs of co-culture with DCs isolated from lymph nodes and spleens of untreated mice, or mice immunized with the indicated formulations. Values indicate the mean±s.e.m. (N=4 mice/group). Data are representative of 2 similar experiments.

To investigate the mechanisms behind the enhanced immunogenicity of iPEMs compared with mixtures of peptide and adjuvant, groups of mice were immunized with iPEM capsules or the free form of the vaccine. After three days spleens and lymph nodes were harvested. Immunofluorescent staining at this time revealed iPEMs distributed throughout the cortex of the lymph node (FIG. 15A). Antigen and adjuvant were co-localized, as indicated by the yellow signal resulting from overlapping red (polyIC) and green (SIIN*) fluorescence. This ability to co-deliver cargo to secondary lymph organs is an attractive feature for vaccination and immunotherapy. Next, DC activation was assessed quantitatively in these tissues using flow cytometry. Compared with untreated groups or groups immunized with soluble vaccine, mice immunized with iPEM capsules exhibited upregulation of surface activation and co-stimulatory markers (e.g., CD40, CD80, and CD86) in draining lymph nodes (FIG. 15B; FIG. 19), but not in spleens (FIG. 15C; FIG. 20). This finding suggests that iPEM capsules locally enhance the function of DCs sampling the incoming signals from lymphatics (i.e., in draining lymph nodes). In a subsequent study, isolated DCs from identically-immunized mice were co-cultured with $CD8^+$ T cells from OT-I mice, a strain in which $CD8^+$ T cells proliferate upon encounter of SIIN presented via DCs with appropriate co-stimulatory signals. In these studies, DCs from iPEM capsule-immunized mice drove greater T cell proliferation compared with DCs from mice immunized with simple mixtures of peptide and adjuvant (FIG. 15D, E; FIG. 21). These effects translated to enhanced cytokine response, with T cells secreting significantly greater IFN-γ (FIG. 21F).

Throughout the results presented in this Example, we generally observed that iPEM capsules enhanced the function of DCs (e.g., activation, cytokine secretion) and T cells (e.g., antigen-specific proliferation). These enhancements likely resulted at least in part from the improved uptake and recognition associated with immune signals in a particulate form. Since iPEMs do not require a carrier component, the high density of signals in these structures and the tight colocalization of antigen and adjuvant might be one feature that contributes to the enhanced co-stimulation and immunogenicity that was observed. Additionally, nona-arginine is a cell penetrating peptide (CPP) that supports cargo internalization, including both antigens and adjuvants. Copolovici, D. et a. *ACS nano* 2014, 8 (3), 1972-94. Recent work reveals that intracellular proteases can efficiently process CPPs, and that these moieties can enhance DC function and cross-presentation when antigens are present. (Zhang, T. T.; *Vaccine* 2012, 30 (4), 784-93). These features of CPPs may also contribute to the greater potency of polyIC and peptides in iPEM vaccines compared with free forms of peptide and adjuvant.

An aspect of this disclosure relates to simplification of vaccine composition and synthesis while maintaining useful features of biomaterial carriers (e.g., co-delivery of vaccine components, high signal densities, tunable sizes). This is an important approach for the biomaterials and immunomodulatory files because recent studies demonstrate that many ubiquitous vaccine carriers exhibit intrinsic inflammatory functions. Designing "carrier-free" vaccines and compositions for inducing tolerance comprises new rational design methodologies that significantly improve the potency and selectivity of these approaches.

Without intending to be constrained by any particular theory, iPEM capsules offer several attractive features including facile incorporation of different types of antigens and adjuvants, elimination of potential confounding effects from intrinsic immunogenicity of polymers, and cargo loading densities of 100% (compared with typical loadings of 0.5-5% obtained with cargo loaded in polymer particles or matrices; see for example, [35-36]. Further, iPEM assembly does not require solvents, heating/cooling, synthetic polymers, water-insoluble components, or mixing. Thus, it is expected that various aspects of the present disclosure will improve the specificity and effectiveness of new immunomodulatory approaches by harnessing immunological building blocks as both nanostructured carriers and as signals that actively direct immune response.

The following materials and methods were used in generating the results presented in this example.

Materials. SIINFEKL (SIIN; (SEQ ID NO:15)) and SIINFEKL-$R_9$ (SIIN*; SEQ ID NO:16)) were synthesized by Genscript with >98% purity, with or without a FITC label on the N-terminus. Polyinosinic-polycytidylic acid, low molecular weight (polyIC) was purchased from Invivogen. Non-immunostimulatory control oligonucleotide (ODN, TCCTGAGCTTGAAGT (SEQ ID NO:17)) was synthesized with a phosphorothioate backbone by IDT. Label-IT nucleic acid labeling kits (Cy5) were purchased from Minis Bio LLC. PolyIC was labeled according to the manufacturer's protocol.

iPEM capsule synthesis. iPEM capsules were synthesized by coating sacrificial colloidal supports with PEMs consisting of SIIN* and polyIC, followed by removal of the core. To form the sacrificial templates from $CaCO_3$, spherical particles were precipitated by adding equal volumes of 0.33 M $CaCl_2$ (Sigma) into 0.33 M $Na_2CO_3 \cdot 2H_2O$ (Sigma) while mixing at 800 rpm on a stir plate for 5 min. SIIN* and polyIC were prepared in PBS with 0.5 M NaCl and adjusted to the indicated pH values using 0.1 M NaOH. Wash buffer consisted of pH 8, 0.05 M NaCl in PBS. 300 µL of $CaCO_3$ containing 3.69 mg of particles was initially washed twice with wash buffer by incubating particles for 30 sec, then centrifuging particles for 5 sec using a Quickspin Micro 1207 Microcentrifuge (VWR). This sequence was repeated for the second wash. The templates were then suspended in 300 µL of SIIN* solution (1.0 mg/mL) for 1 min and washed three times as above. The washed particles were then collected and suspended for 1 min in 300 µL of either polyIC (1.0 mg/mL) or ODN (1.0 mg/mL). Particles were washed three times as above and the sequence was repeated for up to 3 cycles to form $CaCO_3$ particles coated with $(SIIN^*/polyIC)_3$ or $(SIIN^*/ODN)_3$. The sacrificial templates were removed by collecting the particles with centrifugation (1 min, 1000 g), followed by resuspension in 300 µL of 0.1 M EDTA at the indicated pH values for 30 min. Particles were then washed twice to remove EDTA and finally resuspended in PBS.

iPEM characterization. iPEM build up on silicon and quartz chips was measured by a LSE stokes ellipsometer (Gaertner Scientific Corporation) and Evolution 60 UV-visible spectrophotometer (Thermo Scientific) to assess iPEM thickness and relative cargo loading, respectively. UV-visible spectrophotometry was used to assess relative cargo loading on quartz chips by measuring absorbance values from 200 nm to 700 nm at 1 nm intervals using a solid state sample holder. Wavelengths of 260 nm and 508 nm indicated loading of nucleic acid and peptide, respectively. At least five regions throughout each chip were measured after every 2 bilayers. A Leica SP5X confocal microscope was used to visualize co-localization of both fluorescently-tagged SIIN* (FITC) and polyIC (Cy5) in iPEM capsules. Loading of antigen and adjuvant on sacrificial cores was assessed by measuring the absorbance of the nucleic acid (260 nm) and peptide (FITC, 495 nm) dipping solutions and wash buffer by UV-visible spectrophotometery. Loading of immune signals in iPEM capsules was assessed by incubating capsules in 300 µL of trypsin (0.05%) at 37° C. for 1 hr, then measuring the peptide (FITC; Ex: 495, Em: 520) and polyIC (Cy5; Ex: 650, Em: 670) signals by fluorimetry using a Gemini XPS fluorescence microplate reader (Molecular Devices). Capsule sizes were measured using ImageJ to analyze diameters of at least 50 particles. For stability studies, capsules were incubated in PBS, incomplete media (RPMI), or complete DC media (with 10% FBS; detailed below) at 37° C. and the size was measured at the indicated times.

In vitro dendritic cell studies. All animal and cell experiments were approved by the institutional animal care and use committee (IACUC) at University of Maryland, College Park. Splenic dendritic cells (DCs) were isolated from C57BL/6 mice purchased from The Jackson Laboratory (Bar Harbor, Me.) with CD11c positive magnetic isolation kit (Miltenyi) following the manufacturer's instructions. Briefly, after euthanizing mice, spleens were harvested and minced by forceps. Minced spleens were incubated with 4 mL of spleen dissociation medium (Stemcell) for 30 min at 37° C. followed by homogenizing with a 16 G needle and 3 mL syringe. To the homogenized medium, 80 µL of 0.5 M EDTA was added at a final concentration of 10 mM and incubated for 5 min at room temperature, then passed through a 70 µm cell strainer (BD Biosciences) and centrifuged at 300 g for 10 min at 4° C. to acquire splenocytes. Cells were then resuspended with 400 µL of MACS buffer (1% BSA+2 mM EDTA in PBS) per $10^8$ cells and mixed with 100 µL of CD11c microbeads per $10^8$ cells and incubated for 15 min at 4° C. After incubation, cells were washed with 49 mL buffer and centrifuged at 200 g for 10 min at 4° C. Washed cells were then re-suspended in 500 µL buffer per $10^8$ cells and passed through a pre-wetted LS column (Miltenyi) in a magnet followed by washing three times with 3 mL MACS buffer. After the last wash, the LS column was removed from the magnet and flushed with 5 mL buffer. The flushed cell suspension was then centrifuged at 300 g for 10 min at 4° C. to collect pelleted cells. The cell pellet was then resuspended with 1 mL DC medium (RPMI1640, 10% FBS, 0.5% Penicillin Streptomycin, 50 µM 2-mercaptoethanol (2-ME)) prior to use.

For cytokine studies, capsules were serially diluted and added to DCs ($1 \times 10^5$ cells/well) to reach final capsule concentrations of 42, 21, 10, 5, 3, or 1 µg/mL. Controls included untreated DCs, soluble peptide SIIN (5 µg/mL), LPS (1 µg/mL), polyIC (10 µg/mL), LPS (1 µg/mL)+SIIN (5 µg/mL), and polyIC (10 µg/mL)+SIIN (5 µg/mL). After 24 hrs, supernatants were collected and analyzed by ELISA.

TLR3 signaling assay. The ability of iPEMs to activate TLR3 signaling was investigated using HEK-Blue mTLR3 reporter cells (Invivogen). Cells were seeded in 96 well plates with $5 \times 10^5$ cells/well in 200 µL of HEK-Blue™ detection medium. Cells were treated with TLR2a: Pam3CSK4 (200 ng/mL; Invivogen), TLR3a: polyIC (10 µg/mL; Invivogen), TLR4a: LPS (1 µg/mL; Sigma), non-immunogenic control ssDNA: ODN (10 µg/mL), iPEM capsules $(SIIN^*/polyIC)_3$, or non-immunogenic iPEM capsules $(SIIN^*/ODN)_3$. After 24 hrs, TLR3 signaling was measured by absorbance at 625 nm using a spectrophotometer.

In vitro $CD8^+$ T cell expansion. OT-I mice (C57BL/6-Tg (TcraTcrb) 1100 Mjb/J) were purchased from The Jackson Laboratory (Bar Harbor, Me.).[1] Three days after immunization, CD11c-enriched DCs from naïve, soluble vaccine-immunized, and iPEM capsule-immunized C57BL/6 mice were isolated. T cells were isolated from the spleens of OT-I mice using a negative selection CD8 isolation kit (Stemcell). Briefly, splenocytes were resuspended at $1 \times 10^8$ cells/mL (up to 8 mL total volume) followed by adding 50 µL of normal rat serum (Stemcell) per 1 mL of cells. After mixing, 50 µL of mouse $CD8^+$ T Cell Isolation Cocktail (Stemcell) per 1 mL of cells was added and incubated at room temperature for 10 min. Streptavidin RapidSpheres (Stemcell) were then added to the cell suspension at 125 µL/mL of cells and incubated at room temperature for 5 min. After incubation, the cell suspension volume was brought to a total volume of 5 mL (for $<4 \times 10^8$ cells) with recommended medium (0.5% BSA and 0.2 mM EDTA in PBS). The cell suspension was placed in a 14 mL tube without a cap in the magnet for 2.5 min and carefully the desired $CD8^+$ T cells were poured into a new tube. Resulting cells were washed twice to remove any serum and labeled with 5 µM of proliferation dye eFluor 670 (eBioscience) for 10 min at 37° C. in the dark. After 10 min, the dye was neutralized with 5 times volume of T cell medium (RPMI1640, 10% FBS, 1× non-essential amino acid, 10 mM HEPES, 2 mM L-glutamine, 0.5% Penicillin Streptomycin, 50 µM 2-ME) followed by washing three times with T cell medium. Resulting cells ($3 \times 10^5$ cells/50 µL) were added into wells containing DCs/capsules and incubated for 48 hrs for the T cell co-culture assay. After 48 hrs, the resulting cell population was divided into two portions for proliferation analysis and intracellular cytokine staining (ICCS).

To assess T cell proliferation, cells were blocked with anti-CD16/32 using established techniques and stained with anti-CD3e (PE-Cy7) and anti-CD8a (APC) for CD8$^+$ T cells. For ICCS staining, culture medium was replaced with T cell medium supplemented with 1/1000 dilution of brefeldin A (BFA, eBioscience) and incubated for 4 hrs at 37° C. Cells were then washed with ice cold FACS buffer, and blocked with anti-CD16/32 for 10 min, followed by staining for CD3e (PE-Cy7) and CD8a (APC) for 20 min at 4° C. After surface staining, cells were washed twice with ice cold FACS buffer and fixed and permeabilized with a Cytofix/Cytoperm kit (BD Biosciences). Briefly, 100 µL of fixation solution was added to each well and incubated at 4° C. for 20 min followed by washing twice with 200 µL of permeabilization washing buffer. Anti-IFN-γ (PE) antibody was diluted in permeabilization washing buffer and cells were stained for 30 min at 4° C. After staining, cells were washed twice with 200 µL of permeabilization washing buffer and resuspended in 100 µL FACS buffer prior to flow cytometry analysis.

Immunization. Six to eight week old C57BL/6 female mice from The Jackson Laboratory, in groups of 8 were used in immunization studies, along with untreated control groups (N=4). Mice were immunized by intradermal injection (25 µL) on each flank with either capsules, free SIINFEKL (SEQ ID NO:15) and polyIC, or left untreated. Capsule vaccines and soluble vaccines formulated in simple mixtures were prepared and administered using matching doses of peptide (60 µg) and polyIC (240 µg). Mice were injected at day 0 and in some studies boosted at day 15 and day 28 as indicated in the main text.

Tumor studies. Six to eight week old C57BL/6 female mice from The Jackson Laboratory were randomized in groups of 6. Mice were then immunized at day 0 and boosted at day 15 and day 28 with the formulations indicated in the main text. At day 36, mice were inoculated subcutaneously in the flank using an aggressive dose of 1×10$^6$ B16 tumor cells expressing OVA. Body weight was monitored, and tumor burdens were calculated daily as the product of two orthogonal diameters. Mice were euthanized according to IACUC-approved humane endpoints when the aggregate burden reached 150 mm$^2$.

In vivo analysis of antigen-specific CD8$^+$ T cell expansion. Following immunization, blood samples were collected by submandibular bleeding at days 7, 14, 22, 29, and 41. Blood was treated with 1 mL ACK lysing buffer (Life Technologies) for 3 min and centrifuged at 500 g for 5 min. This process was repeated and cells were then washed once in PBS. To assess the frequency of antigen-specific CD8$^+$ T cells, samples were blocked with anti-CD16/32 for 10 min, followed by staining with MHC-I SIINFEKL (SEQ ID NO:15) tetramer (PE-conjugated, MBL International Corp.) for 30 min. Cells were then stained with anti-CD8a (APC) for 20 min, washed twice with FACS buffer, and resuspended in 100 FACS buffer containing DAPI for measurement by flow cytometry.

ELISA assay. All ELISA assays were conducted using mouse IL-1β, IL-6, and IFN-γ OptEIA reagents according to the manufacturer's instructions (BD Biosciences). Supernatants were collected and analyzed without purification using 4-10× dilutions.

Mechanistic in vivo studies. Six to eight week old C57BL/6 female mice from The Jackson Laboratory were immunized by intradermal injection with capsules, soluble SIIN and polyIC, or left untreated as above. Three days after immunization, DCs from draining lymph nodes and spleens were isolated by positive CD11c selection as described above. Cells were then stained with antibodies against classical DC activation markers and analyzed by flow cytometry, as above. To test if DCs isolated from immunized mice present peptides from iPEM capsules in a manner that can expand antigen-specific CD8$^+$ T cells (OT-I), DCs isolated from iPEM-immunized mice on Day 3 were co-cultured with CD8$^+$ T cell from OT-I mice for 48 hrs. Proliferation and cytokine secretion were then assessed by fluorescence dilution assays and ELISA as described above. For immunohistochemical analysis, lymph nodes were removed on day 3, frozen, sectioned at 10 µm intervals, then the tissue was fixed. Fixed sections were blocked with 5% donkey serum (Sigma) and 5% goat serum (Sigma) in PBS for 30 min. After a PBS wash, samples were stained for T cells with a purified rabbit anti-mouse antibody (CD3e, Abcam) for 1 hr at room temperature, then washed twice and stained with a fluorescently-conjugated antibody for B cells (rat anti-mouse B220 APC, eBioscience) and a goat anti-rabbit antibody (Dylight 405, Jackson Immunoresearch). Stained sections were washed then fixed in in 4% paraformaldehyde before quenching in 1% glycerol. Sections were then mounted with Prolong Diamond Antifade Mountant (Life Sciences), and imaged.

Statistical Analysis. Statistical analysis was carried out using one way analysis of variance (ANOVA) with a Tukey post test in GraphPad Prism v.6.02. Survival analysis was carried out using a Logrank test. Statistical significance was defined at p values≤0.05 (95% confidence interval) and indicated as *=p≤0.05, =p≤0.01, *=p≤0.001.

Example 3

This Example provides a non-limiting example of making and using iPEMs to induce tolerance.

As discussed above, the iPEM structure enables co-location and subsequently, co-delivery of immune signals to generate tolerance, e.g. expansion of antigen-specific regulatory T cells, which can be significant in this aspect of the disclosure because delivering a first immune signal compound comprising the antigen without the second immune signal compound could cause inflammation or result in lack of efficacy. In this regard, many synthetic carriers activate the inflammasome or other inflammatory pathways, which are effects that could exacerbate autoimmune disease. The presently provided iPEMs offer a original platform for controlling the individual ratios of each component, to co-deliver multiple signals, and to tune particle size or other physical characteristics, but without need for a synthetic carrier component. These features allow for programming immune tolerance by assembling and juxtaposing self-antigens and regulatory immune signals at high densities.

Induction of tolerance as an aspect of this disclosure can be demonstrated via prophylactic and therapeutic approaches to MS. As is known in the art, in MS, tissue damage results from inflammatory proteins (i.e., cytokines) produced by myelin-reactive CD4$^+$ T cells, CD8$^+$ T cells, and antibodies infiltrating the central nervous system (CNS). The phenotypes of CD4$^+$ T cells are drivers of inflammation in MS, with $T_H1$ and $T_H17$ subsets causing autoimmunity, and specialized regulatory T cells ($T_{REGS}$) dampening attack against myelin. The present disclosure relates to skewing T cell differentiation toward $T_{REGS}$ and away from inflammatory $T_H1$ and $T_H17$ cells. While $T_{REGS}$ can be specific for myelin, they exert a different function compared with $T_H1$ and T<sub>H</sub>17 cells. For example, when myelin-specific T$_{REGS}$ encounter myelin, they produce compounds that inactivate or destroy the inflammatory T$_H$1 and T$_H$17 cells that attack myelin during MS. Thus, myelin-specific T$_{REGS}$ offer the potential to suppress harmful autoimmune attacks against myelin, while leaving the rest of the immune system intact. T$_{REGS}$ can also be long-lived, creating the possibility to cure or permanently control disease. However, generating myelin-specific T$_{REGS}$ has been challenging because myelin needs to be carefully co-administered with regulatory signals to alter how the immune system responds to myelin.

We use myelin peptide (MOG)/GpG iPEMs assembled from negatively charged GpG and MOG conjugated to cationic arginine residues that create a cationic anchor to support iPEM assembly. It is expected that these compositions will deliver their signals at a high density on, for example, microneedle (MN) patches, which are able to penetrate the skin and co-deliver the two components to skin-resident immune cells (e.g., dendritic cells and Langerhans cells). MNs are made of biocompatible metals or polymers and offer efficient immune cell targeting, as well as stabilization of surface-immobilized vaccine components without refrigeration. These substrates are also too short to reach pain receptors, eliminating pain and improving patient compliance. As a result, MNs have been used to enhance traditional vaccines (e.g., against flu), but it is believed they have never previously been applied to autoimmunity. It is expected that transdermal immunization using iPEMs coated on MNs will effectively alter the interactions between antigen presenting cells (APCs) and T cells in draining lymph nodes, polarizing myelin-specific T cell response toward T$_{REGS}$ to stop or reverse disease in a gold standard mouse model of MS (experimental autoimmune encephalomyelitis, EAE). MN arrays can be applied on the day of EAE induction (day 0) for prophylactic regimens, and at disease onset (~day 10) or peak (~day 18) for therapeutic regimens. A positive control group can receive an approved MS drug, such as Copaxone (50 mg/kg/day, s.c.). The feasibility of this MN-based approach is supported by FIGS. 22-27.

Analysis of dendritic cells (DCs) in accordance with aspects of this disclosure can be performed using any suitable technique, such as by staining with antibodies for DC activation markers (e.g., CD40, CD80, CD86, MHC-II) and enumerated by flow cytometry. Determining whether iPEMs polarize T cells toward T$_{REG}$ and reduce T$_H$17 or T$_H$1 function can also be performed using any suitable approach, such as by flow cytometry using T$_{REG}$ markers (CD4$^+$/CD25$^+$/Foxp3$^+$; increased TGF-β, IL-10), T$_H$17 markers (CD4$^+$/RORγ$^+$; increased IL-17, IL-23, IFN-γ), and T$_H$1 markers (CD4$^+$/T-bet$^+$; increased IFN-γ, TNF). T This Example provides a non-limiting implementation using the EAE model, which is typically induced in female C57/BL6 mice on day 0 by injection of 200 μg of MOG$_{35-55}$ in complete Freund's adjuvant, along with i.p. injection of 150 ng of pertussis toxin on days 0 and 1. Clinical scores are assigned to mice daily using established criteria: 0) no clinical signs; 1) flaccid tail; 2) hind limb paresis/partial paralysis; 3) total hind limb paralysis; 4) hind and front limb paralysis; and 5) moribund. The EAE model provides for reliable disease progression. iPEMs used for in vivo studies can be compared with any suitable control, such as untreated mice and/or mice treated with soluble peptide or GpG. In non-limiting examples, 2-3 doses in the range of 10-200 μg of peptide and GpG coated on MN arrays can be used. In certain examples, mice receive a single MOG/GpG iPEM immunization, such as in one ear.

Figure 22:
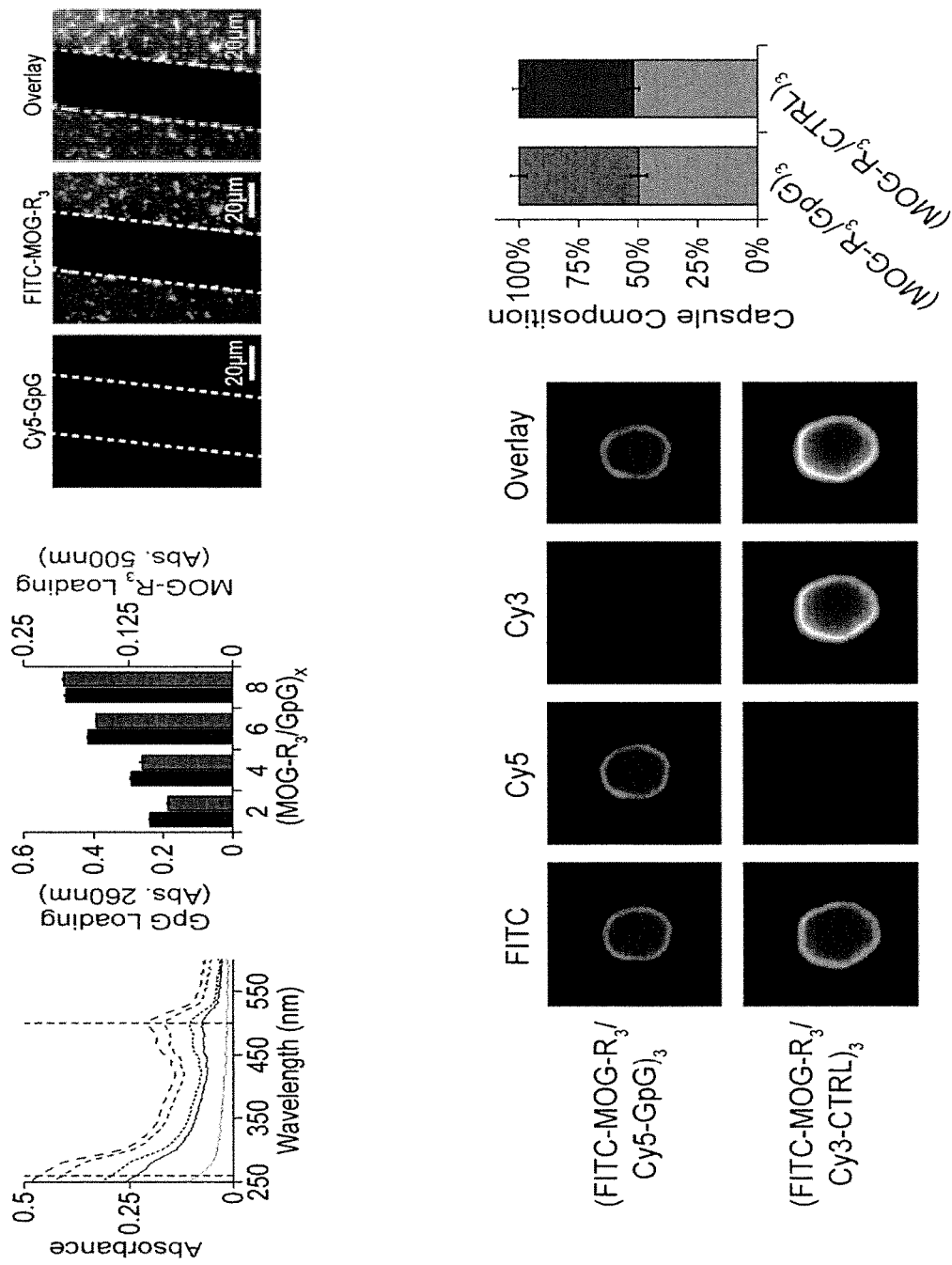
FIG. 22 demonstrates tunable assembly of iPEMs from MOG antigen and GpG or irrelevant control oligonucleotide (CTRL) on planar substrates or sacrificial colloidal templates to form iPEM capsules. In the bar graph on the right of the lower panels, the bottom of each bar is green; the top of the left bar is blue and the top of the right bar is red.

FIG. 22 demonstrates tunable assembly of iPEMs from MOG antigen and GpG or irrelevant control oligonucleotide (CTRL) on planar substrates or sacrificial colloidal templates to form iPEM capsules.

Figure 23:
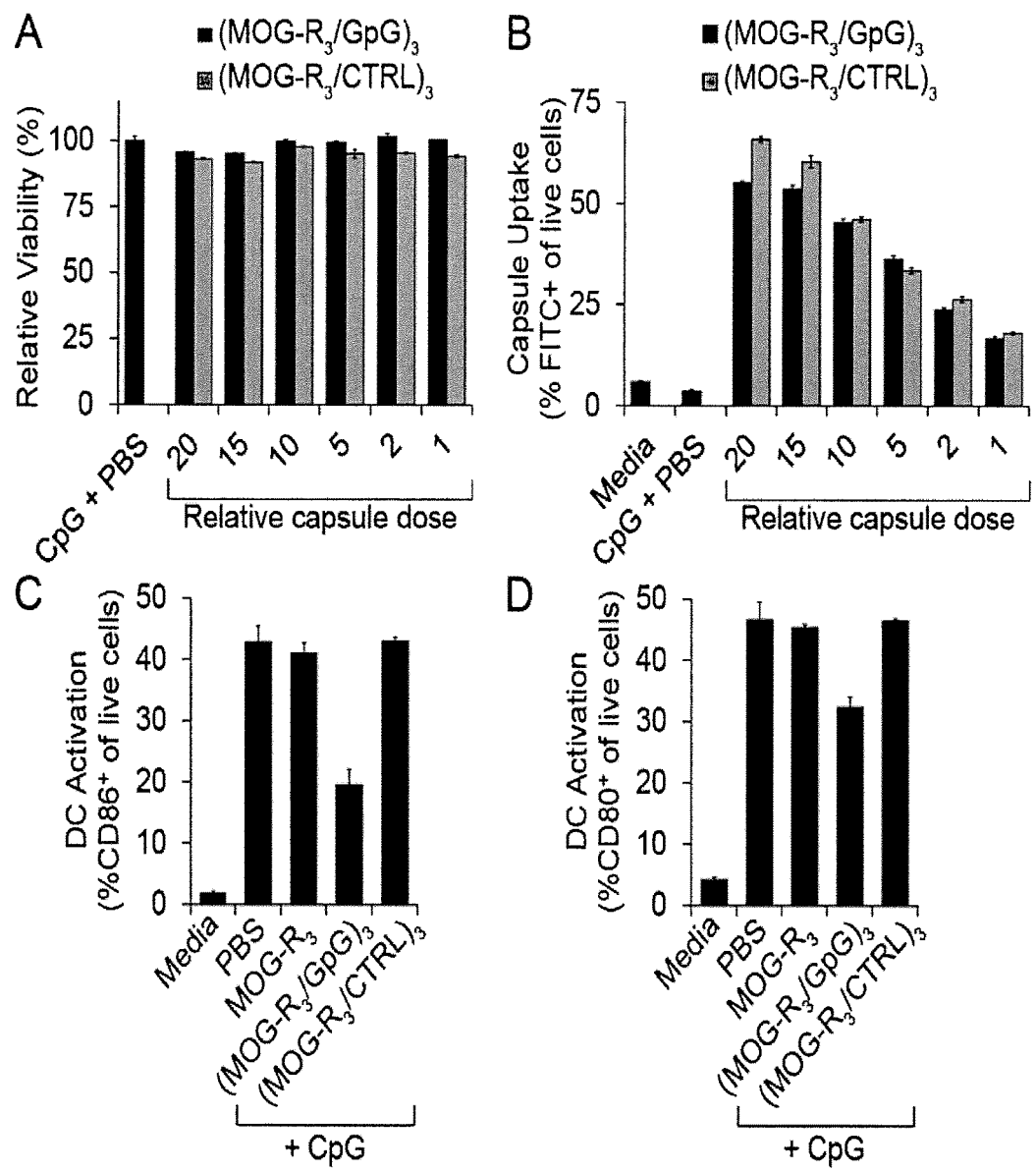
FIG. 23 demonstrates iPEM capsules are taken up by primary dendritic cells and modulate expression of surface activation markers, without associated toxicity. A), B), C), D) the data summarized are as indicated on the Y axis for each.

FIG. 23 demonstrates iPEM capsules are taken up by primary dendritic cells and modulate expression of surface activation markers, without associated toxicity. The data summarized in A, B, C, and D are as indicated on the Y axis for each.

Figure 24:
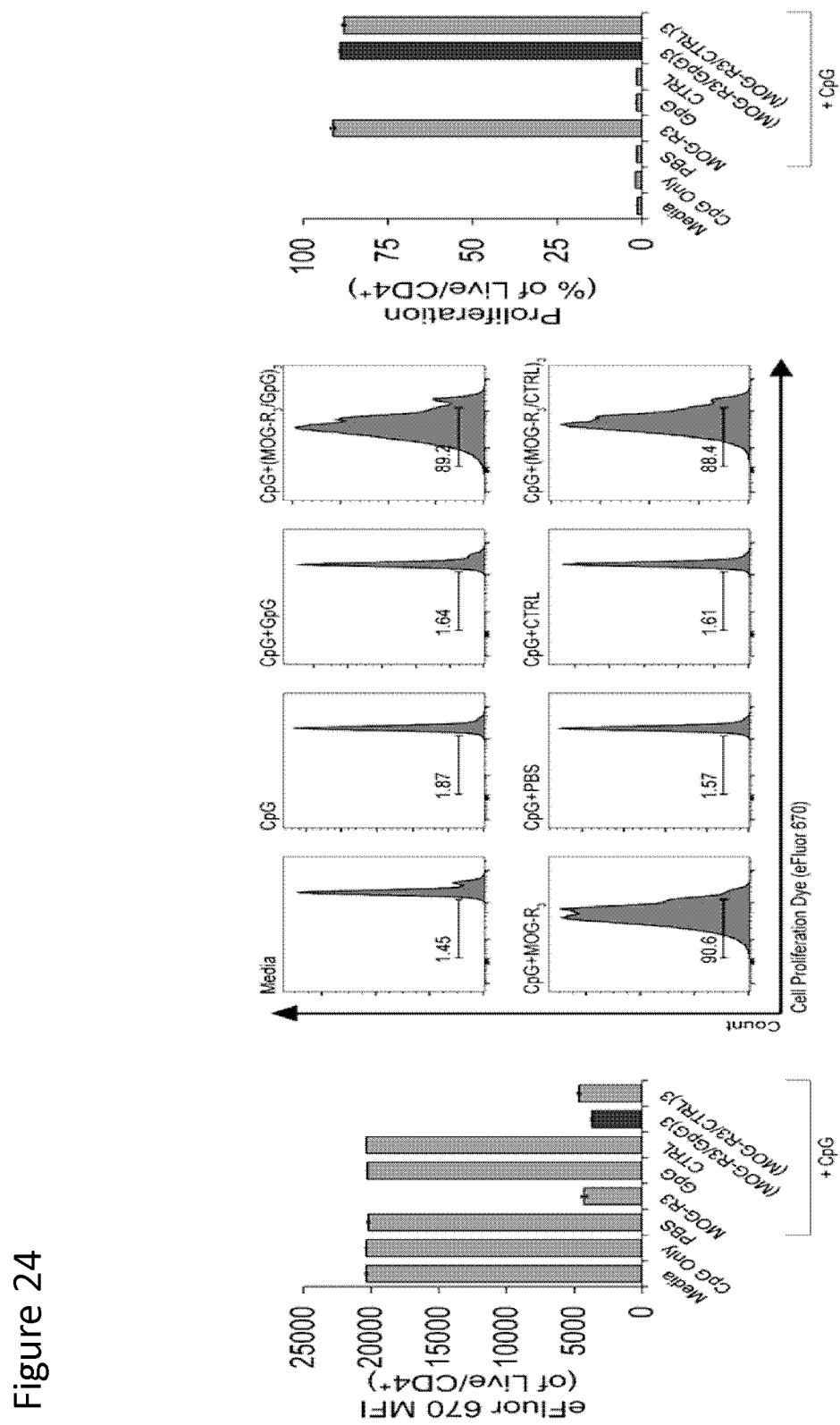
FIG. 24 demonstrates MOG antigen retains the ability to drive antigen-specific T cell proliferation after incorporation into iPEM capsules.

FIG. 24 demonstrates MOG antigen retains the ability to drive antigen-specific T cell proliferation after incorporation into iPEM capsules.

Figure 25:
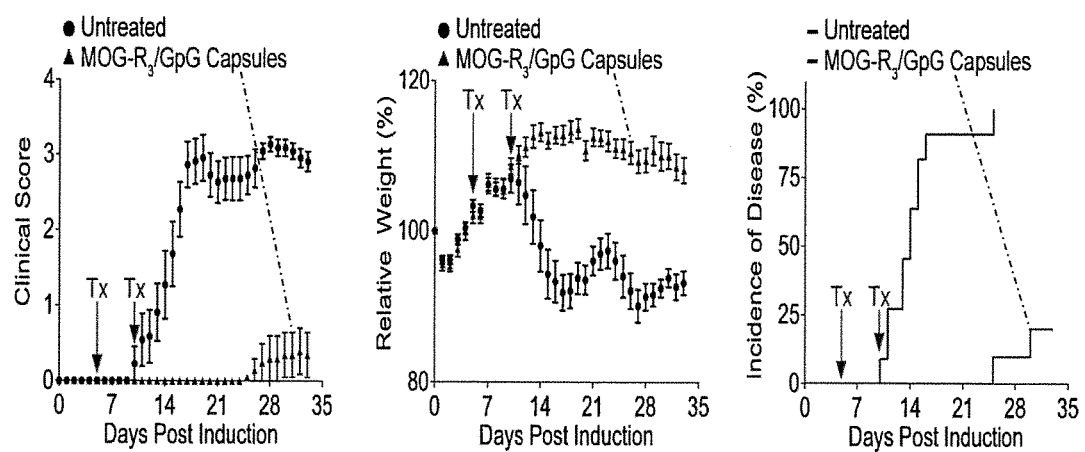
FIG. 25 demonstrates early therapeutic treatment with MOG-R3/GpG iPEM capsules halts or restrains progression of autoimmune disease in mice.

FIG. 25 demonstrates early therapeutic treatment with MOG-R3/GpG iPEM capsules halts or restrains progression of autoimmune disease in mice using the EAE model.

Figure 26:
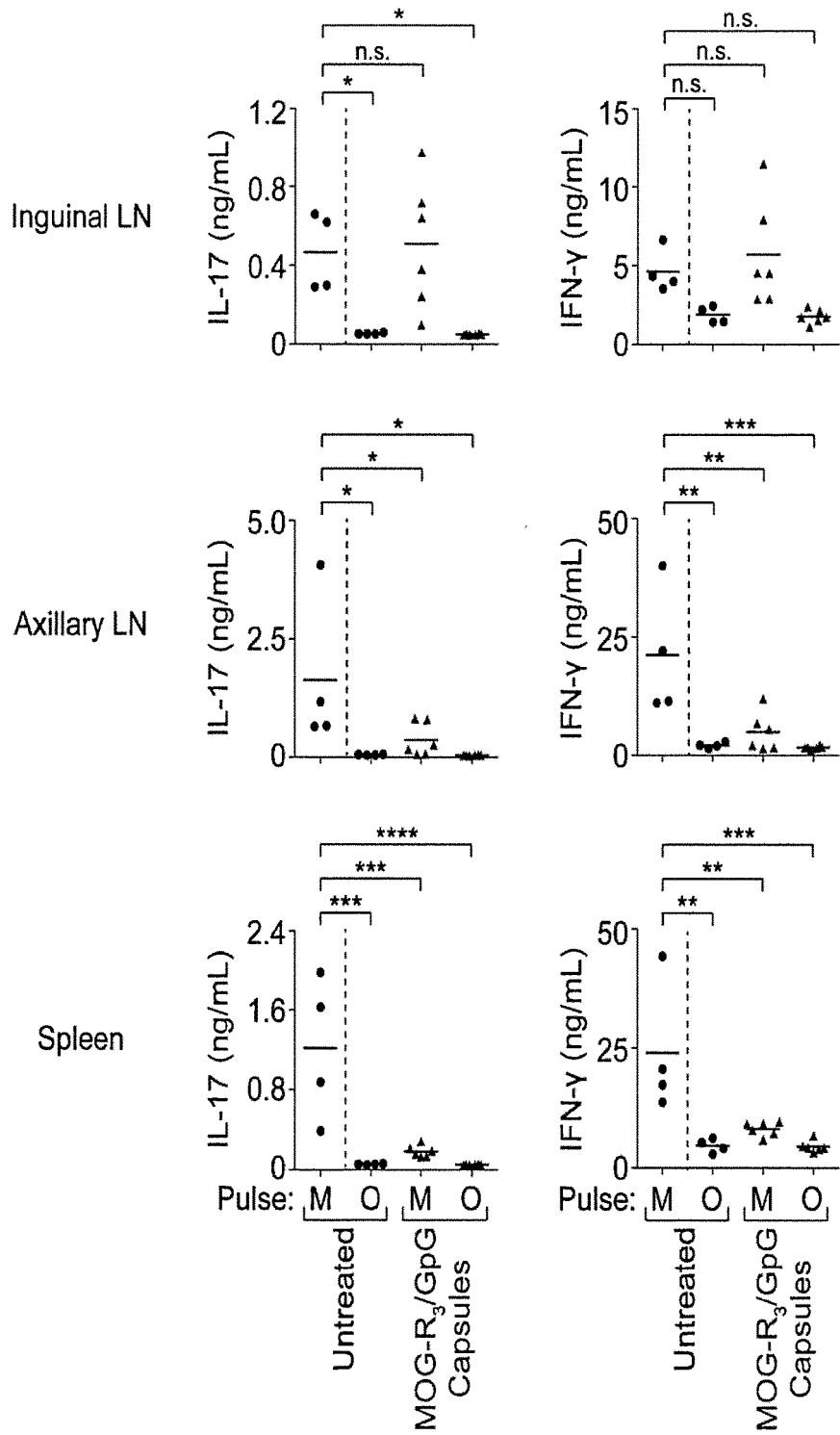
FIG. 26 demonstrates iPEM capsule treatment after EAE induction restrains self-antigen triggered inflammatory cytokine secretion in axillary LNs and spleen, but not inguinal LNs.

FIG. 26 demonstrates iPEM capsule treatment after EAE induction restrains self-antigen triggered inflammatory cytokine secretion in axillary LNs and spleen, but not inguinal LNs.

Figure 27:
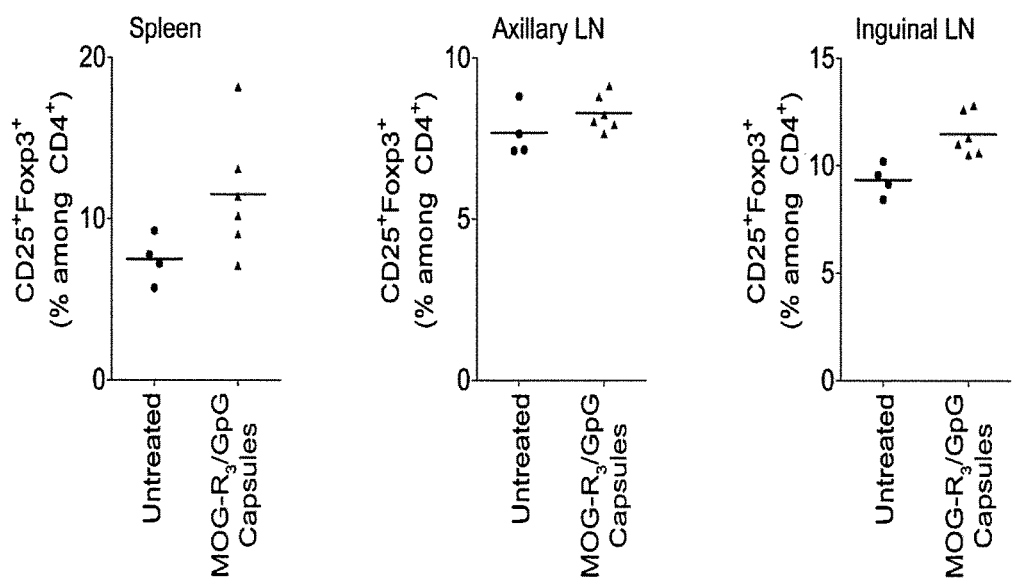
FIG. 27 demonstrates iPEM capsule treatment following EAE induction drives expansion of regulatory T cells in inguinal LNs.

FIG. 27 demonstrates iPEM capsule treatment following EAE induction drives expansion of regulatory T cells in inguinal LNs.

While the disclosure has been particularly shown and described with reference to specific embodiments (some of which are preferred embodiments), it should be understood by those having skill in the art that various changes in form and detail may be made therein without departing from the spirit and scope of the present disclosure as disclosed herein.

The invention claimed is:

1. A composition consisting essentially of:
   a) a first layer of a first immune signal compound; and
   b) a second layer of the first immune signal compound or a second immune signal compound disposed on the first layer of the first immune signal compound;
   wherein the first and second immune signal compounds are independently selected from peptides, polypeptides, nucleic acids, and charged derivatives thereof, and the first immune signal compound and the second immune signal compound have oppositely charged domains, and wherein the first or second immune signal compound is a nucleic acid that is a Toll-like-receptor (TLR) ligand.

2. The composition of claim 1, wherein the composition further comprises 1 to 40 additional layer(s) of the first and second immune signal compounds, the layer(s) are disposed on the adjacent layers, and the adjacent layers have opposite charge.

3. The composition of claim 1, wherein the first or the second immune signal compound is a peptide or polypeptide or charged derivative thereof comprising an antigen expressed by a cancer cell or a pathogen.

4. The composition of claim 1, wherein the first or second immune signal compound is a peptide or polypeptide or charged derivative thereof comprising a self-antigen or an allergen.

5. The composition of claim 1, wherein the composition further comprises a substrate and the first layer of the first immune signal compound is disposed on at least a portion of a surface of the substrate.

6. The composition of claim 5, wherein the substrate is a sacrificial substrate.

7. The composition of claim 6, wherein the sacrificial substrate is calcium carbonate, magnesium carbonate, cadmium carbonate, melamine formaldehyde, silicon dioxide, or cells.

8. The composition of claim 5, wherein the substrate is a nanoparticle or microparticle.

9. The composition of claim 8, wherein the substrate is a metal core.

10. The composition of claim 5, wherein the substrate is a microscope slide, scaffold, biomedical implant, a biomedical device, or a microneedle array.

11. The composition of claim 1, wherein the composition encompasses a three-dimensional void.

12. The composition of claim 11, wherein a distinct immune signal compound and/or a drug is sequestered in the three-dimensional void.

13. A method of modulating an immune response comprising administering a composition of claim 1 to an individual in need thereof such that the immune response is modulated.

14. The method of claim 13, wherein the individual is in need of stimulation of an immune response to an antigen, and wherein the first or second immune signal compound comprises the antigen, wherein the modulating of the immune response comprises the stimulation of the immune response to the antigen.

15. The method of claim 14, wherein the antigen is comprised within a peptide or polypeptide expressed by a cancer cell or a pathogen.

16. The method of claim 13, wherein the individual is in need of immune tolerance to an antigen, wherein the first immune signal compound comprises the antigen, wherein the modulating of the immune response comprises inducing the tolerance to the antigen.

17. The method of claim 16, wherein the antigen is a self-antigen or is an allergen.

18. The method of claim 17, wherein the second immune signal compound promotes development of regulatory T cells.

19. A method for inducing tolerance to an antigen in an individual in need thereof, the method comprising administering the composition of claim 1 to an individual in need thereof, and wherein tolerance to the antigen is induced.

20. The method of claim 19, wherein the antigen comprises a self-antigen or an allergen.

21. The method of claim 20, wherein the self-antigen comprises a myelin antigen.

* * * * *

SEQUENCE LISTING

<160> NUMBER OF SEQ ID NOS: 16

<210> SEQ ID NO 1
<211> LENGTH: 20
<212> TYPE: PRT
<213> ORGANISM: human

<400> SEQUENCE: 1

Ala Val Gly Ala Leu Glu Gly Pro Arg Asn Gln Asp Trp Leu Gly Val
1               5                   10                  15

Pro Arg Gln Leu
            20

<210> SEQ ID NO 2
<211> LENGTH: 8

```
<212> TYPE: PRT
<213> ORGANISM: human

<400> SEQUENCE: 2

Lys Val Pro Arg Asn Gln Asp Trp
1               5

<210> SEQ ID NO 3
<211> LENGTH: 9
<212> TYPE: PRT
<213> ORGANISM: human

<400> SEQUENCE: 3

Ser Val Tyr Asp Phe Phe Val Trp Leu
1               5

<210> SEQ ID NO 4
<211> LENGTH: 9
<212> TYPE: PRT
<213> ORGANISM: human

<400> SEQUENCE: 4

Thr Ala Pro Asp Asn Leu Gly Tyr Ala
1               5

<210> SEQ ID NO 5
<211> LENGTH: 9
<212> TYPE: PRT
<213> ORGANISM: human

<400> SEQUENCE: 5

Thr Ala Pro Asp Asn Leu Gly Tyr Met
1               5

<210> SEQ ID NO 6
<211> LENGTH: 8
<212> TYPE: PRT
<213> ORGANISM: human

<400> SEQUENCE: 6

Trp Glu Pro Asp Asp Asn Pro Ile
1               5

<210> SEQ ID NO 7
<211> LENGTH: 9
<212> TYPE: PRT
<213> ORGANISM: human

<400> SEQUENCE: 7

Glu Glu Leu Thr Val Ser Glu Phe Leu
1               5

<210> SEQ ID NO 8
<211> LENGTH: 21
<212> TYPE: PRT
<213> ORGANISM: human

<400> SEQUENCE: 8

Met Glu Val Gly Trp Tyr Arg Ser Pro Phe Ser Arg Val Val His Leu
1               5                   10                  15

Tyr Arg Asn Gly Lys
            20

<210> SEQ ID NO 9
```

```
<211> LENGTH: 13
<212> TYPE: PRT
<213> ORGANISM: human

<400> SEQUENCE: 9

His Ser Leu Gly Lys Trp Leu Gly His Pro Asp Lys Phe
1               5                   10

<210> SEQ ID NO 10
<211> LENGTH: 14
<212> TYPE: PRT
<213> ORGANISM: human

<400> SEQUENCE: 10

Asn Thr Trp Thr Thr Cys Gln Ser Ile Ala Phe Pro Ser Lys
1               5                   10

<210> SEQ ID NO 11
<211> LENGTH: 21
<212> TYPE: PRT
<213> ORGANISM: human

<400> SEQUENCE: 11

Val His Phe Phe Lys Asn Ile Val Thr Pro Arg Thr Pro Pro Pro Ser
1               5                   10                  15

Gln Gly Lys Gly Arg
            20

<210> SEQ ID NO 12
<211> LENGTH: 33
<212> TYPE: PRT
<213> ORGANISM: artificial sequence
<220> FEATURE:
<223> OTHER INFORMATION: designed amino acid sequence

<400> SEQUENCE: 12

Ser Val Tyr Asp Phe Phe Val Trp Leu Ala Ala Tyr Ser Val Tyr Asp
1               5                   10                  15

Phe Phe Val Trp Leu Ala Ala Tyr Ser Val Tyr Asp Phe Phe Val Trp
            20                  25                  30

Leu

<210> SEQ ID NO 13
<211> LENGTH: 22
<212> TYPE: DNA
<213> ORGANISM: artificial sequence
<220> FEATURE:
<223> OTHER INFORMATION: TLR9 antagonist

<400> SEQUENCE: 13
tgactgtgaa ggttagagat ga                                          22

<210> SEQ ID NO 14
<211> LENGTH: 9
<212> TYPE: PRT
<213> ORGANISM: human

<400> SEQUENCE: 14

Glu Gly Ser Arg Asn Gln Asp Trp Leu
1               5

<210> SEQ ID NO 15
<211> LENGTH: 8
<212> TYPE: PRT
```

```
<213> ORGANISM: artificial sequence
<220> FEATURE:
<223> OTHER INFORMATION: Ovalbumin peptide model antigen

<400> SEQUENCE: 15

Ser Ile Ile Asn Phe Glu Lys Leu
1               5

<210> SEQ ID NO 16
<211> LENGTH: 15
<212> TYPE: DNA
<213> ORGANISM: artificial sequence
<220> FEATURE:
<223> OTHER INFORMATION: synthesized ODN

<400> SEQUENCE: 16
tcctgagctt gaagt                                                    15
```